United States Patent
Oestergaard et al.

(10) Patent No.: US 9,714,288 B2
(45) Date of Patent: Jul. 25, 2017

(54) ANTISENSE COMPOUNDS AND USES THEREOF

(71) Applicants: The Regents of the University of California, Oakland, CA (US); Isis Pharmaceuticals, Inc., Carlsbad, CA (US)

(72) Inventors: Michael Oestergaard, Carlsbad, CA (US); Punit P. Seth, Carlsbad, CA (US); Shuling Guo, Carlsbad, CA (US); Noriko Satake, Davis, CA (US); Nitin Nitin, Davis, CA (US); Joseph M. Tuscano, Davis, CA (US)

(73) Assignees: The Regents of the University of California, Oakland, CA (US); Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 14/871,862

(22) Filed: Sep. 30, 2015

(65) Prior Publication Data
US 2016/0090598 A1    Mar. 31, 2016

Related U.S. Application Data

(60) Provisional application No. 62/057,985, filed on Sep. 30, 2014, provisional application No. 62/084,333, filed on Nov. 25, 2014, provisional application No. 62/113,007, filed on Feb. 6, 2015.

(51) Int. Cl.
| | |
|---|---|
| *A61K 31/70* | (2006.01) |
| *C07H 21/02* | (2006.01) |
| *C07H 21/04* | (2006.01) |
| *C07K 16/28* | (2006.01) |
| *A61K 31/475* | (2006.01) |
| *A61K 31/704* | (2006.01) |
| *A61K 47/48* | (2006.01) |
| *A61K 31/713* | (2006.01) |
| *A61K 31/00* | (2006.01) |
| *C12N 15/113* | (2010.01) |
| *C12N 5/00* | (2006.01) |

(52) U.S. Cl.
CPC .......... *C07K 16/2803* (2013.01); *A61K 31/00* (2013.01); *A61K 31/475* (2013.01); *A61K 31/704* (2013.01); *A61K 31/713* (2013.01); *A61K 47/484* (2013.01); *A61K 47/4863* (2013.01); *C12N 15/1138* (2013.01); *C12N 2310/11* (2013.01); *C12N 2310/315* (2013.01); *C12N 2310/3231* (2013.01); *C12N 2310/3341* (2013.01); *C12N 2310/341* (2013.01); *C12N 2310/346* (2013.01)

(58) Field of Classification Search
None
See application file for complete search history.

(56) References Cited

U.S. PATENT DOCUMENTS

| | | |
|---|---|---|
| 7,807,619 B2 | 10/2010 | Bertozzi et al. |
| 8,420,086 B2 | 4/2013 | Govindan et al. |
| 8,431,558 B2 | 4/2013 | Bertozzi et al. |
| 8,461,298 B2 | 6/2013 | Bertozzi et al. |
| 8,519,122 B2 | 8/2013 | Jewett et al. |

FOREIGN PATENT DOCUMENTS

WO     2013/089283 A1    6/2013

OTHER PUBLICATIONS

Czech et al., "RNAi-based therapeutic strategies for metabolic disease", Nature Reviews, Endocrinology, Aug. 2011, vol. 7, pp. 473-484.
Dijoseph et al., "Therapeutic potential of CD22-specific antibody-targeted chemotherapy using inotuzumab ozogamicin (CMC-544) for the treatment of acute lymphoblastic leukemia", Leukemia, 2007, vol. 21, pp. 2240-2245.
Kato et al., "Efficacy of a CD22-targeted antibody-saporin conjugate in a xenograft model of precursor-B cell acute lymphoblastic leukemia", Leukemia Research, 2013, vol. 37, pp. 83-88.
Kumar et al., "T Cell-Specific siRNA Delivery Suppresses HIV-1 Infection in Humanized Mice", Cell, Aug. 22, 2008, vol. 134, pp. 577-586.
Palanca-Wessels et al., "AntiCD22 Antibody Targeting of pH-responsive Micelles Enhances Small Interfering RNA Delivery and Gene Silencing in Lymphoma Cells", Molecular Therapy, Aug. 2011, Vo. 19, No. 8, pp. 1529-1537.
Peer et al., "Selective gene silencing in activated leukocytes by targeting siRNAs to the integrin lymphocyte function-associated antigen-1", PNAS, Mar. 6, 2007, vol. 104, No. 10, pp. 4095-4100.
Schneider et al., "Targeted siRNA Delivery and mRNA Mediated by Bispecific Digoxigenin-binding Antibodies", Molecular Therapy-Nucleic Acids, 2012, 1(e46), pp. 1-11; doi:10.1038/mtna.2012.39.
Song et al., "Antibody mediated in vivo delivery of small interfering RNAs via cell-surface receptors", Nature Biotechnology, Jun. 2005, vol. 23, No. 6, pp. 709-717.
Walker et al., "Improved Cellular Delivery of Antisense Oligonucleotides Using Transferrin Receptor Antibody-Oligonucleotide Conjugates", Pharmaceutical Research, 1995, vol. 12, No. 10, pp. 1548-1553.

(Continued)

*Primary Examiner* — Sean McGarry
(74) *Attorney, Agent, or Firm* — Mintz Levin Cohn Ferris Glovsky and Popeo P.C.

(57) ABSTRACT

The present disclosure provides compounds comprising modified oligonucleotides and anti-CD22 antibodies. Certain such modified oligonucleotides conjugated to anti-CD22 antibodies are useful for hybridizing to a complementary nucleic acid, including but not limited, to nucleic acids in a cell. In certain embodiments, hybridization results in modulation of the amount activity or expression of the target nucleic acid in a cell.

16 Claims, 15 Drawing Sheets

(56) References Cited

OTHER PUBLICATIONS

Yu et al., "Targeted Delivery Systems for Oligonucleotide Therapeutics", The AAPS Journal, Mar. 2009, Vo. 11, No. 1, pp. 195-203.

| | Mouse | HLA% | CD22% | CD22/HLA |
|---|---|---|---|---|
| PBS | 1 | 72.5 | 70.4 | 1.0 |
| | 2 | 74.8 | 70.8 | 0.9 |
| | 3 | 62.7 | 57.6 | 0.9 |
| | 4 | 63.3 | 58.7 | 0.9 |
| free Ab (1mg/kg) + free ASO (0.8mg/kg) | 1 | 73.6 | 52.4 | 0.7 |
| | 2 | 82.7 | 72.7 | 0.9 |
| | 3 | 90.0 | 77.0 | 0.9 |
| | 4 | 80.0 | 93.2 | 1.2 |
| | 5 | 92.4 | 79.9 | 0.9 |
| | 6 | 92.6 | 77.4 | 0.8 |
| | 7 | 90.5 | 74.7 | 0.8 |
| | 8 | 92.8 | 79.1 | 0.9 |
| free Ab (5mg/kg) + free ASO (4mg/kg) | 1 | 86.3 | 83.8 | 1.0 |
| | 2 | 90.7 | 84.1 | 0.9 |
| | 3 | 91.3 | 82.2 | 0.9 |
| | 4 | 91.2 | 82.3 | 0.9 |
| free Ab (10mg/kg) + free ASO (8mg/kg) | 1 | 91.9 | 71.0 | 0.8 |
| | 2 | 90.1 | 82.4 | 0.9 |
| | 3 | 91.0 | 87.6 | 1.0 |
| | 4 | 78.0 | 60.2 | 0.8 |
| conjugate (0.2mg/kg Ab) | 1 | 94.9 | 79.4 | 0.6 |
| | 2 | 90.6 | 39.3 | 0.4 |
| | 3 | 94.3 | 83.5 | 0.9 |
| | 4 | 93.0 | 91.2 | 1.0 |
| conjugate (1mg/kg Ab) | 1 | 96.2 | 83.2 | 0.9 |
| | 2 | 84.2 | 72.3 | 0.9 |
| | 3 | 79.4 | 69.3 | 0.9 |
| | 4 | 82.6 | 59.2 | 0.7 |
| | 5 | 91.2 | 77.5 | 0.8 |
| | 6 | 89.7 | 77.3 | 0.9 |
| | 7 | 93.6 | 88.9 | 0.9 |
| | 8 | 93.7 | 77.9 | 0.8 |
| conjugate (5mg/kg Ab) | 1 | 85.2 | 68.1 | 0.8 |
| | 2 | 89.6 | 74.0 | 0.8 |
| | 3 | 89.5 | 74.3 | 0.8 |
| | 4 | 93.4 | 77.3 | 0.8 |
| conjugate (10mg/kg Ab) | 1 | 89.8 | 78.8 | 0.9 |
| | 2 | 89.9 | 80.2 | 0.9 |
| | 3 | 83.1 | 68.7 | 0.8 |
| | 4 | 90.0 | 75.3 | 0.8 |

*FIG. 11 A*

| | Mouse | HLA% | CD22% | CD22/HLA | |
|---|---|---|---|---|---|
| PBS | 1 | 99.0 | 93.1 | 0.9 | * |
| | 2 | 93.0 | 93.0 | 1.0 | * |
| | 3 | 96.4 | 77.5 | 0.8 | * |
| | 4 | 96.6 | 22.9 | 0.4 | * |
| | 5 | 94.5 | 79.8 | 0.8 | * |
| | 6 | 90.1 | 58.9 | 0.7 | * |
| | 7 | 94.5 | 62.8 | 0.7 | * |
| | 8 | 92.0 | 65.5 | 0.7 | * |
| free Ab (1mg/kg) + free ASO (0.8mg/kg) | 1 | 93.6 | 97.2 | 1.0 | * |
| | 2 | 92.7 | 76.1 | 0.8 | * |
| | 3 | 92.7 | 47.4 | 0.5 | * |
| | 4 | 89.0 | 59.3 | 0.7 | * |
| | 5 | 96.5 | 68.6 | 0.7 | * |
| | 6 | 99.4 | 94.6 | 1.0 | * |
| | 7 | 92.1 | 90.3 | 1.0 | * |
| | 8 | 85.8 | 55.2 | 0.6 | * |
| conjugate (0.2mg/kg Ab) | 1 | 90.0 | 95.3 | 1.1 | |
| | 2 | 94.3 | 83.4 | 0.9 | |
| | 3 | 94.2 | 93.9 | 1.0 | |
| | 4 | 94.4 | 84.4 | 0.9 | |
| | 5 | 93.8 | 86.1 | 0.9 | |
| | 6 | 92.0 | 87.8 | 1.0 | |
| | 7 | 96.0 | 94.2 | 1.0 | |
| | 8 | 97.6 | 96.5 | 1.0 | |
| conjugate (1mg/kg Ab) | 1 | 91.6 | 93.5 | 1.0 | |
| | 2 | 93.1 | 93.9 | 1.0 | |
| | 3 | 91.4 | 93.6 | 1.0 | |
| | 4 | 91.1 | 80.3 | 0.9 | |
| | 5 | 94.8 | 89.7 | 0.9 | |
| | 6 | 90.8 | 84.8 | 0.9 | |
| | 7 | 92.6 | 88.0 | 1.0 | |
| | 8 | 86.6 | 76.0 | 0.9 | |

*FIG. 11 B*

|  | Mouse | HLA% | CD22% | CD22/HLA |
|---|---|---|---|---|
| PBS | 1 | 84.3 | 73.7 | 0.9 |
|  | 2 | 75.4 | 73.4 | 1.0 |
|  | 3 | 73.9 | 70.5 | 1.0 |
|  | 4 | 65.6 | 66.9 | 1.0 |
|  | 5 | 88.8 | 88.1 | 1.0 |
|  | 6 | 69.0 | 67.1 | 1.0 |
| free Ab (1mg/kg) + free ASO (0.8mg/kg) | 1 | 87.8 | 78.9 | 0.9 |
|  | 2 | 87.6 | 78.3 | 0.9 |
|  | 3 | 90.9 | 84 | 0.9 |
|  | 4 | 88.8 | 81.9 | 0.9 |
|  | 5 | 82.5 | 76.6 | 0.9 |
|  | 6 | 90.3 | 74.6 | 0.8 |
| conjugate (0.2mg/kg Ab) | 1 | 76.3 | 75.1 | 1.0 |
|  | 2 | 73.2 | 66.6 | 0.9 |
|  | 3 | 94.2 | 88.2 | 0.9 |
|  | 4 | 91.6 | 79.8 | 0.9 |
|  | 5 | 88.6 | 83 | 0.9 |
|  | 6 | 87.6 | 82.5 | 0.9 |
| conjugate (1mg/kg Ab) | 1 | 77.5 | 73.3 | 0.9 |
|  | 2 | 74.5 | 69.8 | 0.9 |
|  | 3 | 80.2 | 73.2 | 0.9 |
|  | 4 | 87.1 | 82.3 | 0.9 |
|  | 5 | 85.6 | 74.7 | 0.9 |
|  | 6 | 87.9 | 79.3 | 0.9 |

ANTISENSE COMPOUNDS AND USES THEREOF

CROSS-REFERENCES TO RELATED APPLICATIONS

This application claims the benefit of priority to U.S. Provisional Application Nos. 62/057,985, filed on Sep. 30, 2014; 62/084,333, filed on Nov. 25, 2014; and 62/113,007, filed on Feb. 6, 2015; the contents of each of which are incorporated by reference in the entirety for all purposes.

STATEMENT AS TO RIGHTS TO INVENTIONS MADE UNDER FEDERALLY SPONSORED RESEARCH AND DEVELOPMENT

This invention was made with government support under UL1 TR000002 awarded by National Institute of Health. The government has certain rights in the invention.

REFERENCE TO A "SEQUENCE LISTING," A TABLE, OR A COMPUTER PROGRAM LISTING APPENDIX SUBMITTED ON A COMPACT DISK

The present application is being filed along with a Sequence Listing in electronic format. The Sequence Listing is provided as a file entitled SEQ_076916-215910US-958724_ST25.txt, created Sep. 30, 2015, which is 52 Kb in size. The information in the electronic format of the sequence listing is incorporated herein by reference in its entirety.

BACKGROUND OF THE INVENTION

Antisense compounds have been used to modulate target nucleic acids. Antisense compounds comprising a variety of chemical modifications and motifs have been reported. In certain instances, such compounds are useful as research tools, diagnostic reagents, and as therapeutic agents. In certain instances antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenylation or prevent formation of the 5'-cap of a pre-mRNA.

MAX dimerization protein 3 (MXD3) transcription factor, a member of the MYC/MAX/MXD family of basic helix-loop-helix proteins, is a therapeutic molecular target in acute lymphoblastic leukaemia. MXD3 is highly expressed in acute lymphoblastic leukaemia and is expressed in normal and malignant B cells.

BRIEF SUMMARY OF THE INVENTION

In certain embodiments, the present disclosure provides compounds comprising modified oligonucleotides conjugated to an anti-CD22 antibody. In certain embodiments, such compounds comprise modified oligonucleotides having a gapmer motif. In certain embodiments, such compounds comprise modified oligonucleotides having a nucleobase sequence complementary to MAX Dimerization Protein 3. In certain embodiments, compounds comprising modified oligonucleotides conjugated to an anti-CD22 antibody are useful for targeting precursor B-cell acute lymphoblastic leukaemia. In certain embodiments, compounds comprising modified oligonucleotides conjugated to an anti-CD22 antibody are useful for targeting leukaemia. In certain embodiments, compounds comprising modified oligonucleotides conjugated to an anti-CD22 antibody are useful for targeting lymphoma. In certain embodiments, compounds comprising modified oligonucleotides conjugated to an anti-CD22 antibody are useful for targeting cells associated with B-cell diseases. In certain embodiments, compounds comprising modified oligonucleotides conjugated to an anti-CD22 antibody are useful for targeting cells associated with autoimmune diseases.

In certain embodiments, conjugation of an anti-CD22 antibody to a modified oligonucleotide complementary to an MXD3 nucleic acid results in targeted delivery of the modified oligonucleotide-anti-CD22 antibody compound to cell or tissue associated with leukemia, lymphoma, or B-cell disease. In certain embodiments, conjugation of an anti-CD22 antibody to a modified oligonucleotide complementary to an MXD3 nucleic acid results in targeted delivery of the modified oligonucleotide-anti-CD22 antibody compound to a leukemia cell. In certain embodiments, conjugation of an anti-CD22 antibody to a modified oligonucleotide complementary to an MXD3 nucleic acid results in targeted delivery of the modified oligonucleotide-anti-CD22 antibody compound to a lymphoma cell. In certain embodiments, conjugation of an anti-CD22 antibody to a modified oligonucleotide complementary to an MXD3 nucleic acid results in targeted delivery of the modified oligonucleotide-anti-CD22 antibody compound to a B-cell. In certain embodiments, a modified oligonucleotide complementary to an MXD3 nucleic acid conjugated to an anti-CD22 antibody is more effective at reducing expression of MXD3 nucleic acid transcript compared to a modified oligonucleotide complementary to MXD3 but lacking the anti-CD22 antibody.

The present disclosure provides the following non-limiting numbered embodiments:

Embodiment 1: A compound comprising a modified oligonucleotide and an anti-CD22 antibody, wherein the modified oligonucleotide consists of 8 to 80 linked nucleosides, and wherein the modified oligonucleotide is at least 85%, 90%, 95%, or 100% complementary to SEQ ID NO: 1.

Embodiment 2: A compound comprising a modified oligonucleotide and an anti-CD22 antibody, wherein the modified oligonucleotide is targeted to a MAX Dimerization Protein 3 nucleic acid.

Embodiment 3: A compound comprising a modified oligonucleotide and an anti-CD22 antibody, wherein the modified oligonucleotide consists of 8 to 80 linked nucleosides complementary within nucleotides 26565-26580, 26618-26633, 26703-26718, 27244-27259, 27255-27270, 31126-31141, 31131-31146, 27058-27073, 27416-27431, 29056-29071, 29268-29283, 29274-29289, or 29752-29767 of SEQ ID NO: 1.

Embodiment 4: A compound comprising a modified oligonucleotide and an anti-CD22 antibody, wherein the modified oligonucleotide consists of 8 to 80 linked nucleosides having a nucleobase sequence comprising any one of SEQ ID NOs: 5, 6, 7, 8, 9, 10, 11, 12, 13, 14, 15, 16, or 17.

Embodiment 5: A compound comprising a modified oligonucleotide and an anti-CD22 antibody, wherein the modified oligonucleotide has a nucleobase sequence comprising any one of SEQ ID NOs: 5, 6, 7, 8, 9, 10, 11, 12, 13, 14, 15, 16, or 17.

Embodiment 6: A compound comprising a modified oligonucleotide and an anti-CD22 antibody, wherein the modified oligonucleotide consists of 10 to 30 linked nucleosides and has a nucleobase sequence comprising at least 8 contiguous nucleobases of any of the nucleobase sequences of SEQ ID NOs: 5, 6, 7, 8, 9, 10, 11, 12, 13, 14, 15, 16, or 17.

Embodiment 7: A compound comprising a modified oligonucleotide and an anti-CD22 antibody, wherein the modified oligonucleotide consists of 10 to 30 linked nucleosides and has a nucleobase sequence comprising at least 9 contiguous nucleobases of any of the nucleobase sequences of SEQ ID NOs: 5, 6, 7, 8, 9, 10, 11, 12, 13, 14, 15, 16, or 17.

Embodiment 8: A compound comprising a modified oligonucleotide and an anti-CD22 antibody, wherein the modified oligonucleotide consists of 10 to 30 linked nucleosides and has a nucleobase sequence comprising at least 10 contiguous nucleobases of any of the nucleobase sequences of SEQ ID NOs: 5, 6, 7, 8, 9, 10, 11, 12, 13, 14, 15, 16, or 17.

Embodiment 9: A compound comprising a modified oligonucleotide and an anti-CD22 antibody, wherein the modified oligonucleotide consists of 10 to 30 linked nucleosides and has a nucleobase sequence comprising at least 11 contiguous nucleobases of any of the nucleobase sequences of SEQ ID NOs: 5, 6, 7, 8, 9, 10, 11, 12, 13, 14, 15, 16, or 17.

Embodiment 10: A compound comprising a modified oligonucleotide and an anti-CD22 antibody, wherein the modified oligonucleotide consists of 10 to 30 linked nucleosides and has a nucleobase sequence comprising at least 12 contiguous nucleobases of any of the nucleobase sequences of SEQ ID NOs: 5, 6, 7, 8, 9, 10, 11, 12, 13, 14, 15, 16, or 17.

Embodiment 11: A compound comprising a modified oligonucleotide and an anti-CD22 antibody, wherein the modified oligonucleotide consists of 10 to 30 linked nucleosides and has a nucleobase sequence comprising the nucleobase sequences of SEQ ID NOs: 5, 6, 7, 8, 9, 10, 11, 12, 13, 14, 15, 16, or 17.

Embodiment 12: A compound comprising a modified oligonucleotide and an anti-CD22 antibody, wherein the modified oligonucleotide consists of the nucleobase sequences of SEQ ID NOs: 5, 6, 7, 8, 9, 10, 11, 12, 13, 14, 15, 16, or 17.

Embodiment 13: A compound comprising a modified oligonucleotide and an anti-CD22 antibody, wherein the modified oligonucleotide has a nucleobase sequence comprising at least an 8 nucleobase portion of any of SEQ ID NOs: 5, 6, 7, 8, 9, 10, 11, 12, 13, 14, 15, 16, or 17.

Embodiment 14: A compound comprising a modified oligonucleotide and an anti-CD22 antibody, wherein the modified oligonucleotide consists of 16 linked nucleosides having a nucleobase sequence consisting of the sequence recited in SEQ ID NOs: 5, 6, 7, 8, 9, 10, 11, 12, 13, 14, 15, 16, or 17, wherein the modified oligonucleotide comprises:
a gap segment consisting of ten linked deoxynucleosides;
a 5' wing segment consisting of three linked nucleosides; and
a 3' wing segment consisting of three linked nucleosides;
wherein the gap segment is positioned between the 5' wing segment and the 3' wing segment; wherein each nucleoside of the 5' wing segment comprises a (S)-cEt sugar modification; wherein each nucleoside of the 3' wing segment comprises a (S)-cEt sugar modification; wherein each internucleoside linkage is a phosphorothioate linkage; and wherein each cytosine is a 5-methylcytosine.

Embodiment 15: The compound of any one of embodiments 1-14, wherein the oligonucleotide is at least 80%, 85%, 90%, 95%, or 100% complementary to SEQ ID NO: 1.

Embodiment 16: The compound of any one of embodiments 1-15, wherein the modified oligonucleotide comprises at least one modified internucleoside linkage, at least one modified sugar, or at least one modified nucleobase.

Embodiment 17: The compound of embodiment 16, wherein the modified internucleoside linkage is a phosphorothioate internucleoside linkage.

Embodiment 18: The compound of embodiment 16, wherein the modified oligonucleotide comprises at least 1 phosphodiester internucleoside linkage.

Embodiment 19: The compound of embodiment 16, wherein the modified oligonucleotide comprises at least 2 phosphodiester internucleoside linkages.

Embodiment 20: The compound of embodiment 16, wherein the modified oligonucleotide comprises at least 3 phosphodiester internucleoside linkages.

Embodiment 21: The compound of embodiment 16, wherein the modified oligonucleotide comprises at least 4 phosphodiester internucleoside linkages.

Embodiment 22: The compound of embodiment 16, wherein the modified oligonucleotide comprises at least 5 phosphodiester internucleoside linkages.

Embodiment 23: The compound of embodiment 16, wherein the modified oligonucleotide comprises at least 6 phosphodiester internucleoside linkages.

Embodiment 24: The compound of embodiment 16, wherein the modified oligonucleotide comprises at least 7 phosphodiester internucleoside linkages.

Embodiment 25: The compound of any of embodiments 18-24, wherein each internucleoside linkage of the modified oligonucleotide is selected from a phosphodiester internucleoside linkage and a phosphorothioate internucleoside linkage.

Embodiment 26: The compound of embodiment 25, wherein each internucleoside linkage of the modified oligonucleotide comprises is a phosphorothioate internucleoside linkage.

Embodiment 27: The compound of any one of embodiments 16-26, wherein the modified sugar is a bicyclic sugar.

Embodiment 28: The compound of embodiment 27, wherein the bicyclic sugar is selected from the group consisting of: 4'-(CH$_2$)—O-2' (LNA); 4'-(CH$_2$)$_2$—O-2' (ENA); and 4'-CH(CH$_3$)—O-2' (cEt).

Embodiment 29: The compound of any one of embodiments 16-28, wherein the modified sugar is 2'-O-methoxyethyl.

Embodiment 30: The compound of any one of embodiments 16-29, wherein the modified nucleobase is a 5-methylcytosine.

Embodiment 31: The compound of any one of embodiments 1-30, wherein the modified oligonucleotide comprises:
(a) a gap segment consisting of linked deoxynucleosides;
(b) a 5' wing segment consisting of linked nucleosides; and
(c) a 3' wing segment consisting of linked nucleosides;
wherein the gap segment is positioned immediately adjacent to and between the 5' wing segment and the 3' wing segment and wherein each nucleoside of each wing segment comprises a modified sugar.

Embodiment 32: The compound of any one of embodiments 1-31, wherein the modified oligonucleotide comprises of nucleosides comprising either a MOE sugar modification, an (S)-cEt sugar modification, or a deoxy modification; wherein each internucleoside linkage is a phosphorothioate linkage; and wherein each cytosine is a 5-methylcytosine.

Embodiment 33: The compound of any one of embodiments 1-32, wherein the modified oligonucleotide is single-stranded.

Embodiment 34: The compound of any one of embodiments 1-32, wherein the modified oligonucleotide is double-stranded Embodiment 35: The compound of any one of embodiments 1-34, wherein the compound comprises ribonucleotides.

Embodiment 36: The compound of any one of embodiments 1-35, wherein the compound comprises deoxyribonucleotides.

Embodiment 37: The compound of any one of embodiments 1-36, wherein the modified oligonucleotide consists of 10 to 30 linked nucleosides.

Embodiment 38: The compound of any one of embodiments 1-36, wherein the modified oligonucleotide consists of 12 to 30 linked nucleosides.

Embodiment 39: The compound of any one of embodiments 1-36, wherein the modified oligonucleotide consists of 15 to 30 linked nucleosides.

Embodiment 40: The compound of any one of embodiments 1-39, wherein the compound comprises a second modified oligonucleotide conjugated to the anti-CD22 antibody.

Embodiment 41: The compound of any one of embodiments 1-40, wherein the compound comprises a third modified oligonucleotide conjugated to the anti-CD22 antibody.

Embodiment 42: The compound of any one of embodiments 1-41, wherein the compound comprises a fourth modified oligonucleotide conjugated to the anti-CD22 antibody.

Embodiment 43: The compound of any one of embodiments 1-41, wherein the compound comprises at least two modified oligonucleotides conjugated to the anti-CD22 antibody.

Embodiment 44: The compound of any one of embodiments 1-41, wherein the compound comprises at least three modified oligonucleotides conjugated to the anti-CD22 antibody.

Embodiment 45: The compound of any one of embodiments 1-41, wherein the compound comprises at least four modified oligonucleotides conjugated to the anti-CD22 antibody.

Embodiment 46: The compound of any one of embodiments 40-45, wherein each modified oligonucleotide has the same nucleobase sequence.

Embodiment 47: The compound of any one of embodiments 40-45, wherein at least two modified oligonucleotides have different nucleobase sequences.

Embodiment 48: The compound of embodiment 47, wherein each modified oligonucleotide is at least 85%, 90%, 95%, or 100% complementary to SEQ ID NO: 1.

Embodiment 49: A compound consisting of ISIS No. 632407, ISIS No. 632407, ISIS No. 632417, ISIS No. 632424, ISIS No. 632460, ISIS No. 632461, ISIS No. 632527, ISIS No. 632528, ISIS No. 632634, ISIS No. 632640, ISIS No. 632669, ISIS No. 632672, ISIS No. 632673 or ISIS No. 632682, and an anti-CD22 antibody.

Embodiment 50: The compound of any of embodiments 1 to 49, wherein the anti-CD22 antibody is linked to the modified oligonucleotide at the 5' end of the modified oligonucleotide.

Embodiment 51: The compound of any of embodiments 1 to 49, wherein the anti-CD22 antibody is linked to the modified oligonucleotide at the 3' end of the modified oligonucleotide.

Embodiment 52: A pharmaceutical composition comprising the compound of any of embodiments 1-51 and at least one pharmaceutically acceptable carrier or diluent.

Embodiment 53: A method of reducing the amount or activity of a MAX Dimerization Protein 3 nucleic acid comprising contacting a cell with the compound of any of embodiments 1 to 52.

Embodiment 54: A method of reducing the amount or activity of a MAX Dimerization Protein 3 protein comprising contacting a cell with the compound of any of embodiments 1 to 52.

Embodiment 55: A method of treating lymphoma, comprising contacting a cell with the compound of any of embodiments 1 to 52.

Embodiment 56: A method of treating leukemia, comprising contacting a cell with the compound of any of embodiments 1 to 52.

Embodiment 57: A method of treating an autoimmune disease, comprising contacting a cell with the compound of any of embodiments 1 to 52.

Embodiment 58: A method of treating a B-cell disease, comprising contacting a cell with the compound of any of embodiments 1 to 52.

Embodiment 59: The method of any of embodiments 53 to 58, wherein the cell is in vitro.

Embodiment 60: The method of any of embodiments 53 to 58, wherein the cell is in an animal.

Embodiment 61: The method of any of embodiments 53 to 58, wherein the animal is a human.

Embodiment 62: The method of any of embodiments 53 to 58, wherein the animal is a non-human primate.

Embodiment 63: The method of any of embodiments 53 to 58, wherein the method comprises contacting the cell with one or more chemotherapy agents.

Embodiment 64: The method of embodiment 63, wherein the chemotherapy agent is vincristine.

Embodiment 65: The method of embodiment 64, wherein the chemotherapy agent is doxorubicin.

Embodiment 66: The method of embodiment 64, wherein the chemotherapy agent is a combination of vincristine and doxorubicin.

Embodiment 67: Use of the compound of any of embodiments 1 to 52 for the treatment of a B-cell disease.

Embodiment 68: Use of the compound of any of embodiments 1 to 52 for the treatment of leukemia.

Embodiment 69: Use of the compound of any of embodiments 1 to 52 for the treatment of lymphoma.

Embodiment 70: Use of the compound of any of embodiments 1 to 52 for the treatment of an autoimmune disease.

Embodiment 71: Use of the compound of any of embodiments 1 to 52 for manufacture of a medicament for the treatment of a B-cell disease.

Embodiment 72: Use of the compound of any of embodiments 1 to 52 for manufacture of a medicament for the treatment of leukemia.

Embodiment 73: Use of the compound of any of embodiments 1 to 52 for manufacture of a medicament for the treatment of lymphoma.

Embodiment 74: Use of the compound of any of embodiments 1 to 52 for manufacture of a medicament for the treatment of an autoimmune disease.

Embodiment 75: A compound comprising one or more modified oligonucleotides and an anti-CD22 antibody, wherein the one or more modified oligonucleotides comprise:
16 linked nucleosides having a nucleobase sequence of the sequence recited in SEQ ID NOs: 5, 6, 7, 8, 9, 10, 11, 12, 13, 14, 15, 16, or 17;
a gap segment consisting of ten linked deoxynucleosides;
a 5' wing segment consisting of three linked nucleosides; and
a 3' wing segment consisting of three linked nucleosides;
wherein the gap segment is positioned between the 5' wing segment and the 3' wing segment; wherein each nucleoside of the 5' wing segment comprises a (S)-cEt sugar modification; wherein each nucleoside of the 3' wing segment comprises a (S)-cEt sugar modification; wherein each internucleoside linkage is a phosphorothioate linkage; and wherein each cytosine is a 5-methylcytosine.

Embodiment 76: The compound of embodiment 75, wherein the one or more modified oligonucleotides consist of:
16 linked nucleosides having a nucleobase sequence of the sequence recited in SEQ ID NOs: 5, 6, 7, 8, 9, 10, 11, 12, 13, 14, 15, 16, or 17;
a gap segment consisting of ten linked deoxynucleosides;
a 5' wing segment consisting of three linked nucleosides; and
a 3' wing segment consisting of three linked nucleosides;
wherein the gap segment is positioned between the 5' wing segment and the 3' wing segment; wherein each nucleoside of the 5' wing segment comprises a (S)-cEt sugar modification; wherein each nucleoside of the 3' wing segment comprises a (S)-cEt sugar modification; wherein each internucleoside linkage is a phosphorothioate linkage; and wherein each cytosine is a 5-methylcytosine.

Embodiment 77: The compound of embodiment 75, wherein the one or more modified oligonucleotides consist of ISIS No. 632407, ISIS No. 632407, ISIS No. 632417, ISIS No. 632424, ISIS No. 632460, ISIS No. 632461, ISIS No. 632527, ISIS No. 632528, ISIS No. 632634, ISIS No. 632640, ISIS No. 632669, ISIS No. 632672, ISIS No. 632673 or ISIS No. 632682.

Embodiment 78: The compound of embodiment 75, wherein the one or more modified oligonucleotides consist of ISIS No. 632461.

Embodiment 79: The compound of any one of embodiments 75-78, wherein the compound comprises the anti-CD22 antibody and 2-4 modified oligonucleotides.

Embodiment 80: The compound of any one of embodiments 75-79, wherein the one or more modified oligonucleotides are conjugated to the anti-CD22 antibody at a 5' end or a 3' end.

Embodiment 81: The compound of any one of embodiments 75-80, wherein the one or more modified oligonucleotides are conjugated to the anti-CD22 antibody through a linker comprising or consisting of an oligoethyleneglycol moiety, a monoethyleneglycol moiety, a diethyleneglycol moiety, a triethyleneglycol moiety, a tetraethyleneglycol moiety, a pentaethyleneglycol moiety, or a hexaethyleneglycol moiety.

Embodiment 82: A method of treating a B-cell disease, comprising contacting a cell with any one of the compounds of embodiments 75-81.

Embodiment 83: The method of embodiment 82, wherein the B-cell disease is leukemia, precursor B-cell acute lymphoblastic leukemia, or lymphoma.

Embodiment 84: The method of embodiment 83, wherein the B-cell disease is a B-cell mediated autoimmune disease.

Embodiment 85: The method of any one of embodiments 81-84, wherein the method comprises contacting the cell with one or more chemotherapy agents.

Embodiment 86: The method of embodiment 85, wherein the one or more chemotherapy agents comprise doxorubicin, vincristine, or a combination of doxorubicin and vincristine.

BRIEF DESCRIPTION OF THE DRAWINGS

FIG. 11A, FIG. 11B, FIG. 11C: HLA and CD22 expression of the cells harvested from leukemia xenograft models. Reh (FIG. 11A) and patient-derived leukemic cells (FIG. 11B and FIG. 11C) engrafted in the mice, respectively, showed high expression of HLA and CD22 as quantified by flow cytometry. * indicates the samples which were fixed for subsequent analyses.

FIG. 12A, FIG. 12B: Blood test results of the mice from the patient-derived leukemia xenograft model. (FIG. 12A) CBC and (FIG. 12B) chemistry panels for the patient-derived leukemia xenograft mice during treatment. One representative mouse from each treatment arm was tested weekly.

DETAILED DESCRIPTION OF THE INVENTION

Figure 1:
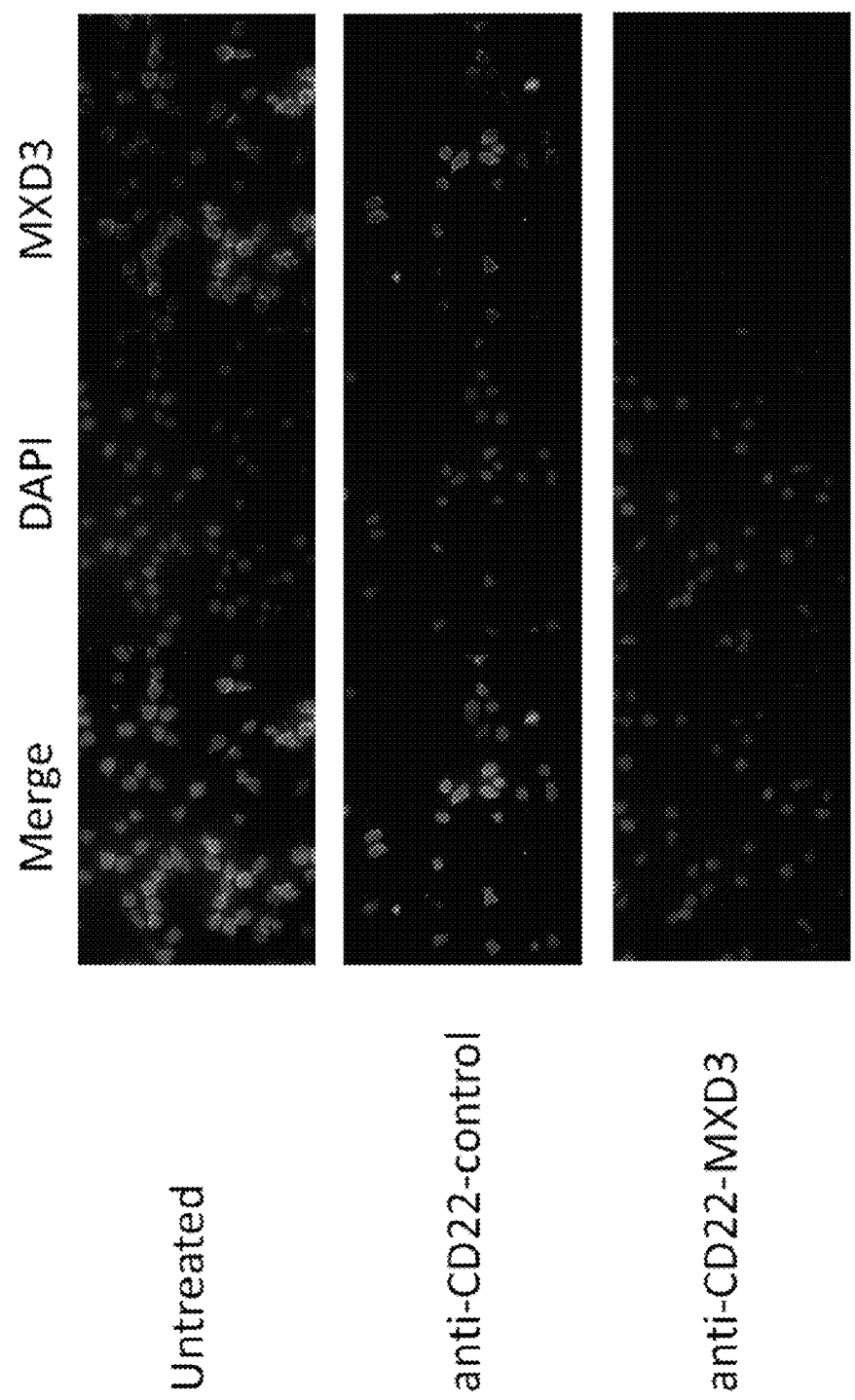
FIG. 1 shows Reh cells stained for MXD3 and with DAPI four hours following treatment with anti-CD22-MXD3 conjugate, anti-CD22-control conjugate, or no treatment.

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

Unless otherwise indicated, the following terms have the following meanings:

As used herein, the term "antibody" means any antigen-binding molecule or molecular complex comprising at least one complementarity determining region (CDR) that specifically binds to or interacts with a particular antigen. The term "antibody" also includes antigen-binding fragments of full antibody molecules.

As used herein, the term "anti-CD22 antibody" means any antigen-binding molecule or molecular complex comprising at least one complementarity determining region (CDR) that specifically binds to or interacts with CD22. The term "anti-CD22 antibody" also includes antigen-binding fragments of full antibody molecules that specifically bind or interact with CD22. In certain embodiments, an anti-CD22 antibody is a monoclonal antibody. In certain embodiments, an anti-CD22 antibody is a polyclonal antibody. In certain embodiments, an anti-CD22 antibody is a humanized antibody. In certain embodiments, an anti-CD22 antibody is a humanized monoclonal antibody. In certain embodiments, an anti-CD22 antibody refers to an antibody having CDRL1-3 and CDRH1-3 sequences identical to the corresponding CDR sequences of antibody JT22.1. In certain embodiments, an anti-CD22 antibody refers to antibody JT22.1. A hybridoma for producing antibody JT22.1 has been deposited under accession no. _____. In certain embodiments, an anti-CD22 antibody refers to an antibody generated by or from mice immunized with a polypeptide including a CD22 transmembrane domain (e.g., encoded by BP 2208-2263 of human CD22) and extracytoplasmic domains 1 and 2 (e.g., encoded by BP 57-867).

As used herein, the term "autoimmune disease" means a disease resulting from an immune response against a self tissue or tissue component. In certain embodiments, autoimmune diseases include, for example, lupus erythematosus.

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "2'-F nucleoside" refers to a nucleoside comprising a sugar comprising fluorine at the 2' position. Unless otherwise indicated, the fluorine in a 2'-F nucleoside is in the ribo position (replacing the OH of a natural ribose).

As used herein, "2'-(ara)-F" refers to a 2'-F substituted nucleoside, wherein the fluoro group is in the arabino position.

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2'bridge.

As used herein, "locked nucleic acid nucleoside" or "LNA" means a nucleoside comprising a bicyclic sugar moiety comprising a 4'-CH$_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "RNA-like nucleoside" means a modified nucleoside that adopts a northern configuration and functions like RNA when incorporated into an oligonucleotide. RNA-like nucleosides include, but are not limited to 3'-endo furanosyl nucleosides and RNA surrogates.

As used herein, "3'-endo-furanosyl nucleoside" means an RNA-like nucleoside that comprises a substituted sugar moiety that has a 3'-endo conformation. 3'-endo-furanosyl nucleosides include, but are not limited to: 2'-MOE, 2'-F, 2'-OMe, LNA, ENA, and cEt nucleosides.

As used herein, "RNA-surrogate nucleoside" means an RNA-like nucleoside that does not comprise a furanosyl. RNA-surrogate nucleosides include, but are not limited to hexitols and cyclopentanes.

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage. Examples of modified oligonucleotides include single-stranded and double-stranded compounds, such as, antisense oligonucleotides, siRNAs, shRNAs, ssRNAs, and occupancy-based compounds.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means a compound comprising two molecules that are covalently linked. In certain embodiments, a conjugate comprises an antibody and a modified oligonucleotide.

As used herein, "conjugate group" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measurable activity" means a measurable activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenylation, addition of 5'-cap), and translation.

As used herein, "target nucleic acid" means a nucleic acid molecule to which an antisense compound is intended to hybridize.

As used herein, "non-target nucleic acid" means a nucleic acid molecule to which hybridization of an antisense compound is not intended or desired. In certain embodiments, antisense compounds do hybridize to a non-target, due to homology between the target (intended) and non-target (un-intended).

As used herein, "mRNA" means an RNA molecule that encodes a protein.

As used herein, "pre-mRNA" means an RNA transcript that has not been fully processed into mRNA. Pre-RNA includes one or more intron.

As used herein, "object RNA" means an RNA molecule other than a target RNA, the amount, activity, splicing, and/or function of which is modulated, either directly or indirectly, by a target nucleic acid. In certain embodiments, a target nucleic acid modulates splicing of an object RNA. In certain such embodiments, an antisense compound modulates the amount or activity of the target nucleic acid, resulting in a change in the splicing of an object RNA and ultimately resulting in a change in the activity or function of the object RNA.

As used herein, "microRNA" means a naturally occurring, small, non-coding RNA that represses gene expression of at least one mRNA. In certain embodiments, a microRNA represses gene expression by binding to a target site within a 3' untranslated region of an mRNA. In certain embodiments, a microRNA has a nucleobase sequence as set forth in miRBase, a database of published microRNA sequences found at http://microrna.sanger.ac.uk/sequences/. In certain embodiments, a microRNA has a nucleobase sequence as set forth in miRBase version 12.0 released September 2008, which is herein incorporated by reference in its entirety.

As used herein, "microRNA mimic" means an oligomeric compound having a sequence that is at least partially identical to that of a microRNA. In certain embodiments, a microRNA mimic comprises the microRNA seed region of a microRNA. In certain embodiments, a microRNA mimic modulates translation of more than one target nucleic acids. In certain embodiments, a microRNA mimic is double-stranded.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "modification motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)—$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=$NR_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)($R_{cc}$)), guanidinyl (—N($R_{bb}$)C(=$NR_{bb}$)N($R_{bb}$)($R_{cc}$)), amidinyl (—C(=$NR_{bb}$)N($R_{bb}$)($R_{cc}$) or —N($R_{bb}$)C(=$NR_{bb}$)($R_{aa}$)), thiol (—$SR_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein, "Intracerebroventricular" or "ICV" means administration into the ventricular system of the brain.

Oligomeric Compounds

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications of one or more nucleoside (including modifications to the sugar moiety and/or the nucleobase) and/or modifications to one or more internucleoside linkage.

a. Certain Modified Nucleosides

In certain embodiments, provided herein are oligomeric compounds comprising or consisting of oligonucleotides comprising at least one modified nucleoside. Such modified nucleosides comprise a modified sugar moeity, a modified nucleobase, or both a modified sugar moiety and a modified nucleobase.

i. Certain Sugar Moieties

In certain embodiments, oligomeric compounds of the invention comprise one or more modified nucleosides comprising a modified sugar moiety. Such oligomeric compounds comprising one or more sugar-modified nucleosides may have desirable properties, such as enhanced nuclease stability or increased binding affinity with a target nucleic acid relative to oligomeric compounds comprising only nucleosides comprising naturally occurring sugar moieties. In certain embodiments, modified sugar moieties are substituted sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more substituent, including but not limited to substituents at the 2' and/or 5' positions. Examples of sugar substituents suitable for the 2'-position, include, but are not limited to: 2'-F, 2'-$OCH_3$ ("OMe" or "O-methyl"), and 2'-O$(CH_2)_2OCH_3$ ("MOE"). In certain embodiments, sugar substituents at the 2' position is selected from allyl, amino, azido, thio, O-allyl, O—$C_1$-$C_{10}$ alkyl, O—$C_1$-$C_{10}$ substituted alkyl; O—$C_1$-$C_{10}$ alkoxy; O—$C_1$-$C_{10}$ substituted alkoxy, $OCF_3$, O$(CH_2)_2SCH_3$, O$(CH_2)_2$—O—N(Rm)(Rn), and O—$CH_2$—C(=O)—N(Rm)(Rn), where each Rm and Rn is, independently, H or substituted or unsubstituted $C_1$-$C_{10}$ alkyl. Examples of sugar substituents at the 5'-position, include, but are not limited to: 5'-methyl(R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, O—$C_1$-$C_{10}$ alkoxy; O—$C_1$-$C_{10}$ substituted alkoxy, SH, CN, OCN, $CF_3$, $OCF_3$, O-alkyl, S-alkyl, N($R_m$)-alkyl; O-alkenyl, S-alkenyl, or N($R_m$)-alkenyl; O-alkynyl, S-alkynyl, N($R_m$)-alkynyl; O-alkylenyl-O-alkyl, alkynyl, alkaryl, aralkyl, O-alkaryl, O-aralkyl, O($CH_2$)$_2$$SCH_3$, O—($CH_2$)$_2$—O—N($R_m$)($R_n$) or O—$CH_2$—C(=O)—N($R_m$)($R_n$), where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy(S-alkyl), halogen, alkyl, aryl, alkenyl and alkynyl.

In certain embodiments, a 2'-substituted nucleoside comprises a 2'-substituent group selected from F, $NH_2$, $N_3$, $OCF_3$, O—$CH_3$, O($CH_2$)$_3$$NH_2$, $CH_2$—CH=$CH_2$, O—$CH_2$—CH=$CH_2$, $OCH_2CH_2OCH_3$, O($CH_2$)$_2$$SCH_3$, O—($CH_2$)$_2$—O—N($R_m$)($R_n$), O($CH_2$)$_2$O($CH_2$)$_2$N($CH_3$)$_2$, and N-substituted acetamide (O—$CH_2$—C(=O)—N($R_m$)($R_n$) where each $R_m$ and $R_n$ is, independently, H, an amino protecting group or substituted or unsubstituted $C_1$-$C_{10}$ alkyl.

In certain embodiments, a 2'-substituted nucleoside comprises a sugar moiety comprising a 2'-substituent group selected from F, $OCF_3$, O—$CH_3$, $OCH_2CH_2OCH_3$, O($CH_2$)$_2$$SCH_3$, O—($CH_2$)$_2$—O—N($CH_3$)$_2$, —O($CH_2$)$_2$O($CH_2$)$_2$N($CH_3$)$_2$, and O—$CH_2$—C(=O)—N(H)$CH_3$.

In certain embodiments, a 2'-substituted nucleoside comprises a sugar moiety comprising a 2'-substituent group selected from F, O—$CH_3$, and $OCH_2CH_2OCH_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C($R_a$)($R_b$)]$_n$—, —[C($R_a$)($R_b$)]$_n$—O—, —C($R_a$$R_b$)—N(R)—O— or, —C($R_a$$R_b$)—O—N(R)—; 4'-$CH_2$-2',4'-($CH_2$)$_2$-2',4'-($CH_2$)$_3$-2',4'-($CH_2$)—O-2' (LNA); 4'-($CH_2$)—S-2; 4'-($CH_2$)$_2$—O-2' (ENA); 4'-CH($CH_3$)—O-2' (cEt) and 4'-CH($CH_2OCH_3$)—O-2', and analogs thereof (see, e.g., U.S. Pat. No. 7,399,845, issued on Jul. 15, 2008); 4'-C($CH_3$)($CH_3$)—O-2' and analogs thereof, (see, e.g., WO2009/006478, published Jan. 8, 2009); 4'-$CH_2$—N($OCH_3$)-2' and analogs thereof (see, e.g., WO2008/150729, published Dec. 11, 2008); 4'-$CH_2$—O—N($CH_3$)-2' (see, e.g., US2004/0171570, published Sep. 2, 2004); 4'-$CH_2$—O—N(R)-2', and 4'-$CH_2$—N(R)—O-2'-, wherein each R is, independently, H, a protecting group, or $C_1$-$C_{12}$ alkyl; 4'-$CH_2$—N(R)—O-2', wherein R is H, $C_1$-$C_{12}$ alkyl, or a protecting group (see, U.S. Pat. No. 7,427,672, issued on Sep. 23, 2008); 4'-$CH_2$—C(H)($CH_3$)-2' (see, e.g., Chattopadhyaya, et al., *J. Org. Chem.*, 2009, 74, 118-134); and 4'-$CH_2$—C(=$CH_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C($R_a$)($R_b$)]$_n$—, —C($R_a$)=C($R_b$)—, —C($R_a$)=N—, —C(=$NR_a$)—, —C(=O)—, —C(=S)—, —O—, —Si($R_a$)$_2$—, —S(=O)$_x$—, and —N($R_a$)—; wherein:
x is 0, 1, or 2;
n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl(C(=O)—H), substituted acyl, CN, sulfonyl(S(=O)$_2$-$J_1$), or sulfoxyl(S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl(C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy(4'-$CH_2$—O-2) BNA, (B) β-D-Methyleneoxy(4'-$CH_2$—O-2') BNA (also referred to as locked nucleic acid or LNA), (C) Ethyleneoxy(4'-($CH_2$)$_2$—O-2') BNA, (D) Aminooxy(4'-$CH_2$—O—N(R)-2') BNA, (E) Oxyamino(4'-$CH_2$—N(R)—O-2') BNA, (F) Methyl(methyleneoxy) (4'-CH($CH_3$)—O-2') BNA (also referred to as constrained ethyl or cEt), (G) methylene-thio(4'-$CH_2$—S-2') BNA, (H) methylene-amino(4'-CH2-N(R)-2') BNA, (I) methyl carbocyclic (4'-$CH_2$—CH($CH_3$)-2') BNA, (J) propylene carbocyclic (4'-($CH_2$)$_3$-2') BNA, and (M) 4'-$CH_2$—O—$CH_2$-2' as depicted below.

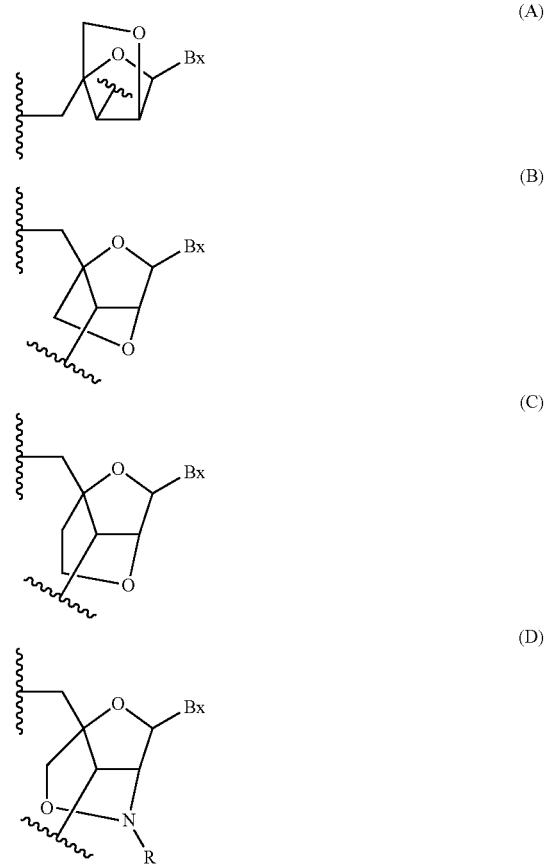

-continued (E)
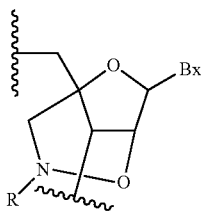

(F)
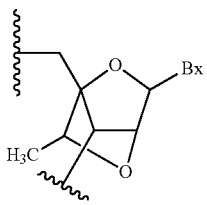

(G)
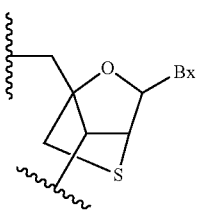

(H)
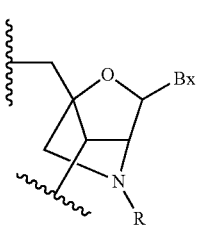

(I)
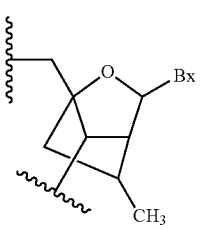

(M)
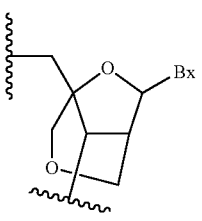

(J)
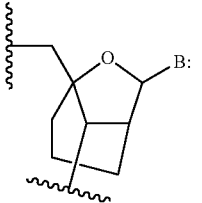

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy(4'-$CH_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

VII

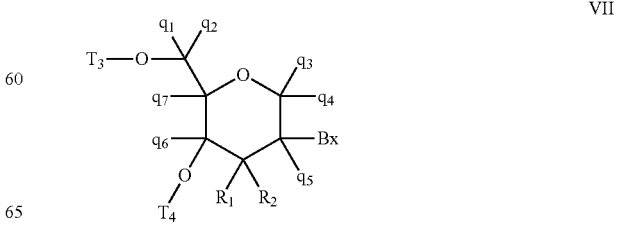

wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclic and tricyclic sugar and sugar surrogate ring systems are known in the art that can be used to modify nucleosides (see, e.g., review article: Leumann, J. C, *Bioorganic & Medicinal Chemistry*, 2002, 10, 841-854).

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166, 315; 5,185,444; and 5,034,506). As used here, the term "morpholino" means a sugar surrogate having the following structure:

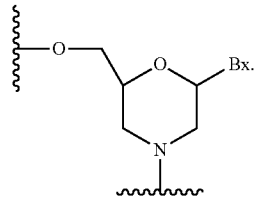

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

ii. Certain Modified Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deazaadenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134, 066; 5,175,273; 5,367,066; 5,432,272; 5,457,187; 5,459, 255; 5,484,908; 5,502,177; 5,525,711; 5,552,540; 5,587, 469; 5,594,121; 5,596,091; 5,614,617; 5,645,985; 5,681, 941; 5,750,692; 5,763,588; 5,830,653 and 6,005,096, certain of which are commonly owned with the instant application, and each of which is herein incorporated by reference in its entirety.

b. Certain Internucleoside Linkages

In certain embodiments, nucleosides may be linked together using any internucleoside linkage to form oligonucleotides. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

i. 3'-Endo Modifications

In one aspect of the present disclosure, oligomeric compounds include nucleosides synthetically modified to induce a 3'-endo sugar conformation. A nucleoside can incorporate synthetic modifications of the heterocyclic base moiety, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement of RNA interference which is supported in part by the fact that duplexes composed of 2'-deoxy-2'-F-nucleosides appear efficient in triggering RNAi response in the *C. elegans* system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric compounds having one or more nucleosides modified in such a way as to favor a C3'-endo type conformation.

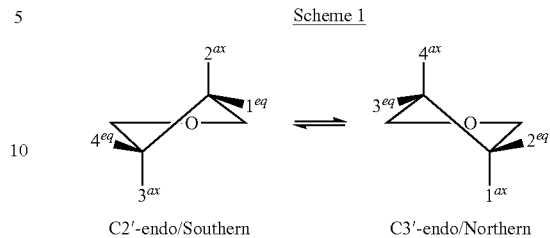

Scheme 1

C2'-endo/Southern    C3'-endo/Northern

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element, as exemplified in Example 35, below (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Some modifications actually lock the conformational geometry by formation of a bicyclic sugar moiety e.g. locked nucleic acid (LNA, Singh et al, Chem. Commun. (1998), 4, 455-456), and ethylene bridged nucleic acids (ENA, Morita et al, Bioorganic & Medicinal Chemistry Letters (2002), 12, 73-76.)

c. Certain Motifs

In certain embodiments, oligomeric compounds comprise or consist of oligonucleotides. In certain embodiments, such oligonucleotides comprise one or more chemical modification. In certain embodiments, chemically modified oligonucleotides comprise one or more modified sugars. In certain embodiments, chemically modified oligonucleotides comprise one or more modified nucleobases. In certain embodiments, chemically modified oligonucleotides comprise one or more modified internucleoside linkages. In certain embodiments, the chemical modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

i. Certain Sugar Motifs

In certain embodiments, oligonucleotides comprise one or more type of modified sugar moieties and/or naturally occurring sugar moieties arranged along an oligonucleotide or region thereof in a defined pattern or sugar motif. Such sugar motifs include but are not limited to any of the sugar modifications discussed herein.

In certain embodiments, the oligonucleotides comprise or consist of a region having a gapmer sugar motif, which comprises two external regions or "wings" and a central or internal region or "gap." The three regions of a gapmer sugar motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric sugar gapmer). In certain embodiments, the sugar motifs of the 5'-wing differs from the sugar motif of the 3'-wing (asymmetric sugar gapmer).

ii. Certain Nucleobase Modification Motifs

In certain embodiments, oligonucleotides comprise chemical modifications to nucleobases arranged along the oligonucleotide or region thereof in a defined pattern or nucleobases modification motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, oligonucleotides comprise one or more nucleosides comprising a modified nucleobase. In certain embodiments, oligonucleotides having a gapmer sugar motif comprise a nucleoside comprising a modified nucleobase. In certain such embodiments, one nucleoside comprising a modified nucleobases is in the central gap of an oligonucleotide having a gapmer sugar motif. In certain embodiments, the sugar is an unmodified 2'deoxynucleoside. In certain embodiments, the modified nucleobase is selected from: a 2-thio pyrimidine and a 5-propyne pyrimidine In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

iii. Certain Nucleoside Motifs

In certain embodiments, oligonucleotides comprise nucleosides comprising modified sugar moieties and/or nucleosides comprising modified nucleobases. Such motifs can be described by their sugar motif and their nucleobase motif separately or by their nucleoside motif, which provides positions or patterns of modified nucleosides (whether modified sugar, nucleobase, or both sugar and nucleobase) in an oligonucleotide.

In certain embodiments, the oligonucleotides comprise or consist of a region having a gapmer nucleoside motif, which comprises two external regions or "wings" and a central or internal region or "gap." The three regions of a gapmer nucleoside motif (the 5'-wing, the gap, and the 3'-wing) form a contiguous sequence of nucleosides wherein at least some of the sugar moieties and/or nucleobases of the nucleosides of each of the wings differ from at least some of the sugar moieties and/or nucleobase of the nucleosides of the gap. Specifically, at least the nucleosides of each wing that are closest to the gap (the 3'-most nucleoside of the 5'-wing and the 5'-most nucleoside of the 3'-wing) differ from the neighboring gap nucleosides, thus defining the boundary between the wings and the gap. In certain embodiments, the nucleosides within the gap are the same as one another. In certain embodiments, the gap includes one or more nucleoside that differs from one or more other nucleosides of the gap. In certain embodiments, the nucleoside motifs of the two wings are the same as one another (symmetric gapmer). In certain embodiments, the nucleoside motifs of the 5'-wing differs from the nucleoside motif of the 3'-wing (asymmetric gapmer).

d. Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

e. Certain Oligonucleotides

In certain embodiments, oligonucleotides of the present invention are characterized by their modification motif and overall length. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

f. Certain Compounds Comprising a Modified Oligonucleotide and an Anti-CD22 Antibody In certain embodiments, the present disclosure provides compounds comprising a modified oligonucleotide complementary to MAX dimerization protein 3 and an anti-CD22 antibody. MAX dimerization protein 3 (MXD3) transcription factor, a member of the MYC/MAX/MXD family of basic helix-loop-helix proteins, is a therapeutic molecular target in acute lymphoblastic leukaemia. MXD3 is highly expressed in acute lymphoblastic leukaemia and is expressed in normal and malignant B cells. In certain embodiments, reducing the expression of MXD3 induces apoptosis in leukemia cells, B-cells, or lymphoma cells. In certain embodiments, contacting a cell with a modified oligonucleotide complementary to an MXD3 nucleic acid reduces the expression of MXD3 nucleic acid transcript. In certain embodiments, contacting a cell with a modified oligonucleotide complementary to an MXD3 nucleic acid reduces the expression of MXD3 protein.

In certain embodiments, conjugation of an anti-CD22 antibody to a modified oligonucleotide complementary to an MXD3 nucleic acid results in targeted delivery of the modified oligonucleotide-anti-CD22 antibody compound to cell or tissue associated with leukemia, lymphoma, or B-cell disease. In certain embodiments, conjugation of an anti-CD22 antibody to a modified oligonucleotide complementary to an MXD3 nucleic acid results in targeted delivery of the modified oligonucleotide-anti-CD22 antibody compound to a leukemia cell. In certain embodiments, conjugation of an anti-CD22 antibody to a modified oligonucleotide complementary to an MXD3 nucleic acid results in targeted delivery of the modified oligonucleotide-anti-CD22 antibody compound to a lymphoma cell. In certain embodiments, conjugation of an anti-CD22 antibody to a modified oligonucleotide complementary to an MXD3 nucleic acid results in targeted delivery of the modified oligonucleotide-anti-CD22 antibody compound to a B-cell. In certain embodiments, a modified oligonucleotide complementary to an MXD3 nucleic acid conjugated to an anti-CD22 antibody is more effective at reducing expression of MXD3 nucleic acid transcript compared to a modified oligonucleotide complementary to MXD3 but lacking the anti-CD22 antibody.

In certain embodiments, one or more oligonucleotides complementary to MXD3 are conjugated to an anti-CD22 antibody. In certain embodiments, two oligonucleotides complementary to MXD3 are conjugated to an anti-CD22 antibody. In certain embodiments, three oligonucleotides complementary to MXD3 are conjugated to an anti-CD22 antibody. In certain embodiments, four oligonucleotides complementary to MXD3 are conjugated to an anti-CD22 antibody. In certain embodiments, five oligonucleotides complementary to MXD3 are conjugated to an anti-CD22 antibody. In certain embodiments, six oligonucleotides complementary to MXD3 are conjugated to an anti-CD22 antibody.

In certain embodiments, two or more oligonucleotides complementary to MXD3 are conjugated to an anti-CD22 antibody and each oligonucleotide has the same nucleobase sequence. In certain embodiments, three or more oligonucleotides complementary to MXD3 are conjugated to an anti-CD22 antibody and each oligonucleotide has the same nucleobase sequence. In certain embodiments, four or more oligonucleotides complementary to MXD3 are conjugated to an anti-CD22 antibody and each oligonucleotide has the same nucleobase sequence.

In certain embodiments, two or more oligonucleotides complementary to MXD3 are conjugated to an anti-CD22 antibody and each oligonucleotide targets a different portion of an MXD3 nucleic acid. In certain embodiments, three or more oligonucleotides complementary to MXD3 are conjugated to an anti-CD22 antibody and each oligonucleotide targets a different portion of an MXD3 nucleic acid. In certain embodiments, four or more oligonucleotides complementary to MXD3 are conjugated to an anti-CD22 antibody and each oligonucleotide targets a different portion of an MXD3 nucleic acid.

In certain embodiments, two or more oligonucleotides complementary to MXD3 are conjugated to an anti-CD22 antibody and each oligonucleotide has a different nucleobase sequence. In certain embodiments, three or more oligonucleotides complementary to MXD3 are conjugated to an anti-CD22 antibody and each oligonucleotide has a different nucleobase sequence. In certain embodiments, four or more oligonucleotides complementary to MXD3 are conjugated to an anti-CD22 antibody and each oligonucleotide has a different nucleobase sequence.

In certain embodiments, oligonucleotides complementary to MXD3 are non-covalently conjugated to an anti-CD22 antibody. For example, in certain embodiments, an oligonucleotide antibody complex is formed between one or more oligonucleotides complementary to MXD3 and an anti-CD22 antibody. In certain embodiments, an anti-CD22 antibody oligonucleotide complex allows for targeted delivery of the oligonucleotide-anti-CD22 antibody complex to cell or tissue associated with leukemia, lymphoma, or B-cell disease.

g. Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3'end of an oligomeric compound, but before one or more terminal group nucleosides. In certain embodiments, conjugate groups are placed within a terminal group.

In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the motifs discussed above. Thus, for example, an oligomeric compound comprising an oligonucleotide having region of alternating nucleosides may comprise a terminal group.

In certain embodiments, a compound comprises an antisense oligonucleotide conjugated to an antibody. In certain embodiments, a compound comprises an antisense oligonucleotide conjugated to an antibody via 1,3-dipolar cycloaddition. In certain embodiments, a compound comprises an antisense oligonucleotide conjugated to an antibody via click chemistry, for example, a reaction between an azide and a cyclooctyne. In certain embodiments, a compound comprises an antisense oligonucleotide conjugated to an antibody via click chemistry, for example, wherein the antisense oligonucleotide is functionalized with a cyclooctyne and then conjugated to an antibody functionalized with one or more azides. In certain embodiments, a compound comprises an antisense oligonucleotide conjugated to an antibody via click chemistry, for example, wherein the antisense oligonucleotide is functionalized with an azide and then conjugated to an antibody functionalized with one or more cyclooctynes. In certain embodiments, a compound comprises an antisense oligonucleotide conjugated to an antibody via copper-free click chemistry.

B. Antisense Compounds

In certain embodiments, oligomeric compounds provided herein are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

a. Certain Antisense Activities and Mechanisms

In certain antisense activities, hybridization of an antisense compound results in recruitment of a protein that cleaves of the target nucleic acid. For example, certain antisense compounds result in RNase H mediated cleavage of target nucleic acid. RNase H is a cellular endonuclease that cleaves the RNA strand of an RNA:DNA duplex. The "DNA" in such an RNA:DNA duplex, need not be unmodified DNA. In certain embodiments, the invention provides antisense compounds that are sufficiently "DNA-like" to elicit RNase H activity. Such DNA-like antisense compounds include, but are not limited to gapmers having unmodified deoxyfuronose sugar moieties in the nucleosides of the gap and modified sugar moieties in the nucleosides of the wings.

Antisense activities may be observed directly or indirectly. In certain embodiments, observation or detection of an antisense activity involves observation or detection of a change in an amount of a target nucleic acid or protein encoded by such target nucleic acid; a change in the ratio of splice variants of a nucleic acid or protein; and/or a phenotypic change in a cell or animal.

In certain embodiments, compounds comprising oligonucleotides having a gapmer nucleoside motif described herein have desirable properties compared to non-gapmer oligonucleotides or to gapmers having other motifs. In certain circumstances, it is desirable to identify motifs resulting in a favorable combination of potent antisense activity and relatively low toxicity. In certain embodiments, compounds of the present invention have a favorable therapeutic index (measure of activity divided by measure of toxicity).

Mismatches to the Target Nucleic Acid

In certain embodiments, selective antisense compounds comprise one or more mismatched nucleobases relative to the target nucleic acid. In certain such embodiments, antisense activity against the target is reduced by such mismatch, but activity against the non-target is reduced by a greater amount. Thus, in certain embodiments selectivity is improved. Any nucleobase other than the differentiating nucleobase is suitable for a mismatch. In certain embodiments, however, the mismatch is specifically positioned within the gap of an oligonucleotide having a gapmer motif. In certain embodiments, a mismatch relative to the target nucleic acid is at positions 1, 2, 3, 4, 5, 6, 7, or 8 from the 5'-end of the gap region. In certain embodiments, a mismatch relative to the target nucleic acid is at positions 9, 8, 7, 6, 5, 4, 3, 2, 1 of the antisense compounds from the 3'-end of the gap region. In certain embodiments, a mismatch relative to the target nucleid acid is at positions 1, 2, 3, or 4 of the antisense compounds from the 5'-end of the wing region. In certain embodiments, a mismatch relative to the target nucleid acid is at positions 4, 3, 2, or 1 of the antisense compounds from the 3'-end of the wing region.

i. Self Complementary Regions

In certain embodiments, selective antisense compounds comprise a region that is not complementary to the target. In certain embodiments, such region is complementary to another region of the antisense compound. Such regions are referred to herein as self-complementary regions. For example, in certain embodiments, an antisense compound has a first region at one end that is complementary to a second region at the other end. In certain embodiments, one of the first and second regions is complementary to the target nucleic acid. Unless the target nucleic acid also includes a self-complementary region, the other of the first and second region of the antisense compound will not be complementary to the target nucleic acid. For illustrative purposes, certain antisense compounds have the following nucleobase motif:

ABCXXXXXXXXXC'B'A';
ABCXXXXXXXX(X/C')(X/B')(X/A');
(X/A)(X/B)(X/C)XXXXXXXXXC'B'A' where each of A, B, and C are any nucleobase; A', B', and C' are the complementary bases to A, B, and C, respectively; each X is a nucleobase complementary to the target nucleic acid; and two letters in parentheses (e.g., (X/C')) indicates that the nucleobase is complementary to the target nucleic acid and to the designated nucleoside within the antisense oligonucleotide.

Without being bound to any mechanism, in certain embodiments, such antisense compounds are expected to form self-structure, which is disrupted upon contact with a target nucleic acid. Contact with a non-target nucleic acid is expected to disrupt the self-structure to a lesser degree, thus increasing selectivity compared to the same antisense compound lacking the self-complementary regions.

ii. Combinations of Features

Though it is clear to one of skill in the art, the above motifs and other elements for increasing selectivity may be used alone or in combination. For example, a single antisense compound may include any one, two, three, or more of: self-complementary regions, a mismatch relative to the target nucleic acid, a short nucleoside gap, an interrupted gap, and specific placement of the selective nucleoside.

C. Certain Target Nucleic Acids

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-microRNA and mature microRNA), a ribosomal RNA, and promoter directed RNA. In certain embodiments, the target nucleic acid encodes a protein. In certain such embodiments, the target nucleic acid is selected from: an mRNA and a pre-mRNA, including intronic, exonic and untranslated regions. In certain embodiments, oligomeric compounds are at least partially complementary to more than one target nucleic acid. For example, antisense compounds of the present invention may mimic microRNAs, which typically bind to multiple targets.

In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target nucleic acid is selected from among non-coding RNA, including exonic regions of pre-mRNA. In certain embodiments, the target nucleic acid is a ribosomal RNA (rRNA). In certain embodiments, the target nucleic acid is a non-coding RNA associated with splicing of other pre-mRNAs. In certain embodiments, the target nucleic acid is a nuclear-retained non-coding RNA.

In certain embodiments, antisense compounds described herein are complementary to a target nucleic acid comprising a single-nucleotide polymorphism. In certain such embodiments, the antisense compound is capable of modulating expression of one allele of the single-nucleotide polymorphism-containing-target nucleic acid to a greater or lesser extent than it modulates another allele. In certain embodiments an antisense compound hybridizes to a single-nucleotide polymorphism-containing-target nucleic acid at the single-nucleotide polymorphism site.

D. Certain Pharmaceutical Compositions

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

E. Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, compounds and compositions are delivered to the CNS. In certain embodiments, compounds and compositions are delivered to the cerebrospinal fluid. In certain embodiments, compounds and compositions are administered to the brain parenchyma. In certain embodiments, compounds and compositions are delivered to an animal by intrathecal administration, or intracerebroventricular administration. Broad distribution of compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

Therefore, in certain embodiments, delivery of a compound or composition described herein can affect the pharmacokinetic profile of the compound or composition. In certain embodiments, injection of a compound or composition described herein, to a targeted tissue improves the pharmacokinetic profile of the compound or composition as compared to infusion of the compound or composition. In a certain embodiment, the injection of a compound or composition improves potency compared to broad diffusion, requiring less of the compound or composition to achieve similar pharmacology. In certain embodiments, similar pharmacology refers to the amount of time that a target mRNA and/or target protein is down-regulated (e.g. duration of action). In certain embodiments, methods of specifically localizing a pharmaceutical agent, such as by bolus injection, decreases median effective concentration (EC50) by a factor of about 50 (e.g. 50 fold less concentration in tissue is required to achieve the same or similar pharmacodynamic effect). In certain embodiments, methods of specifically localizing a pharmaceutical agent, such as by bolus injection, decreases median effective concentration (EC50) by a factor of 20, 25, 30, 35, 40, 45 or 50. In certain embodiments the pharmaceutical agent in an antisense compound as further described herein. In certain embodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

In certain embodiments, an antisense oligonucleotide is delivered by injection or infusion once every month, every two months, every 90 days, every 3 months, every 6 months, twice a year or once a year.

F. Certain Combination Therapies

In certain embodiments, one or more pharmaceutical compositions are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, one or more pharmaceutical compositions and one or more other pharmaceutical agents are administered at the same time. In certain embodiments, one or more pharmaceutical compositions and one or more other pharmaceutical agents are administered at different times. In certain embodiments, one or more pharmaceutical compositions and one or more other pharmaceutical agents are prepared together in a single formulation. In certain embodiments, one or more pharmaceutical compositions and one or more other pharmaceutical agents are prepared separately.

In certain embodiments, pharmaceutical agents that may be co-administered with a pharmaceutical composition of include antipsychotic agents, such as, e.g., haloperidol, chlorpromazine, clozapine, quetapine, and olanzapine; anti-depressant agents, such as, e.g., fluoxetine, sertraline hydrochloride, venlafaxine and nortriptyline; tranquilizing agents such as, e.g., benzodiazepines, clonazepam, paroxetine, venlafaxin, and beta-blockers; mood-stabilizing agents such as, e.g., lithium, valproate, lamotrigine, and carbamazepine; paralytic agents such as, e.g., Botulinum toxin; and/or other experimental agents including, but not limited to, tetrabenazine (Xenazine), creatine, conezyme Q10, trehalose, docosahexanoic acids, ACR16, ethyl-EPA, atomoxetine, citalopram, dimebon, memantine, sodium phenylbutyrate, ramelteon, ursodiol, zyprexa, xenasine, tiapride, riluzole, amantadine, [123I]MNI-420, atomoxetine, tetrabenazine, digoxin, detromethorphan, warfarin, alprozam, ketoconazole, omeprazole, and minocycline.

In certain embodiments, pharmaceutical agents that may be co-administered with a pharmaceutical composition disclosed herein include chemotherapy agents. For example, in certain embodiments, chemotherapy agents include vincristine and/or doxorubicin. In certain embodiments, a compound comprising a modified oligonucleotide having a nucleobase sequence comprising any one of SEQ ID NOs: 5, 6, 7, 8, 9, 10, 11, 12, 13, 14, 15, 16, or 17 and an anti-CD22 antibody is administered to a subject in need thereof in combination with one or more chemotherapy agents. In certain embodiments, a compound comprising a modified oligonucleotide having a nucleobase sequence comprising any one of SEQ ID NOs: 5, 6, 7, 8, 9, 10, 11, 12, 13, 14, 15, 16, or 17 and an anti-CD22 antibody is administered to a subject in need thereof in combination with vincristine. In certain embodiments, a compound comprising a modified oligonucleotide having a nucleobase sequence comprising any one of SEQ ID NOs: 5, 6, 7, 8, 9, 10, 11, 12, 13, 14, 15, 16, or 17 and an anti-CD22 antibody is administered to a subject in need thereof in combination with doxorubicin. In certain embodiments, a compound comprising a modified oligonucleotide having a nucleobase sequence comprising any one of SEQ ID NOs: 5, 6, 7, 8, 9, 10, 11, 12, 13, 14, 15, 16, or 17 and an anti-CD22 antibody is administered to a subject in need thereof in combination with vincristine and doxorubicin.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine(methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1

Screening and Selection of Antisense Oligonucleotides Targeting MXD3

Several hundred antisense oligonucleotides that target human MAX Dimerization Protein 3 (MXD3), GENBANK accession number NT_023133.13 truncated 21540000 to 21577000, SEQ ID NO: 1, were synthesized using standard solid phase oligonucleotide synthetic methods. They are chimeric oligonucleotides ("gapmers") 16 nucleotides in length, composed of a central "gap" region consisting of 10

2'-deoxynucleotides, which is flanked on both sides (5' and 3') by three-nucleotide "wings". The wings are composed of 4'-CH(CH$_3$)—O-2' modified nucleotides, also known as constrained ethyl or (S)-cEt nucleotides. The internucleoside (backbone) linkages are phosphorothioate throughout the oligonucleotides. All cytosine residues are 5-methylcytosines. The sequences of selected MXD3 targeting antisense oligonucleotides and their start and stop sites along GENBANK accession number NT_023133.13 truncated 21540000 to 21577000 are shown in Table 1 below.

days following the final oligonucleotide administration, the mice were sacrificed and plasma transaminase levels, body weights, and organ weights were evaluated relative to the PBS treated group. Based on the results, the oligonucleotides were ranked from most favorable (#1) to least favorable (#13), as shown in Table 2. Isis numbers 632417, 632461, and 632640 had the most favorable tolerability rankings and were selected as leads. Isis No. 632461 targets human, mouse, and monkey MXD3 sequences with no mismatches and was chosen for use in further studies.

TABLE 1

Effect of antisense oligonucleotides targeting MXD3 in vitro

| Isis No. | Sequence (5' to 3') | Start site | Stop site | MXD3 mRNA at 10 µM oligonucleotide (% control) | IC$_{50}$ (µM) | SEQ ID NO: |
|---|---|---|---|---|---|---|
| 632407 | CATCCACCCACGCCGG | 26565 | 26580 | 60.5 | 1.64 | 5 |
| 632417 | GGCCCTGGAGCGAACC | 26618 | 26633 | 38.3 | 7.05 | 6 |
| 632424 | AGCCGCAGCCCACCCT | 26703 | 26718 | 94.4 | 1.64 | 7 |
| 632460 | ATAACCATGCTCGGCC | 27244 | 27259 | 59.0 | 2.95 | 8 |
| 632461 | CACAGGGACGCATAAC | 27255 | 27270 | 59.8 | 8.99 | 9 |
| 632527 | CATCATAGCCAGGCGC | 31126 | 31141 | 76.5 | 9.23 | 10 |
| 632528 | AGGAACATCATAGCCA | 31131 | 31146 | 63.6 | 5.89 | 11 |
| 632634 | GGATTACTGTCCTAGG | 27058 | 27073 | 47.4 | 5.71 | 12 |
| 632640 | CAAGCAACAAGTGGGC | 27416 | 27431 | 65.6 | 0.38 | 13 |
| 632669 | TAAACACTTGTCAGAG | 29056 | 29071 | 34.0 | 9.05 | 14 |
| 632672 | ATCCATCCGAGAACCA | 29268 | 29283 | 50.3 | 4.76 | 15 |
| 632673 | CACATCATCCATCCGA | 29274 | 29289 | 27.5 | 5.58 | 16 |
| 632682 | GTCATTCAACAAGAAG | 29752 | 29767 | 28.4 | 5.61 | 17 |

The antisense oligonucleotides were analyzed for their effects on target mRNA levels. K-562 cells were plated at a density of 50,000 cells per well in 96-well plates and were electroporated with 10 µM oligonucleotide or with no oligonucleotide for untreated controls. After approximately 24 hours, RNA was isolated from the cells, and MXD3 mRNA levels were measured by quantitative real-time PCR using primer probe set RTS4263 (forward: 5'-TTTGTTGCAC-CGTGTCAGTTACT-3', SEQ ID NO: 2; reverse: 5'-TGGC-CAAGGGTTCCATGT-3', SEQ ID NO: 3; probe: 5'-CT-GCAGCCGCTTGCTCCGG-3', SEQ ID NO: 4). MXD3 mRNA levels were adjusted according to total RNA content, as measured by RIBOGREEN®. Results for selected oligonucleotides are presented as average percent MXD3 mRNA level, relative to untreated control cells, in Table 1.

A subset of the MXD3 targeting antisense oligonucleotides were selected for dose response analysis in K-562 cells. Cells were electroporated with 0, 2.19, 8.75, or 35.0 µM antisense oligonucleotide and analyzed as described above. Results for selected oligonucleotides are presented as approximate IC$_{50}$ values in Table 1.

Selected antisense oligonucleotides were then tested for tolerability in vivo. Six week old, male BALB/c mice were injected subcutaneously twice per week for three weeks with 50 mg/kg of an antisense oligonucleotide listed in Table 1 or with PBS. Each treatment group consisted of 4 animals. Two

TABLE 2

Tolerability rankings of antisense oligonucleotides targeting MXD3 in vivo

| Isis No. | Ranking | SEQ ID NO: |
|---|---|---|
| 632407 | 12 | 5 |
| 632417 | 1 | 6 |
| 632424 | 9 | 7 |
| 632460 | 13 | 8 |
| 632461 | 2 | 9 |
| 632527 | 8 | 10 |
| 632528 | 5 | 11 |
| 632634 | 10 | 12 |
| 632640 | 3 | 13 |
| 632669 | 4 | 14 |
| 632672 | 6 | 15 |
| 632673 | 7 | 16 |
| 632682 | 11 | 17 |

Example 2

Synthesis of Antibody-Antisense Oligonucleotide Conjugates

Antibody-antisense oligonucleotide conjugates were made using Isis No. 632461 (see Table 1) and Isis No. 141923, a negative control oligonucleotide that does not target MXD3. The sequence of Isis No. 141923 is 5'-CCT-TCCCTGAAGGTTCCTCC-3' (SEQ ID NO: 18), and it is a 5-10-5 MOE gapmer, wherein the gap region consists of 10 2'-deoxynucleotides, and the wings are composed of 2'-methoxyethyl modified nucleotides, also known as MOE nucleotides. The internucleoside linkages are phosphorothioate throughout the oligonucleotide, and all cytosine residues are 5-methylcytosines. The 5'-end of each oligonucleotide was modified to comprise a cyclooctyne for subsequent click chemistry conjugation to an azide-labeled antibody via 1,3-dipolar cycloaddition. The 5'-DBCO-TEG phosphoramidite (Glen Research, Sterling, Va.) was coupled to the 5'-end of each oligonucleotide using standard solid phase methods to form a phosphodiester linkage between the oligonucleotide and the 5'-DBCO-TEG moiety. Ammonia deprotection was completed at room temperature for a minimum of 48 hours. The cyclooctyne modified oligonucleotides were renamed Isis No. 691563 (derived from Isis No. 632461) and Isis No. 693375 (derived from Isis No. 141923).

Anti-CD22 antibodies were prepared, then incubated in PBS for 3 hours at 4° C. with 1:10 or 1:100 N-hydroxysuccinimide-Azide (Pierce, Rockford, Ill.) dissolved in DMSO. Excess azide was removed using a desalting column (Pierce, catalog #89882). The azide-labeled antibodies were then incubated 1:10 or 1:20 with Isis No. 691563 or 693375 for 30 minutes at 37° C. to form the antibody-antisense oligonucleotide conjugates. Excess oligonucleotide was removed using the same desalting column used to remove excess azide. Herein, "anti-CD22-MXD3" refers to a conjugate comprising a CD22 antibody and Isis No. 691563 that targets MXD3, and "anti-CD22-control" refers to a conjugate comprising a CD22 antibody and Isis No. 693375, a control oligonucleotide.

Example 3

Inhibition of Target Expression by Antibody-Antisense Oligonucleotide Conjugates In Vitro The human cell line Reh (B-cell type acute lymphocytic leukemia cells) was seeded right before treatment in 48-well plates in complete Reh growth media. Cells were incubated for 4 hours with anti-CD22-MXD3, anti-CD22-control, or received no treatment, then the media was replaced with fresh complete Reh media containing no conjugates. Based on an estimation that each conjugate contained one antibody molecule and four oligonucleotides, conjugate amounts were calculated to result in a final oligonucleotide concentration of 2 μM. Target protein expression was analyzed by immunohistochemistry at 4, 8, 24, 48, and 72 hours following the start of treatment. Cells were fixed in formalin for 10 minutes and MXD3 protein expression was detected by anti-MXD3 (Antibodies Inc., Davis, catalog #75-250) and Alexa 488-Goat anti-mouse secondary antibody (Invitrogen, catalog # A11001), and the cells were stained with DAPI. Alexa 488 fluorescence was quantified using Image J software. The results are shown in Table 3 and FIG. 1. Table 3 shows the mean fluorescence intensity (MFI) of the cells in one representative image. FIG. 1 shows representative cell images at the 4 hour time point. The results in Table 3 and FIG. 1 show that the anti-CD22-MXD3 conjugate inhibited MXD3 protein expression in Reh cells.

TABLE 3

MXD3 protein expression in vitro

| Conjugate | Time point (hours) | MFI |
|---|---|---|
| Untreated | 4 | 321.0 |
| anti-CD22-control | 4 | 379.3 |
| anti-CD22-MXD3 | 4 | 114.1 |
| Untreated | 8 | 237.6 |
| anti-CD22-control | 8 | 270.4 |
| anti-CD22-MXD3 | 8 | 102.3 |
| Untreated | 24 | 451.6 |
| anti-CD22-control | 24 | 311.3 |
| anti-CD22-MXD3 | 24 | 52.0 |
| Untreated | 48 | 330.6 |
| anti-CD22-control | 48 | 450.4 |
| anti-CD22-MXD3 | 48 | 88.3 |
| Untreated | 72 | 417.5 |
| anti-CD22-control | 72 | 307.4 |
| anti-CD22-MXD3 | 72 | 140.3 |

Example 4

Reduction of Leukemia Cell Growth by Antibody-Antisense Oligonucleotide Conjugates In Vitro Reh cells were seeded as described in Example 3, and each well contained $20 \times 10^3$ live cells. Cells were incubated with anti-CD22-MXD3, anti-CD22-control, a mixture of unconjugated anti-CD22 antibody and the MXD3 targeting antisense oligonucleotide Isis No. 691563 ("Unconj. control"), or received no treatment. After four hours, the media containing the treatment was removed and replaced with fresh media containing no treatment. Cell growth was measured using the 3-[4,5-dimethylthiazol-2-yl]-2,5-diphenyltetrazolium bromide (MTT) assay (Promega, catalog # G5421, used according to manufacturer's instructions) to determine the number of live cells at various time points. The results are shown in Tables 4, 5, and 6 below. Each table shows data from a separate experiment. The data in Table 4 show that anti-CD22-MXD3 reduced Reh cell growth, while the unconjugated MXD3 targeting antisense oligonucleotide, Isis No. 691563, mixed with the CD22 antibody did not reduce Reh cell growth. The data in Table 5 show that Reh cell growth reduction by anti-CD22-MXD3 was dose responsive, and the data in Table 6 show that anti-CD22-MXD3 reduced Reh cell growth, while the anti-CD22-control conjugate did not reduce Reh cell growth. Thus, reduction of Reh cell growth requires both the antisense oligonucleotide that targets MXD3 and the attachment of that oligonucleotide to the anti-CD22 antibody.

TABLE 4

Effect of anti-CD22-MXD3 versus unconjugated control in vitro

| Conjugate | Concentration of anti-CD22 antibody (μM) | Time point (hours) | Average number of live cells × $10^3$ |
|---|---|---|---|
| Untreated | n/a | 4 | 20.8 |
| Unconj. control | 0.00831 | 4 | 19.9 |
| anti-CD22-MXD3 | 0.00831 | 4 | 16.3 |
| Untreated | n/a | 8 | 21 |
| Unconj. control | 0.00831 | 8 | 21.3 |
| anti-CD22-MXD3 | 0.00831 | 8 | 16.1 |
| Untreated | n/a | 24 | 35.4 |
| Unconj. control | 0.00831 | 24 | 36.5 |
| anti-CD22-MXD3 | 0.00831 | 24 | 26.8 |
| Untreated | n/a | 48 | 48.8 |

TABLE 4-continued

Effect of anti-CD22-MXD3 versus unconjugated control in vitro

| Conjugate | Concentration of anti-CD22 antibody (μM) | Time point (hours) | Average number of live cells × $10^3$ |
|---|---|---|---|
| Unconj. control | 0.00831 | 48 | 49.2 |
| anti-CD22-MXD3 | 0.00831 | 48 | 40.5 |
| Untreated | n/a | 72 | 66.1 |
| Unconj. control | 0.00831 | 72 | 67.3 |
| anti-CD22-MXD3 | 0.00831 | 72 | 55.2 |

TABLE 5

Two point dose response of anti-CD22-MXD3 in vitro

| Conjugate | Concentration of anti-CD22 antibody (uM) | Time point (hours) | Average number of live cells × $10^3$ |
|---|---|---|---|
| Untreated | n/a | 4 | 19.8 |
| anti-CD22-MXD3 | 0.00831 | 4 | 16.5 |
| anti-CD22-MXD3 | 0.0831 | 4 | 14.6 |
| Untreated | n/a | 8 | 21.3 |
| anti-CD22-MXD3 | 0.00831 | 8 | 16.1 |
| anti-CD22-MXD3 | 0.0831 | 8 | 15.4 |
| Untreated | n/a | 24 | 38.2 |
| anti-CD22-MXD3 | 0.00831 | 24 | 27.9 |
| anti-CD22-MXD3 | 0.0831 | 24 | 22.8 |
| Untreated | n/a | 48 | 58.7 |
| anti-CD22-MXD3 | 0.00831 | 48 | 39.4 |
| anti-CD22-MXD3 | 0.0831 | 48 | 37.3 |
| Untreated | n/a | 72 | 67.3 |
| anti-CD22-MXD3 | 0.00831 | 72 | 51 |
| anti-CD22-MXD3 | 0.0831 | 72 | 46.1 |

TABLE 6

Effect of anti-CD22-MXD3 versus conjugate containing control oligonucleotide in vitro

| Conjugate | Concentration of anti-CD22 antibody (uM) | Time point (hours) | Average number of live cells × $10^3$ |
|---|---|---|---|
| Untreated | n/a | 4 | 18.1 |
| anti-CD22-control | 0.5 | 4 | 17.3 |
| anti-CD22-MXD3 | 0.5 | 4 | 10.4 |
| Untreated | n/a | 8 | 17.8 |
| anti-CD22-control | 0.5 | 8 | 16.8 |
| anti-CD22-MXD3 | 0.5 | 8 | 11.1 |
| Untreated | n/a | 24 | 31.3 |
| anti-CD22-control | 0.5 | 24 | 27.1 |
| anti-CD22-MXD3 | 0.5 | 24 | 18.1 |
| Untreated | n/a | 48 | 50.1 |
| anti-CD22-control | 0.5 | 48 | 46.2 |
| anti-CD22-MXD3 | 0.5 | 48 | 33.1 |
| Untreated | n/a | 72 | 62.1 |
| anti-CD22-control | 0.5 | 72 | 57.8 |
| anti-CD22-MXD3 | 0.5 | 72 | 38.9 |

Example 5

Optimization of Antibody-Antisense Oligonucleotide Conjugate Preparation

In order to optimize the biological activity of the conjugates, the ratios of the azide to the anti-CD22 antibody, and the anti-CD22 antibody to the MXD3 antisense oligonucleotide (Isis No. 691563) were varied. The reaction time of the anti-CD22-MXD3 antisense oligonucleotide conjugation was also varied. The resulting conjugates were tested for reduction of Reh cell growth using the protocol described in Example 4. The results are shown in Tables 7 and 8. The optimal conditions were determined to be 1:100 anti-CD22 antibody:NHS-Azide and 1:20 azide labeled anti-CD22: MXD3 antisense oligonucleotide with a 30 minute incubation time. These conditions were used in all subsequent experiments.

TABLE 7

Optimization of anti-CD22 antibody:NHS-Azide ratio

| Conjugate | Ratio of anti-CD22 antibody to NHS-Azide | Time point (hours) | Average number of live cells × $10^3$ |
|---|---|---|---|
| Untreated | n/a | 4 | 19.3 |
| Anti-CD22-MXD3 | 1:10 | 4 | 11.4 |
| Anti-CD22-MXD3 | 1:100 | 4 | 9.5 |
| Untreated | n/a | 8 | 21.3 |
| Anti-CD22-MXD3 | 1:10 | 8 | 12.4 |
| Anti-CD22-MXD3 | 1:100 | 8 | 9.4 |
| Untreated | n/a | 24 | 34.5 |
| Anti-CD22-MXD3 | 1:10 | 24 | 19.3 |
| Anti-CD22-MXD3 | 1:100 | 24 | 17.7 |
| Untreated | n/a | 48 | 46.8 |
| Anti-CD22-MXD3 | 1:10 | 48 | 32.6 |
| Anti-CD22-MXD3 | 1:100 | 48 | 30.1 |
| Untreated | n/a | 72 | 55.1 |
| Anti-CD22-MXD3 | 1:10 | 72 | 41.2 |
| Anti-CD22-MXD3 | 1:100 | 72 | 37.8 |

TABLE 8

Optimization of azide-labeled anti-CD22 antibody:antisense oligonucleotide ratio

| Conjugate | Ratio of anti-CD22 antibody to oligonucleotide | Reaction time (hours) | Time point (hours) | Average number of live cells × $10^3$ |
|---|---|---|---|---|
| Untreated | n/a | n/a | 4 | 20.1 |
| Anti-CD22-MXD3 | 1:10 | 0.5 | 4 | 10.4 |
| Anti-CD22-MXD3 | 1:20 | 0.5 | 4 | 9.5 |
| Anti-CD22-MXD3 | 1:10 | 1 | 4 | 10.6 |
| Anti-CD22-MXD3 | 1:20 | 1 | 4 | 10.4 |
| Anti-CD22-MXD3 | 1:10 | 2 | 4 | 11.1 |
| Anti-CD22-MXD3 | 1:20 | 2 | 4 | 9.4 |
| Untreated | n/a | n/a | 8 | 20.6 |
| Anti-CD22-MXD3 | 1:10 | 0.5 | 8 | 13.4 |
| Anti-CD22-MXD3 | 1:20 | 0.5 | 8 | 12.6 |
| Anti-CD22-MXD3 | 1:10 | 1 | 8 | 10.9 |
| Anti-CD22-MXD3 | 1:20 | 1 | 8 | 10.9 |
| Anti-CD22-MXD3 | 1:10 | 2 | 8 | 12.2 |
| Anti-CD22-MXD3 | 1:20 | 2 | 8 | 9.9 |
| Untreated | n/a | n/a | 24 | 37.2 |

TABLE 8-continued

Optimization of azide-labeled anti-CD22 antibody:antisense oligonucleotide ratio

| Conjugate | Ratio of anti-CD22 antibody to oligonucleotide | Reaction time (hours) | Time point (hours) | Average number of live cells × 10³ |
|---|---|---|---|---|
| Anti-CD22-MXD3 | 1:10 | 0.5 | 24 | 19.4 |
| Anti-CD22-MXD3 | 1:20 | 0.5 | 24 | 19.5 |
| Anti-CD22-MXD3 | 1:10 | 1 | 24 | 20.2 |
| Anti-CD22-MXD3 | 1:20 | 1 | 24 | 19 |
| Anti-CD22-MXD3 | 1:10 | 2 | 24 | 22.1 |
| Anti-CD22-MXD3 | 1:20 | 2 | 24 | 19.6 |
| Untreated | n/a | n/a | 48 | 49.7 |
| Anti-CD22-MXD3 | 1:10 | 0.5 | 48 | 30.2 |
| Anti-CD22-MXD3 | 1:20 | 0.5 | 48 | 28.5 |
| Anti-CD22-MXD3 | 1:10 | 1 | 48 | 29 |
| Anti-CD22-MXD3 | 1:20 | 1 | 48 | 28.4 |
| Anti-CD22-MXD3 | 1:10 | 2 | 48 | 32.5 |
| Anti-CD22-MXD3 | 1:20 | 2 | 48 | 28.8 |
| Untreated | n/a | n/a | 72 | 62.6 |
| Anti-CD22-MXD3 | 1:10 | 0.5 | 72 | 43.9 |
| Anti-CD22-MXD3 | 1:20 | 0.5 | 72 | 37 |
| Anti-CD22-MXD3 | 1:10 | 1 | 72 | 41.4 |
| Anti-CD22-MXD3 | 1:20 | 1 | 72 | 35.9 |
| Anti-CD22-MXD3 | 1:10 | 2 | 72 | 39.4 |
| Anti-CD22-MXD3 | 1:20 | 2 | 72 | 34.7 |

TABLE 9

Effect of combination treatments in vitro

| Treatment | Time point (hours) | Average number of live cells × 10³ |
|---|---|---|
| Untreated | 4 | 21.7 |
| Doxo | 4 | 22.3 |
| Vcr | 4 | 20.2 |
| Anti-CD22-MXD3 | 4 | 6.4 |
| Doxo + anti-CD22-MXD3 | 4 | 7.1 |
| Vcr + anti-CD22-MXD3 | 4 | 6.9 |
| Untreated | 8 | 23.5 |
| Doxo | 8 | 22.9 |
| Vcr | 8 | 19.6 |
| Anti-CD22-MXD3 | 8 | 8.9 |
| Doxo + anti-CD22-MXD3 | 8 | 8.4 |
| Vcr + anti-CD22-MXD3 | 8 | 6.8 |
| Untreated | 24 | 38.5 |
| Doxo | 24 | 30 |
| Vcr | 24 | 27.8 |
| Anti-CD22-MXD3 | 24 | 14.8 |
| Doxo + anti-CD22-MXD3 | 24 | 11.7 |
| Vcr + anti-CD22-MXD3 | 24 | 8.6 |
| Untreated | 48 | 50.5 |
| Doxo | 48 | 37 |
| Vcr | 48 | 33.1 |
| Anti-CD22-MXD3 | 48 | 26 |
| Doxo + anti-CD22-MXD3 | 48 | 20 |
| Vcr + anti-CD22-MXD3 | 48 | 12.9 |
| Untreated | 72 | 58.4 |
| Doxo | 72 | 41.8 |
| Vcr | 72 | 34.8 |
| Anti-CD22-MXD3 | 72 | 37.1 |
| Doxo + anti-CD22-MXD3 | 72 | 25.1 |
| Vcr + anti-CD22-MXD3 | 72 | 18.8 |

Example 6

Reduction of Leukemia Cell Growth by Antibody-Antisense Oligonucleotide Conjugates in Combination with Small Molecule Drugs In order to test the effect of combinations of anti-CD22-MXD3 with small molecule anticancer drugs, Reh cells were treated with anti-CD22-MXD3, Doxorubicin (Doxo), and/or Vincristine (Vcr) alone or in various combinations. Reduction of cell growth was measured with the MTT assay as described in Example 4. Based on an estimation that each conjugate contained one antibody molecule and four oligonucleotides, conjugate amounts were calculated to result in a final oligonucleotide concentration of 2 µM. The small molecule drugs were added at their experimentally determined $IC_{50}$'s: 2.56 ng/mL for Doxorubicin and 1.18 ng/mL for Vincristine. The results, shown in Table 9 below, indicate that anti-CD22-MXD3 was more effective at reducing Reh cell growth than either Doxorubicin or Vincristine, and combinations of anti-CD22-MXD3 with Doxorubicin or Vincristine were more effective at reducing Reh cell growth than either of the small molecule drugs or the conjugate alone.

Example 7

Effect of Antibody-Antisense Oligonucleotide Conjugates on Normal Blood Cell Viability In Vitro In order to test whether the anti-CD22-MXD3 conjugate specifically targets CD22 positive cells, various types of normal blood cells were treated with the conjugate, or a mixture of the unconjugated anti-CD22 antibody and the MXD3 antisense oligonucleotide ("Unconj. control"), or no treatment. B cells, non-B (counterpart population of B cell isolation) cells, and CD34 positive hematopoietic stem cells (HSCs) were plated in complete Reh growth media in 48-well plates. Based on an estimation that each conjugate contained one antibody molecule and four oligonucleotides, conjugate amounts were calculated to result in a final oligonucleotide concentration of 2 µM. For the unconjugated control treatment, 2 µM MXD3 oligonucleotide and 0.5 µM antibody was added. The cell count assay was performed as described in Example 4. The viability of all cell populations decreased over time, due to the inability of Reh media to support primary cell growth. As shown in Table 10 below, the unconjugated control had no effect on cell viability of any cell type, while anti-CD22-MXD3 decreased cell viability relative to the controls in B cells only, not in the cell types expected to be CD22 negative.

TABLE 10

Reduction of normal blood cell viability in vitro

| Treatment | Cell type | Time point (hours) | Average number of live cells × $10^3$ |
|---|---|---|---|
| Untreated | B-cells | 4 | 15.5 |
| Unconj. control | B-cells | 4 | 16 |
| Anti-CD22-MXD3 | B-cells | 4 | 11 |
| Untreated | B-cells | 8 | 14.6 |
| Unconj. control | B-cells | 8 | 14.7 |
| Anti-CD22-MXD3 | B-cells | 8 | 10.7 |
| Untreated | B-cells | 24 | 12.5 |
| Unconj. control | B-cells | 24 | 13.2 |
| Anti-CD22-MXD3 | B-cells | 24 | 8.9 |
| Untreated | B-cells | 48 | 10.3 |
| Unconj. control | B-cells | 48 | 10.5 |
| Anti-CD22-MXD3 | B-cells | 48 | 6.7 |
| Untreated | B-cells | 72 | 7.7 |
| Unconj. control | B-cells | 72 | 8 |
| Anti-CD22-MXD3 | B-cells | 72 | 2.9 |
| Untreated | Non-B-cells | 4 | 11 |
| Unconj. control | Non-B-cells | 4 | 11.8 |
| Anti-CD22-MXD3 | Non-B-cells | 4 | 10.7 |
| Untreated | Non-B-cells | 8 | 11.2 |
| Unconj. control | Non-B-cells | 8 | 10.7 |
| Anti-CD22-MXD3 | Non-B-cells | 8 | 11.4 |
| Untreated | Non-B-cells | 24 | 10.5 |
| Unconj. control | Non-B-cells | 24 | 10.2 |
| Anti-CD22-MXD3 | Non-B-cells | 24 | 10.5 |
| Untreated | Non-B-cells | 48 | 7.4 |
| Unconj. control | Non-B-cells | 48 | 7.5 |
| Anti-CD22-MXD3 | Non-B-cells | 48 | 8.8 |
| Untreated | Non-B-cells | 72 | 4 |
| Unconj. control | Non-B-cells | 72 | 3.9 |
| Anti-CD22-MXD3 | Non-B-cells | 72 | 3.2 |
| Untreated | CD34+ HSCs | 4 | 18 |
| Unconj. control | CD34+ HSCs | 4 | 18.8 |
| Anti-CD22-MXD3 | CD34+ HSCs | 4 | 18.3 |
| Untreated | CD34+ HSCs | 8 | 17.7 |
| Unconj. control | CD34+ HSCs | 8 | 17.3 |
| Anti-CD22-MXD3 | CD34+ HSCs | 8 | 17.4 |
| Untreated | CD34+ HSCs | 24 | 17.6 |
| Unconj. control | CD34+ HSCs | 24 | 17.6 |
| Anti-CD22-MXD3 | CD34+ HSCs | 24 | 16.8 |
| Untreated | CD34+ HSCs | 48 | 10.6 |
| Unconj. control | CD34+ HSCs | 48 | 11.3 |
| Anti-CD22-MXD3 | CD34+ HSCs | 48 | 11.5 |
| Untreated | CD34+ HSCs | 72 | 6.6 |
| Unconj. control | CD34+ HSCs | 72 | 6 |
| Anti-CD22-MXD3 | CD34+ HSCs | 72 | 3.5 |

Example 8

Effect of Antibody-Antisense Oligonucleotide Conjugates on Apoptosis In Vitro

In order to test whether anti-CD22-MXD3 reduces cell growth via apoptosis, a caspase activity assay with a luciferase reporter was performed (Caspase Glo 3/7 kit, Promega, catalog # G8090) using Reh cells. The cells were treated with anti-CD22-MXD3, anti-CD22-control, or they received no treatment. Based on an estimation that each conjugate contained one antibody molecule and four oligonucleotides, conjugate amounts were calculated to result in a final oligonucleotide concentration of 2 µM. Four hours following treatment, the caspase activity assay was performed according to the manufacturer's directions. The results, shown in Table 11 below, indicate that apoptosis was increased by treatment with anti-CD22-MXD3 but not by anti-CD22-control.

TABLE 11

Induction of caspase activity by anti-CD22-MXD3 in vitro

| Conjugate | Caspase activity (Relative Luminescence) |
|---|---|
| Untreated | 257.7 |
| anti-CD22-control | 284.3 |
| Anti-CD22-MXD3 | 486.7 |

Example 9

Effect of Antibody-Antisense Oligonucleotide Conjugates on Survival Following Leukemia Cell Inoculation In Vivo In order to test the effect of anti-CD22-MXD3 in vivo, 6-8 week old female NOD scid gamma (NSG) mice were inoculated with Reh leukemia cells or patient-derived leukemia cells, then treated with anti-CD22-MXD3, the unconjugated control, or saline twice per week for three weeks via intravenous administration. Each treatment group that received Reh cell inoculations contained 4 animals, and each group that received patient-derived leukemia cell inoculations contained 8 animals. The results are shown in Tables 12 and 13 below as the number of days that each mouse survived following inoculation.

TABLE 12

Survival following Reh cell inoculation in vivo

| Mouse identification number | Treatment group | Survival time (days) |
|---|---|---|
| 1 | Saline | 20 |
| 5 | Saline | 20 |
| 9 | Saline | 20 |
| 10 | Saline | 20 |
| 2 | 1 mg/kg Unconj. control | 21 |
| 6 | 1 mg/kg Unconj. control | 21 |
| 11 | 1 mg/kg Unconj. control | 19 |
| 12 | 1 mg/kg Unconj. control | 19 |
| 3 | 0.2 mg/kg anti-CD22-MXD3 | 49 |
| 7 | 0.2 mg/kg anti-CD22-MXD3 | 50 |
| 13 | 0.2 mg/kg anti-CD22-MXD3 | 35 |
| 14 | 0.2 mg/kg anti-CD22-MXD3 | 36 |
| 4 | 1 mg/kg anti-CD22-MXD3 | 57 |
| 8 | 1 mg/kg anti-CD22-MXD3 | 54 |
| 15 | 1 mg/kg anti-CD22-MXD3 | 54 |
| 16 | 1 mg/kg anti-CD22-MXD3 | 54 |

TABLE 13

Survival following primary leukemia cell inoculation in vivo

| Mouse identification number | Treatment group | Survival time (days) |
|---|---|---|
| 1 | Saline | 31 |
| 5 | Saline | 27 |
| 9 | Saline | 29 |
| 13 | Saline | 27 |
| 17 | Saline | 29 |
| 21 | Saline | 27 |
| 25 | Saline | 29 |
| 29 | Saline | 29 |
| 2 | 1 mg/kg Unconj. control | 30 |
| 6 | 1 mg/kg Unconj. control | 29 |
| 10 | 1 mg/kg Unconj. control | 29 |
| 14 | 1 mg/kg Unconj. control | 29 |
| 18 | 1 mg/kg Unconj. control | 30 |
| 22 | 1 mg/kg Unconj. control | 30 |

TABLE 13-continued

Survival following primary leukemia cell inoculation in vivo

| Mouse identification number | Treatment group | Survival time (days) |
|---|---|---|
| 26 | 1 mg/kg Unconj. control | 32 |
| 30 | 1 mg/kg Unconj. control | 29 |
| 3 | 0.2 mg/kg anti-CD22-MXD3 | 63 |
| 7 | 0.2 mg/kg anti-CD22-MXD3 | 63 |
| 11 | 0.2 mg/kg anti-CD22-MXD3 | 63 |
| 15 | 0.2 mg/kg anti-CD22-MXD3 | 63 |
| 19 | 0.2 mg/kg anti-CD22-MXD3 | 63 |
| 23 | 0.2 mg/kg anti-CD22-MXD3 | 63 |
| 27 | 0.2 mg/kg anti-CD22-MXD3 | 63 |
| 31 | 0.2 mg/kg anti-CD22-MXD3 | 63 |
| 4 | 1 mg/kg anti-CD22-MXD3 | 77 |
| 8 | 1 mg/kg anti-CD22-MXD3 | 77 |
| 12 | 1 mg/kg anti-CD22-MXD3 | 77 |
| 16 | 1 mg/kg anti-CD22-MXD3 | 71 |
| 20 | 1 mg/kg anti-CD22-MXD3 | 77 |
| 24 | 1 mg/kg anti-CD22-MXD3 | 77 |
| 28 | 1 mg/kg anti-CD22-MXD3 | 77 |
| 32 | 1 mg/kg anti-CD22-MXD3 | 77 |

Example 10

Figure 2:
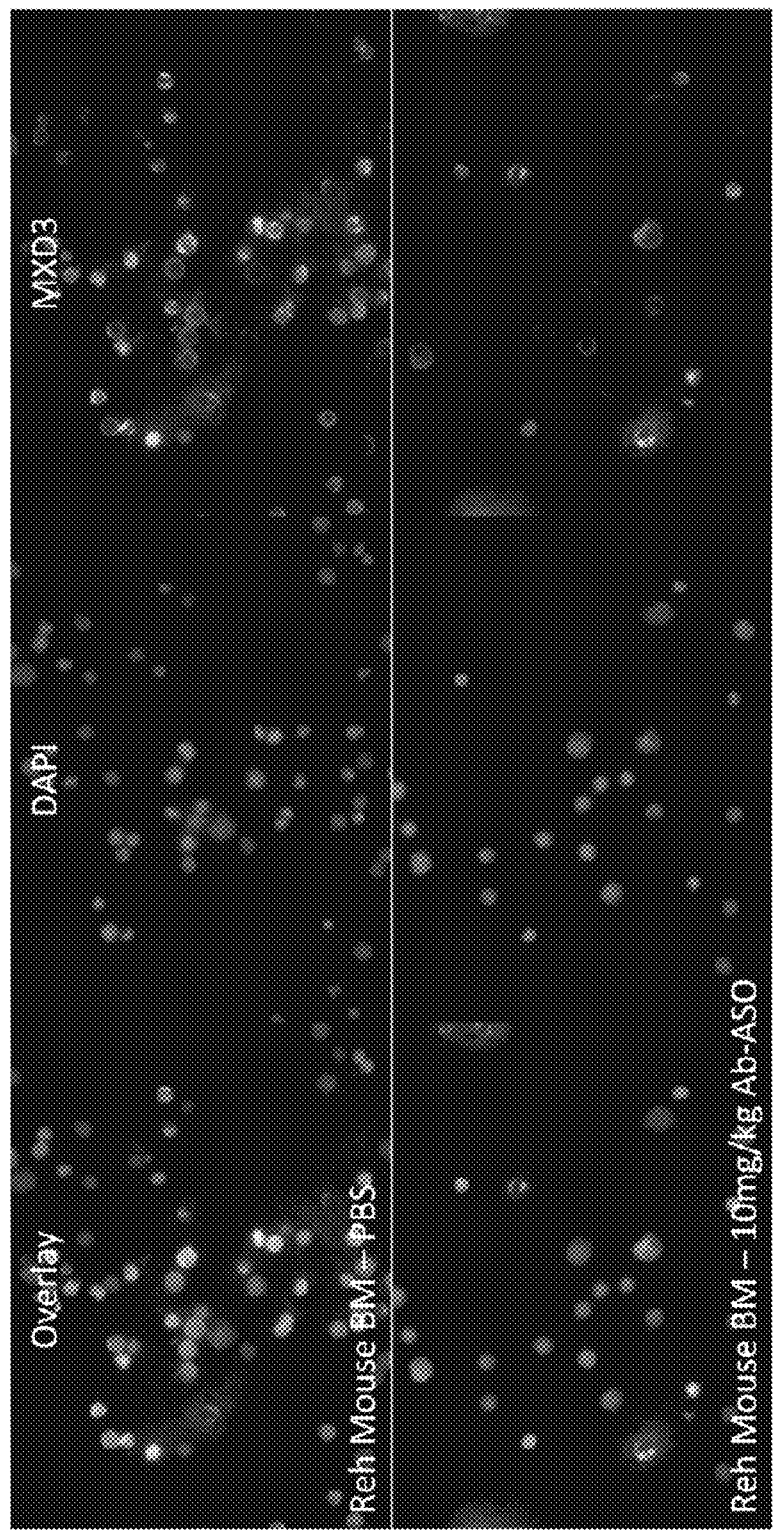
FIG. 2 shows bone marrow cells of mice treated for eight hours with anti-CD22-MXD3 conjugate or no treatment 18 days after being inoculated with Reh cells. The cells were stained for MXD3 and with DAPI.

Effect of Antibody-Antisense Oligonucleotide Conjugates on Target Expression and Leukemia Cell Population In Vivo In order to further test the effects of anti-CD22-MXD3 in vivo, mice were inoculated with Reh cells as described in Example 9. The presence of leukemia cells in the bone marrow was confirmed by Giemsa staining on day 17 following Reh inoculation. On day 18, two mice received one 10 mg/kg dose of anti-CD22-MXD3 via intravenous administration and two mice received PBS. Analyses of MXD3 protein expression and of the leukemia cell population were performed at 8 and 24 hours following conjugate or PBS treatment. MXD3 protein expression was measured in the same BM samples using immunocytochemistry, as described in Example 3. The leukemia cell population was analyzed by counting total bone marrow cells using a hemacytometer and microscope. Cells from bone marrow of NSG mice that were not inoculated were also counted. The results are shown in Tables 14 and 15 below, and the immunohistochemistry images are shown in FIG. 2. MXD3 mRNA expression will also be measured using RT-PCR following total RNA extraction from cells harvested from bone marrow.

TABLE 14

MXD3 protein expression in vivo

| Treatment | Time point (hours following treatment) | MFI |
|---|---|---|
| Saline | 8 | 131.8 |
| anti-CD22-MXD3 | 8 | 83.4 |
| Saline | 24 | 147.9 |
| anti-CD22-MXD3 | 24 | 133.9 |

TABLE 15

Bone marrow cell count

| Treatment | Mice | Time point (hours following treatment) | Number of cells in bone marrow × 10$^6$ |
|---|---|---|---|
| Saline | Inoculated | 8 | 12 |
| anti-CD22-MXD3 | Inoculated | 8 | 10 |
| Saline | Inoculated | 24 | 19 |
| anti-CD22-MXD3 | Inoculated | 24 | 12 |
| Saline | Not inoculated | 8 | 12.6 |
| anti-CD22-MXD3 | Not inoculated | 8 | 13 |
| Saline | Not inoculated | 24 | 12.7 |
| anti-CD22-MXD3 | Not inoculated | 24 | 12.9 |

Example 11

Synthesis of Antibody-Double-Stranded Oligonucleotide Conjugates

In order to test whether conjugates comprising a double-stranded oligonucleotide stabilize the MXD3 antisense oligonucleotide and/or improve properties of the anti-CD22-MXD3 antisense oligonucleotide conjugates, oligonucleotides complementary to Isis No. 632461 or 691563 (herein referred to as "complementary strands") are synthesized using standard solid phase oligonucleotide synthetic methods. In certain embodiments, the complementary strand comprises all phosphodiester internucleoside linkages. In certain embodiments, the complementary strand comprises two terminal phosphorothioate internucleoside linkages at each end of the oligonucleotide and internal phosphodiester internucleoside linkages. In certain embodiments, the complementary strand comprises 2'-O-methyl modified sugars in the two terminal nucleosides at each end of the oligonucleotide, and the internal nucleosides are unmodified 2'-OH (RNA) or 2'-deoxy (DNA) nucleosides. Click chemistry conjugation to an anti-CD22 antibody, as described in Example 2, is performed prior to or following hybridization of the complementary strand to Isis No. 691563. Alternatively, the complementary strand is modified with 5'-DBCO-TEG, as described in Example 2, and hybridized to Isis No. 632461 either prior to or following click chemistry conjugation to an anti-CD22 antibody. The resulting anti-CD22-double-stranded oligonucleotide conjugates are used in the assays described herein.

Example 12

MXD3 Inhibition by an Antibody-Antisense Oligonucleotide Conjugate on Blood Cells In Vitro In order to further test whether the anti-CD22-MXD3 conjugate specifically targets CD22 positive cells, various types of normal blood cells were treated with the conjugate, or a mixture of the unconjugated anti-CD22 antibody and the MXD3 antisense oligonucleotide ("Unconj. control"), or no treatment. B cells, non-B (counterpart population of B cell isolation) cells, and CD34 positive HSCs were plated and treated as described in Example 7. MXD3 protein expression was analyzed by immunohistochemistry as described in Example 3. As shown in Table 16 below, the unconjugated control had a modest inhibitory effect on MXD3 protein expression in B-cells, and anti-CD22-MXD3 inhibited MXD3 protein expression in B-cells to a greater extent than the unconjugated control. Furthermore, MXD3 protein expression is low in non-B cells and CD34 positive HSCs and is not inhibited by the unconjugated control or anti-CD22-MXD3.

TABLE 16

Reduction of MXD3 protein expression in blood cells in vitro

| Treatment | Cell type | Time point (hours) | MFI |
|---|---|---|---|
| Untreated | B-cells | 4 | 46 |
| Unconj. control | B-cells | 4 | 33 |
| Anti-CD22-MXD3 | B-cells | 4 | 21 |
| Untreated | Non-B-cells | 4 | 8.9 |
| Unconj. control | Non-B-cells | 4 | 8.2 |
| Anti-CD22-MXD3 | Non-B-cells | 4 | 11.5 |
| Untreated | CD34+ HSCs | 4 | 13.3 |
| Unconj. control | CD34+ HSCs | 4 | 13.1 |
| Anti-CD22-MXD3 | CD34+ HSCs | 4 | 14.9 |

Example 13

Tolerability of an Antibody-Antisense Oligonucleotide Conjugate In Vivo

In order to test the tolerability of the anti-CD22-MXD3 conjugate, the body weights of mice that were inoculated with leukemia cells and treated as described in Example 9 were monitored. All groups continuously gained weight following inoculation (data not shown). One representative mouse from each group that was inoculated with primary patient derived leukemia cells also underwent weekly CBC and blood chemistry panel analyses, including measurement of liver transaminase levels (ALT and AST). The results, shown as the average for each treatment group in Tables 17 and 18 below, indicate that in both the conjugated (anti-CD22-MXD3) and unconjugated forms ("Unconj. control"), the CD22 antibody and MXD3 antisense oligonucleotide were well tolerated.

TABLE 17

CBC results for leukemia inoculated mice

| Treatment group | Time point (weeks after inoculation) | WBC (K/μL) | RBC (M/μL) | Hemoglobin (g/dL) | Hematocrit (%) | MCV (fL) | MCH (pg) | MCHC (g/dL) |
|---|---|---|---|---|---|---|---|---|
| Saline | 0 | 1.3 | 8.5 | 13.4 | 36.3 | 42.8 | 15.8 | 36.9 |
| Saline | 1 | 0.8 | 9.8 | 13.4 | 43.8 | 44.8 | 13.7 | 30.6 |
| Saline | 2 | 1.2 | 10.3 | 15.0 | 51.9 | 50.4 | 14.6 | 28.9 |
| Saline | 3 | 6.2 | 9.9 | 13.3 | 43.3 | 43.8 | 13.4 | 30.7 |
| 1 mg/kg Unconj. control | 0 | 1.1 | 9.8 | 14.1 | 41.7 | 42.6 | 14.4 | 33.8 |
| 1 mg/kg Unconj. control | 1 | 0.8 | 8.3 | 11.7 | 36.9 | 44.2 | 14.0 | 31.7 |
| 1 mg/kg Unconj. control | 2 | 2.6 | 10.2 | 14.8 | 51.9 | 50.7 | 14.5 | 28.5 |
| 1 mg/kg Unconj. control | 3 | 1.5 | 6.6 | 9.4 | 29.1 | 43.8 | 14.2 | 32.3 |
| 0.2 mg/kg anti-CD22-MXD3 | 0 | 0.7 | 8.6 | 12.3 | 37.1 | 43.1 | 14.3 | 33.2 |
| 0.2 mg/kg anti-CD22-MXD3 | 1 | 1.0 | 10.4 | 14.5 | 47.6 | 46.0 | 14.0 | 30.5 |
| 0.2 mg/kg anti-CD22-MXD3 | 2 | 1.0 | 9.5 | 14.1 | 49.0 | 51.5 | 14.8 | 28.8 |
| 0.2 mg/kg anti-CD22-MXD3 | 3 | 1.0 | 9.2 | 12.7 | 40.6 | 44.2 | 13.8 | 31.3 |
| 1 mg/kg anti-CD22-MXD3 | 0 | 1.1 | 9.3 | 13.5 | 40.0 | 43.2 | 14.6 | 33.8 |
| 1 mg/kg anti-CD22-MXD3 | 1 | 0.7 | 9.9 | 13.9 | 43.9 | 44.2 | 14.0 | 31.7 |
| 1 mg/kg anti-CD22-MXD3 | 2 | 1.2 | 8.7 | 13.0 | 44.7 | 51.7 | 15.0 | 29.1 |
| 1 mg/kg anti-CD22-MXD3 | 3 | 1.1 | 9.1 | 12.9 | 41.2 | 45.1 | 14.1 | 31.3 |

TABLE 18

Blood chemistry results for leukemia inoculated mice

| Treatment group | Time point (weeks after inoculation) | ALT (U/L) | AST (U/L) | Total bilirubin (mg/dL) |
|---|---|---|---|---|
| Saline | 0 | 32.2 | 121.3 | 0.2 |
| Saline | 1 | 67.2 | 355.2 | 0.0 |
| Saline | 2 | 36.2 | 126.0 | 0.1 |
| Saline | 3 | 37.8 | 148.5 | 0.0 |
| 1 mg/kg Unconj. control | 0 | 38.9 | 154.1 | 0.1 |
| 1 mg/kg Unconj. control | 1 | 40.4 | 170.2 | 0.1 |
| 1 mg/kg Unconj. control | 2 | 42.2 | 203.8 | 0.0 |
| 1 mg/kg Unconj. control | 3 | 46.5 | 213.3 | 0.0 |
| 0.2 mg/kg anti-CD22-MXD3 | 0 | 35.2 | 119.4 | 0.1 |
| 0.2 mg/kg anti-CD22-MXD3 | 1 | 63.4 | 367.4 | 0.1 |
| 0.2 mg/kg anti-CD22-MXD3 | 2 | 47.6 | 221.8 | 0.1 |
| 0.2 mg/kg anti-CD22-MXD3 | 3 | 23.7 | 97.5 | 0.1 |
| 1 mg/kg anti-CD22-MXD3 | 0 | 29.5 | 81.8 | 0.1 |
| 1 mg/kg anti-CD22-MXD3 | 1 | 64.8 | 338.4 | 0.0 |
| 1 mg/kg anti-CD22-MXD3 | 2 | 45.1 | 235.4 | 0.1 |
| 1 mg/kg anti-CD22-MXD3 | 3 | 27.0 | 109.2 | 0.1 |

Example 14

Novel Targeted Therapy for Precursor B Cell Acute Lymphoblastic Leukemia: Anti-CD22 Antibody-MXD3 Antisense Oligonucleotide Conjugate The exponential rise in molecular and genomic data has generated a vast array of therapeutic targets. Oligonucleotide-based technologies to down regulate these molecular targets have promising therapeutic efficacy. However, there is relatively limited success in translating this into effective in vivo cancer therapeutics. The primary challenge is the lack of effective cancer cell-targeted delivery methods, particularly for a systemic disease such as leukemia. We developed a novel leukemia-targeting compound composed of a monoclonal antibody directly conjugated to an antisense oligonucleotide (ASO). Our compound uses an ASO that specifically targets the transcription factor MAX dimerization protein 3 (MXD3), which was previously identified to be involved in precursor B cell (preB) acute lymphoblastic leukemia (ALL) cell survival. The MXD3 ASO was conjugated to an anti-CD22 antibody (αCD22 Ab) that specifically targets most preB ALL. Our in vitro studies demonstrated (1) αCD22 Ab-ASO mediated MXD3 knockdown and leukemia cell apoptosis and (2) cytotoxicity of the conjugate in normal B cells, but not in other hematopoietic cells, including hematopoietic stem cells. Furthermore, the conjugate treatment at the lowest dose tested (0.2 mg/kg Ab for 6 doses—twice a week for 3 weeks) more than doubled the mouse survival time in both Reh (median survival time 20.5 vs. 42.5 days, p<0.001) and primary preB ALL (median survival time 29.3 vs. 63 days, p<0.0001) xenograft models. Our conjugate that uses αCD22 Ab to target the novel molecule MXD3, which is highly expressed in preB ALL cells, is a novel therapeutic approach.

Introduction

Precursor B cell (preB) acute lymphoblastic leukemia (ALL) is the most common type of ALL (1, 2). The prognosis for adult preB ALL is poor, with overall cure rates of approximately 40% (3-5). Although the overall cure rate of pediatric preB ALL has improved dramatically through the introduction of intensive combination chemotherapy since the 1960s, the prognosis for certain subtypes remains very poor, with cure rates of approximately 30% (6-8). In addition, current chemo and radiation therapies can cause late effects, including secondary malignancies (9, 10). Targeted therapies for ALL have the potential to be more effective and have fewer side effects than current treatments.

Antibody (Ab)-based therapeutics are promising targeted treatment strategies that are currently being investigated for ALL (11, 12). Although monoclonal antibodies (mAbs), as a single agent, have limited therapeutic efficacy, they have improved efficacy when combined with standard induction therapy (13). Furthermore, mAbs have been shown to have a role as cell-targeting agents as in Ab-drug (14-16) or -immunotoxin (17-20) conjugates. More recently, there have been promising results with Ab constructs that redirect T cells, such as bispecific T-cell engager (BiTE) Abs (21, 22) and chimeric antigen receptor (CAR)-based T cell therapies (23-25). Antisense oligonucleotides (ASOs) have enormous potential as gene-targeted agents that have high specificity (26-30). Over the past decade, clinical trials using ASO therapies have demonstrated modest efficacy for cancers, including chronic lymphocytic leukemia (31), prostate and lung cancers (32-35). Major challenges with ASO-based cancer therapies remain, however, and include non-specific delivery and inefficient intracellular uptake (36-38). Conjugates of mAb and ASO can deliver ASOs to target leukemia cells for selective knockdown of leukemia-specific genes in vivo, minimizing non-specific ASO delivery. To date only a few Ab-ASO conjugates have been reported (39, 40).

CD22 is a B-lineage restricted surface molecule that modulates B cell receptor signaling (41). It is an ideal target for Ab-based therapy against B-cell malignancies because of its high expression and rapid internalization upon Ab binding (17, 42, 43). MAX dimerization protein 3 (MXD3) is a basic-helix-loop-helix-leucine-zipper transcription factor that is part of the MYC/MAX/MXD transcriptional network involved in cellular proliferation (44-46). Previously we demonstrated that MXD3 functions as an anti-apoptotic protein and that knockdown of MXD3 can be a novel effective therapeutic strategy for preB ALL in vitro (47, 48). In this study, we developed a novel leukemia-targeting compound using MXD3 ASO conjugated to anti-CD22 Ab (αCD22 Ab) for preB ALL. We demonstrated that the αCD22 Ab-MXD3 ASO conjugate has significant in vitro and in vivo therapeutic efficacy using preclinical xenograft mouse models of human preB ALL.

Materials and Methods

ASO and Ab: ASOs were designed and synthesized using standard solid phase oligonucleotide synthetic methods (Isis Pharmaceuticals, Carlsbad, Calif.). The MXD3 ASO sequence is 5'-CACAGGGACGCATAAC-3'. It is a 3-10-3 (S)-cEt gapmer, wherein the three nucleosides at the 5'-end and the three nucleosides at the 3'-end comprise 2',4'-constrained-2'-O-Ethyl Bridged Nucleic acid (cEt), and the ten middle nucleosides are 2'-deoxynucleosides (49). The negative control ASO sequence, which has no known homology to mammalian genes and has minimal nonspecific effects, is 5'-CCTTCCCTGAAGGTTCCTCC-3'. It is a 5-10-5 2'-methoxyethyl (MOE) gapmer, wherein the five nucleosides at the 5'-end and the five nucleosides at the 3'-end comprise MOE modifications, and the ten middle nucleosides are 2'-deoxynucleosides. All internucleoside linkages are phosphorothioate linkages. The cytosine bases are 5-methylcytosines. The 5'-end of each oligonucleotide was modified to comprise a cyclooctyne for subsequent click chemistry conjugation to an azide-labeled antibody via 1,3-dipolar cycloaddition (50). The 5'-DBCO-TEG phosphoramidite (Glen Research, Sterling, Va.) was coupled to the 5'-end of each oligonucleotide using standard solid phase methods to form a phosphodiester linkage between the oligonucleotide and the 5'-DBCO-TEG moiety. Ammonia deprotection was completed at room temperature for a minimum of 48 hours.

The αCD22 mAbs (αCD22 Ab: JT22.1) were generated by the fusion of NS-1 myeloma cells with spleen cells from BALB/c mice immunized with baby hamster kidney cells transfected with human CD22 cDNA encoding the transmembrane domain (BP 2208-2263) and extracytoplasmic domains 1 and 2 (BP 57-867). Hybridomas were screened and selected based on the ability of the mAbs to specifically bind to 293T cells that were transfected with CD22 extracytoplasmic domains 1 and 2, but not with non-transfected control cells. Positive clones were subcloned twice. The αCD22 Abs were purified using protein G Hi-Trap columns (Amersham, Arlington Heights, Ill.). JT22.1 was assessed for CD22 ligand blocking as previously described (51). The isotype of the JT22.1 was determined to be IgG1 using a Mouse mAb Isotyping kit (Amersham).

Cell Lines and Patient-Derived Leukemia Cells: The human preB ALL cell line Reh was purchased from ATCC (Manassas, Va.) and the Jurkat cell line was obtained from Dr. Kit Lam's Lab at UC Davis. Cells were maintained at 37° C. in a 5% $CO_2$ incubator in RPMI 1640 (Life Technologies, Grand Island, N.Y.) supplemented with 10% heat-inactivated fetal bovine serum, 100 U/mL penicillin and 100 μg/mL streptomycin (Thermo Scientific, Waltham, Mass.), 0.25% D-glucose (Sigma-Aldrich, St. Louis, Mo.), 1 mM sodium pyruvate, and 10 mM HEPES buffer (Thermo Scientific).

Primary leukemia samples were collected from patients with informed consent based on our institutionally-approved IRB protocol. Normal blood cells were collected with IRB approval from anonymized discarded apheresis bags from healthy donors. B cells (lymphocytes) and CD34 positive (+) hematopoietic stem cells (HSCs) were isolated using magnetic beads (Miltenyi Biotec, San Diego, Calif.) and non-B cells were collected from the counterpart of B cell isolation. Cell purity of the isolated B cells and CD34+HSCs was confirmed by flow cytometry (FC500 Beckman Coulter, Brea, Calif.) using anti-CD19 and anti-CD34 Ab, respectively (BD Biosciences, San Jose, Calif.).

αCD22 Ab-ASO Conjugate: αCD22 Ab was incubated with NHS-PEG4-Azide (azide) (Thermo Scientific) (dissolved in DMSO) in PBS at a molar ratio of 1:100 for 3 hours at 4° C. Excess azide was removed using a Zeba 7k MW desalting column (Thermo Scientific). The azide-conjugated Ab was then incubated with cyclooctyne-modified ASO in water at a 1:20 ratio at 37° C. for 30 minutes to form the αCD22 Ab-ASO conjugates. Excess ASO was removed as described above. The above reaction method was optimized by titrating molar ratio of αCD22 Ab, azide, and ASO, and incubation time of αCD22 Ab-azide with ASO. The conjugation of the Ab and ASO was validated using SDS-PAGE gel assays. For the experiments in which free αCD22 Ab or ASO were used as a control, the equivalent amount of αCD22 Ab in the conjugate, or ASO in the conjugation reaction, was used.

In Vitro Treatment with αCD22 Ab-ASO Conjugate: Reh cells were plated at 20,000 cells in 125 μL medium per well in 48-well plates in triplicate for each treatment group and time point. The cells were treated with αCD22 Ab-ASO conjugates (MXD3 or control) at indicated concentrations, or left untreated. MXD3 protein expression and live cell counts were assessed at 4, 8, 24, 48, or 72 hours after treatment. The cells were incubated with indicated treatment for 4 hours in complete growth medium, which was then replaced with fresh growth medium.

Immunocytochemistry and Fluorescent Image Intensity Quantification: Cells were fixed with 10% buffered formalin and stained with anti-MXD3 monoclonal mouse Ab (Neuromab, Davis, Calif.) and secondary goat anti-mouse Ab-Alexa488 (Life Technologies, Grand Island, N.Y.) as previously described (47). Nuclei were stained with DAPI (40, 6-diamidino-2-phenylindole) (Life Technologies). The MXD3 protein expression levels were quantified by mean fluorescent intensity (MFI) using Image J (NIH, Bethesda, Md.) as previously described (47).

Apoptosis Assay: Cell apoptosis was measured by annexin V (BD Biosciences) or caspase activity using the Caspase 3/7 Glo kit (Promega, Madison, Wis.) as previously described (47). Annexin V was measured by flow cytometry using the FC500. Caspase level was measured by a Centro LB 960 Microplate Luminometer (Berthold Technologies, Oak Ridge, Tenn.).

In Vivo Therapeutic Studies in Mice: All procedures were performed in compliance with our institutionally-approved animal care protocol in the barrier facility vivarium at the Institute for Regenerative Cures in accordance with AALAC. Human leukemia xenograft models were established with either Reh or patient-derived leukemia samples from two different donors and 5 to 10 week-old female NOD/SCID/IL2Rg−/− (NSG) mice. The two primary samples were from patients who were diagnosed as high-risk based on the current diagnostic criteria (52). For the patient-derived leukemia models, passage 3 of serially-transplanted NSG mice were used. Five million leukemia cells were transplanted via intravenous (Reh) or intra-tibial (patient-derived cells) injection. Treatment was initiated 24 hours after leukemia inoculation, with intravenous injection of PBS, unconjugated Ab and ASO, or conjugate at indicated doses. Mice were randomly assigned to each treatment group. Mice were treated twice a week for 3 weeks, and each cohort included 4, 6, or 8 mice. In one of the patient-derived models, CBC and chemistry panels were checked from one representative mouse per cohort weekly for 4 weeks. Mice were monitored daily until they were moribund, or, for the Reh model, developed hind limb paralysis. Mice were sacrificed and leukemia cells were harvested from bone marrow (BM). Human leukemia cells were confirmed by flow cytometry using anti-HLA-ABC Ab (BioLegend, San Diego, Calif.) and B-cell leukemia panels, including anti-human CD10, 19, 20, and 22 Abs (BD Biosciences).

For treatment effect assessment, Reh leukemia engrafted mice were used with a high dose of αCD22 Ab-MXD3 ASO conjugate (10 mg/kg of the Ab). Reh engraftment was confirmed by Giemsa staining and phenotyping on tibial BM aspirates on day 17 after leukemia inoculation. To assess in vivo targeted effects a dose of either PBS or αCD22 Ab-MXD3 ASO conjugate was given on day 18, with 2 mice per cohort. Eight and 24 hours after treatment, mice were euthanized and harvested BM was tested for live cell counts, MXD3 knockdown, and apoptosis.

Statistical Analysis: For in vitro studies, the results were summarized descriptively by mean and standard error (SE), and linear regression was used to compare outcomes for conjugate to comparison groups. Multiple comparisons were also performed at each time point based on ANOVA. For in vivo studies, previous work in our lab with the human leukemia xenograft model showed survival times for control group animals that were brief (approximately 3 weeks) and very consistent (SD less than 5 days) (53). Thus sample sizes of 4 to 8 animals per group were predicted by power analysis to be adequate to detect clinically relevant shifts in survival times, for example an increase to 5 weeks, with very high power (>90% even after adjustment for multiple comparisons.) Survival was summarized by Kaplan-Meier plots and compared by log-rank tests and linear regression analyses with 95% confidence intervals (CI). No samples or animals were excluded for analysis. The analyses were carried out in Prism version 6, SAS version 9.3, or R.

Results

In Vitro MXD3 Knockdown is Increased in a Dose-Dependent Manner of αCD22 Ab-MXD3 ASO Conjugate in preB ALL Cells Our group and others have shown that nearly 100% of Reh cells express CD22 (47, 53). Reh cells treated with various concentrations of the conjugate showed dose-dependent MXD3 protein knockdown at 4 and 24 hours after treatment (FIG. 3A). Using an average of both time points, the percentage knockdown was 8% (0.0005 µM), 37% (0.005 µM), 39% (0.05 µM), and 83% (0.5 µM) (FIG. 3B). The MXD3 protein level was not affected by treatment with αCD22 Ab alone at the concentrations of 0.05 and 0.5 µM (FIG. 3A). Furthermore, MXD3 knockdown by the conjugate treatment was partially inhibited when unconjugated αCD22 Ab was added simultaneously at concentrations of equal or 10 times higher than the conjugated Ab concentration (FIGS. 4B and C). For the 0.5 µM conjugate, MXD3 knockdown was reduced from 86% to 78% or 44% (1 and 10 fold unconjugated Ab added, respectively). For the 0.05 µM conjugate, the knockdown was reduced from 80% to 73% or 59% (1 and 10 fold Ab added, respectively). Cell viability was positively correlated to MXD3 knockdown (data not shown). Ab treatment alone did not mediate cytotoxicity at the concentrations used (data not shown).

In Vitro Therapeutic Efficacy of the αCD22 Ab-MXD3 ASO Conjugate in preB ALL Cells We chose the highest concentration of the conjugate (0.5 µM of the Ab) for the subsequent in vitro studies to ensure demonstration of therapeutic efficacy. Reh cells treated with the αCD22 Ab-MXD3 ASO conjugate showed a 63% and 60.3% reduction in MXD3 protein expression compared to untreated or αCD22 Ab-control ASO treated cells, respectively, 4 hours after treatment (FIGS. 5A and B). We next assessed cell viability after treatment using annexin V (FIGS. 5C and D). Untreated or αCD22 Ab-control ASO conjugate-treated cells showed few annexin V positive cells (average 2.3% and 9.2% at 2 hours, and 2.5% and 9.9% at 4 hours, respectively) whereas the αCD22 Ab-MXD3 ASO conjugate-treated cells showed significantly higher levels of annexin V positive cells (average 30.5% at 2 hours, and 55.3% at 4 hours) (FIG. 5D). Caspase levels also showed a significant increase in the αCD22 Ab-MXD3 ASO conjugate-treated cells compared to controls at both 2 and 4 hours after treatment (FIG. 5E). As a result, Reh cells exhibited significantly decreased live cell counts over 72 hours after one treatment with αCD22 Ab-MXD3 ASO compared to controls (FIG. 5F).

In Vitro Treatment Effects of the αCD22 Ab-MXD3 ASO Conjugate on Primary Hematopoietic Cells Human B cells express low levels of MXD3 whereas CD34+HSCs and non-B cells have negligible levels of MXD3 (47). We investigated potential cytotoxic effects of the conjugate on B cells as well as on CD34+HSCs and non-B cells. Isolated B cells and CD34+HSCs had purity greater than 95% (data not shown). These cells were treated with the αCD22 Ab-MXD3 ASO, an equimolar amount of free αCD22 Ab plus free MXD3 ASO, or untreated. B cells treated with the αCD22 Ab-MXD3 ASO conjugate or free Ab plus MXD3 ASO showed a 54% and 28% reduction in MXD3 protein expression 4 hours after treatment compared to untreated, respectively (FIGS. 6A and B). CD34+HSCs and non-B cells treated with identical conditions showed no significant difference in MXD3 protein expression between all treatments (data not shown). B cells treated with the αCD22 Ab-MXD3 ASO conjugate showed accelerated cell death in vitro compared to minimal cytotoxicity in both CD34+HSCs and non-B cells (FIG. 6C).

Figure 7:
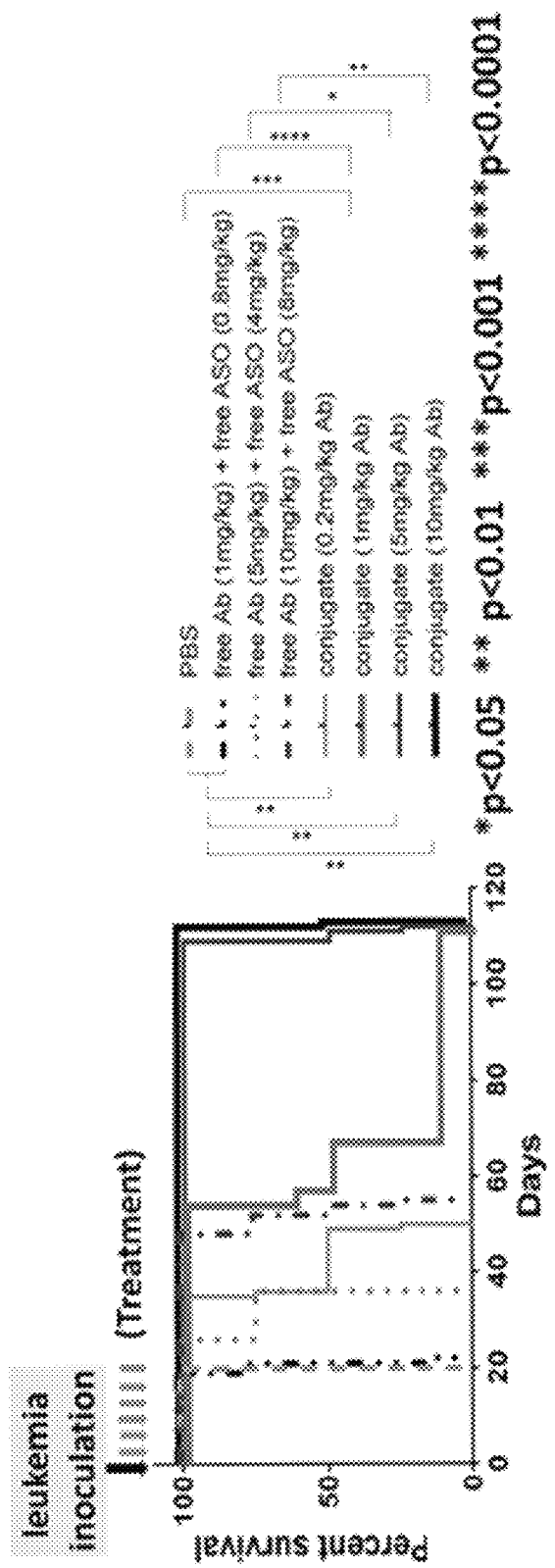
FIG. 7: αCD22 Ab-MXD3 ASO conjugate shows significant in vivo dose-dependent therapeutic efficacy in Reh human leukemia mouse model. Kaplan-Meier survival curve for mice inoculated with Reh cells and treated with the αCD22 Ab-MXD3 ASO conjugate. Data from two independent experiments were combined. In the first experiment, the mice were treated with PBS, free αCD22 Ab (1 mg/kg) plus free MXD3 ASO (0.8 mg/kg), and two different doses of the αCD22 Ab-MXD3 ASO conjugate (0.2 mg/kg or 1 mg/kg of the Ab) (n=4). In the second experiment, the mice were treated with free αCD22 Ab (1, 5, or 10 mg/kg) plus free MXD3 ASO (0.8, 4, or 8 mg/kg), respectively, and three different doses of the αCD22 Ab-MXD3 ASO conjugate (1, 5, or 10 mg/kg of the Ab) (n=4). PBS vs. conjugate at any dose (0.2, 1, 5, or 10 mg/kg of the Ab) (p<0.01, *p<0.001, p<0.01, or p<0.01, respectively). Free αCD22 Ab (1 mg/kg) plus free MXD3 ASO (0.8 mg/kg) vs. conjugate at any dose (0.2, 1, 5, or 10 mg/kg of the Ab) (p<0.01, p<0.0001, p<0.01, or p<0.01, respectively). Free Ab plus free ASO vs. conjugate at the equivalent dose of the Ab (1, 5, or 10 mg/kg) (**p<0.0001, *p=0.01, or **p<0.01, respectively).

In Vivo Therapeutic Efficacy of the αCD22 Ab-MXD3 ASO Conjugate in Preclinical preB ALL Xenograft Mouse Models We tested the in vivo therapeutic efficacy of the conjugate in a xenograft mouse model using the Reh cell line. All the mice that received PBS died of leukemia on day 20 as expected (FIG. 7). All the mice that received free αCD22 Ab plus free MXD3 ASO died of leukemia between day 19 and 55 (median survival time was day 21, 36, 53 for the 1, 5, 10 mg/kg free Ab dose, respectively), with no difference in survival between the 1 mg/kg Ab dose and PBS, but an increase in survival of 15.5 days for each increase in dose (95% CI 8.9-22.1 days, p<0.001). The mice that received the conjugate, regardless of the dose, survived significantly longer (median survival time was day 42.5, 62, 110 and 112.5 for the 0.2, 1, 5, and 10 mg/kg Ab dose, respectively) than the mice that received PBS or equivalent unconjugated controls. The increase in survival was 50.1 days at the 1 mg/kg Ab dose compared to the unconjugated control (95% CI 39.6-60.6 days, p<0.001) with a dose response effect of 25 days for each dose increase or decrease (p<0.001). At the time of harvest, all the mice were confirmed to have developed human leukemia (HLA and CD22 positive) (FIG. 11). During treatment, the mice in all the treatment groups remained healthy without weight loss (FIGS. 8A and B).

To confirm that the in vivo therapeutic efficacy of the conjugate is mediated by MXD3 knockdown leading to leukemia cell apoptosis, we performed a pilot study treating Reh engrafted mice with high tumor burden (3 weeks after leukemia inoculation) with a single dose Ab-ASO conjugate treatment. The Reh cells harvested from the BM of the conjugate-treated mice showed lower levels of MXD3 expression than PBS-treated mice both at 8 (FIG. 9A) and 24 hours (data not shown) after treatment. The BM cells of the conjugate-treated mice showed a much higher percentage of apoptotic Reh cells which were double positive for CD22 and annexin V: 33.2% vs. 4.8% at 8 hours and 29.5% vs. 2.5% at 24 hours (FIG. 9B). These results demonstrate that the in vivo therapeutic efficacy of the αCD22 Ab-MXD3 ASO conjugate was mediated by MXD3 knockdown-induced apoptosis in leukemic cells.

Figure 12A:
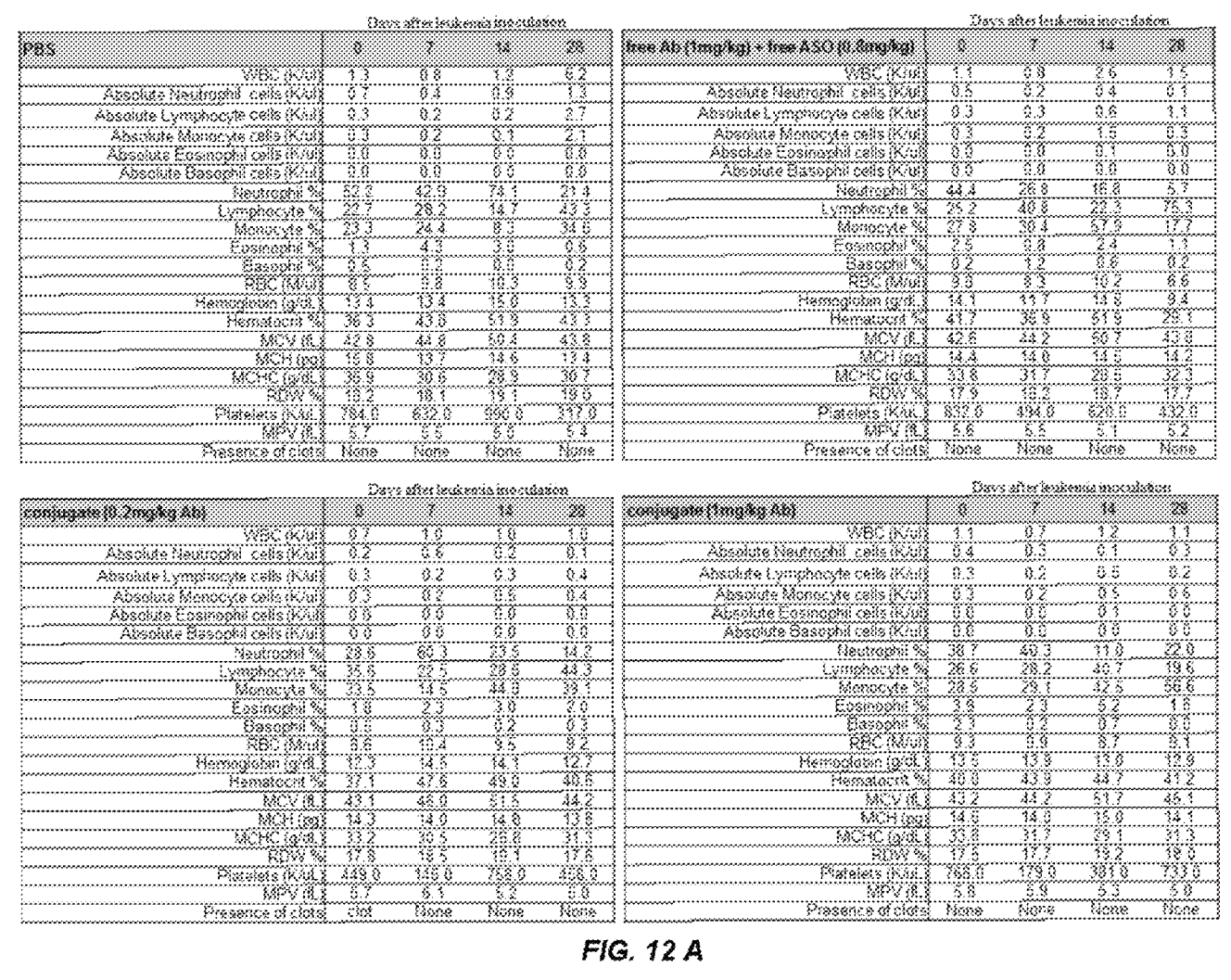
Figure 12B:
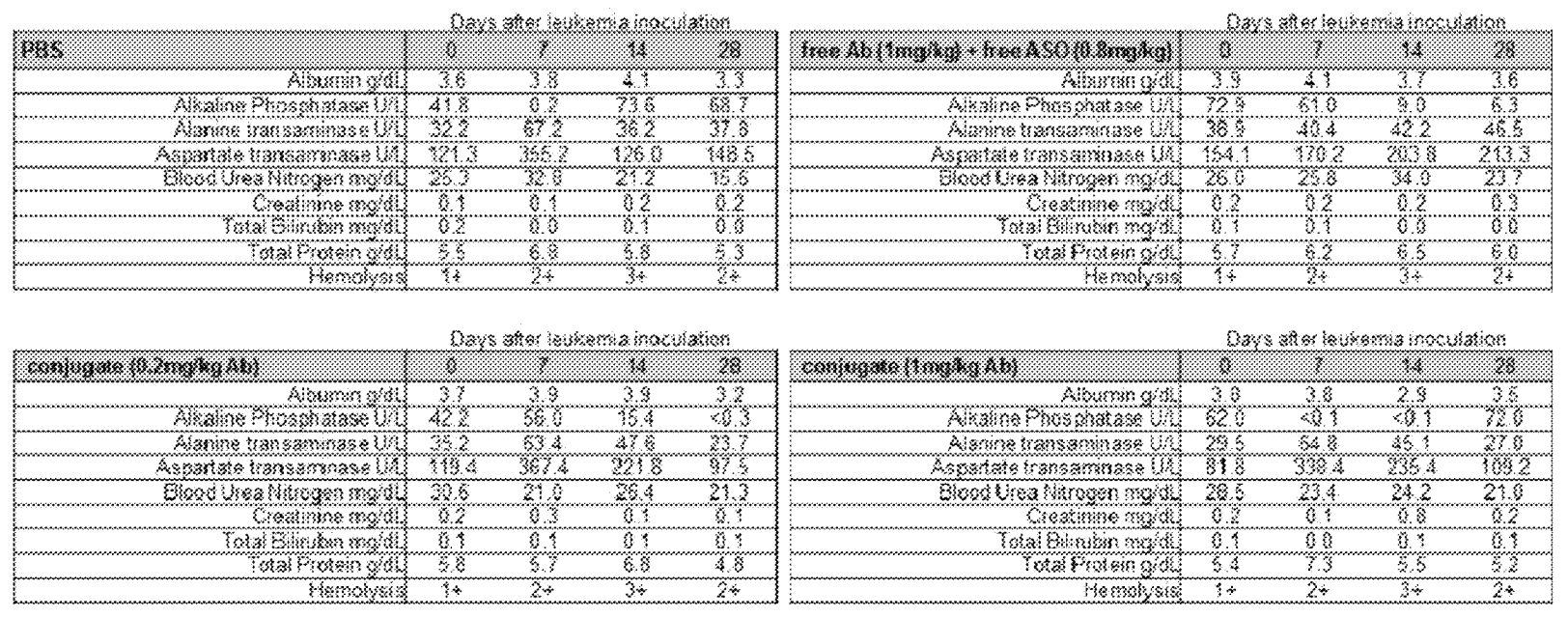

In Vivo Therapeutic Efficacy of the αCD22 Ab-MXD3 ASO Conjugate in Preclinical preB ALL Human Patient-Derived Xenograft Mouse Models We next tested the in vivo therapeutic efficacy of the conjugate in two different patient-derived leukemia xenograft models. We have previously shown that primary preB ALL cells, including the two samples used in this study, express CD22 (also FIG. 11) and MXD3 (47, 53). The conjugate, even at the two lowest doses tested in the Reh model, showed significant therapeutic efficacy in both models. In the sample A model, all the mice that received PBS or free αCD22 Ab plus free MXD3 ASO died of leukemia between day 27 and 32 (median survival time 29 and 29.5 days, respectively), whereas those that received the conjugate, at 0.2 or 1 mg/kg Ab dose, survived significantly longer (median survival time 63 and 76 days, respectively). Mean improvement for 0.2 or 1 mg/kg Ab dose was 22.4 days (95% CI 16.3-28.5 days, $p<0.001$) and 32.1 days (95% CI 26.0-38.2 days, $p<0.001$), respectively (FIG. 10A). In the sample B model, all the mice that received PBS or free Ab plus free ASO died of leukemia between day 42 and 46 (median survival time 43 and 45 days, respectively), whereas those that received the conjugate, at either dose, survived significantly longer (median survival time 53 and 57 days, respectively). Mean improvement was 27.3 days (95% CI 21.5-33.0 days, $p<0.001$) (FIG. 10B). At the time of harvest, all the mice were confirmed to have developed human leukemia (HLA and CD22 positive) (FIGS. 11B and C). Toxicity was assessed in the sample A model during the treatment, which showed essentially no hematologic or non-hematologic toxicities (FIG. 12 and FIG. 8C).

Discussion

Given the abundance of genetic information now available, a multitude of highly specific therapeutic targets are available. The use of oligonucleotides, such as ASO and small interfering RNA (siRNA), has been studied as an emerging method to target specific RNA sequences (27, 54, 55). However, clinical translation of these techniques has had limited therapeutic success in oncology (31-33). The primary challenge is target-specific and efficient intracellular delivery of oligonucleotides (26, 27, 36-38). To overcome this limitation, we have developed an effective ASO-conjugated Ab delivery method for the treatment of preB ALL.

Figure 3:
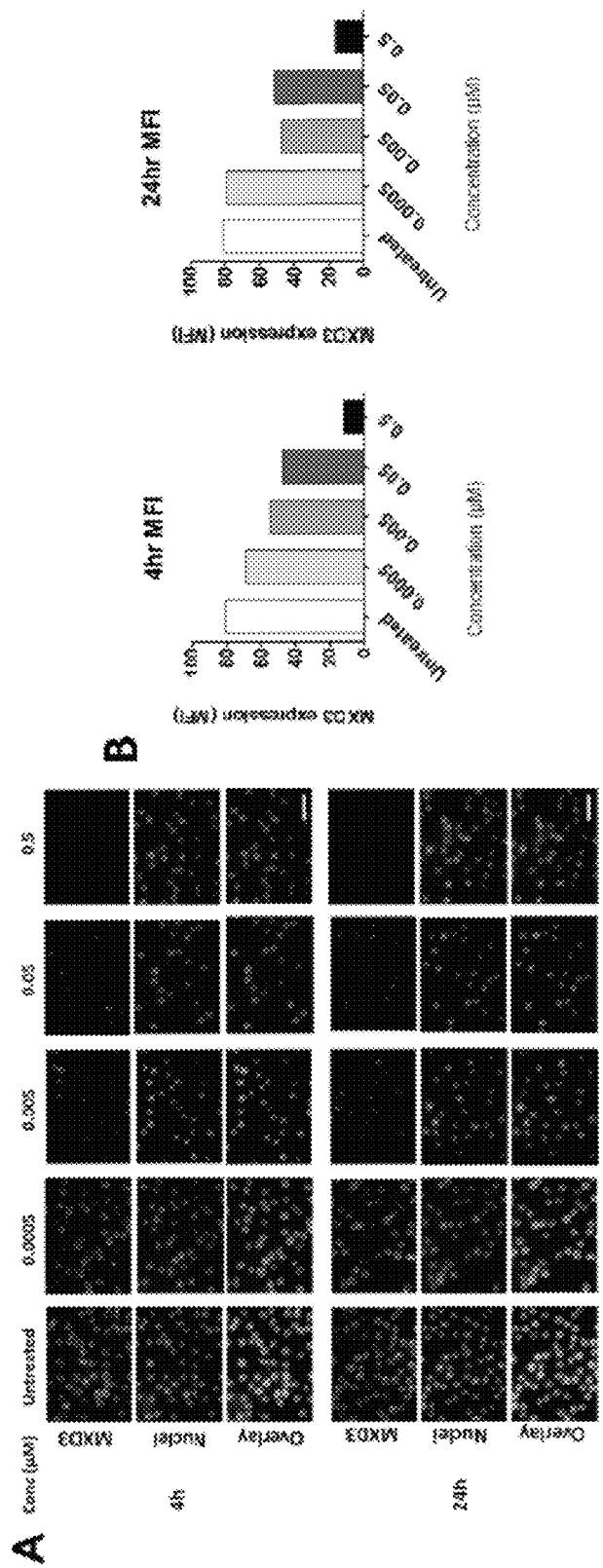
FIG. 3: αCD22 Ab-MXD3 ASO conjugate demonstrates MXD3 knockdown in preB ALL cells in a concentration-dependent manner. (A) Reh cells were treated with the αCD22 Ab-MXD3 ASO conjugate at four different concentrations (0.0005, 0.005, 0.05, and 0.5 μM of the Ab in the conjugate). MXD3 protein expression was measured at 4 and 24 hours after the treatment. The overlay pictures show a composite image of both MXD3 protein (with Alexa488) and nuclei (with DAPI). Images were acquired at 40× magnification/1.4 numerical aperture at room temperature using a Nikon Ti-U inverted microscope and NIS-Elements BR software. Scale bar indicates 50 μm. (B) Mean fluorescence intensity (MFI) was used to quantify MXD3 protein expression from (A).
Figure 4:
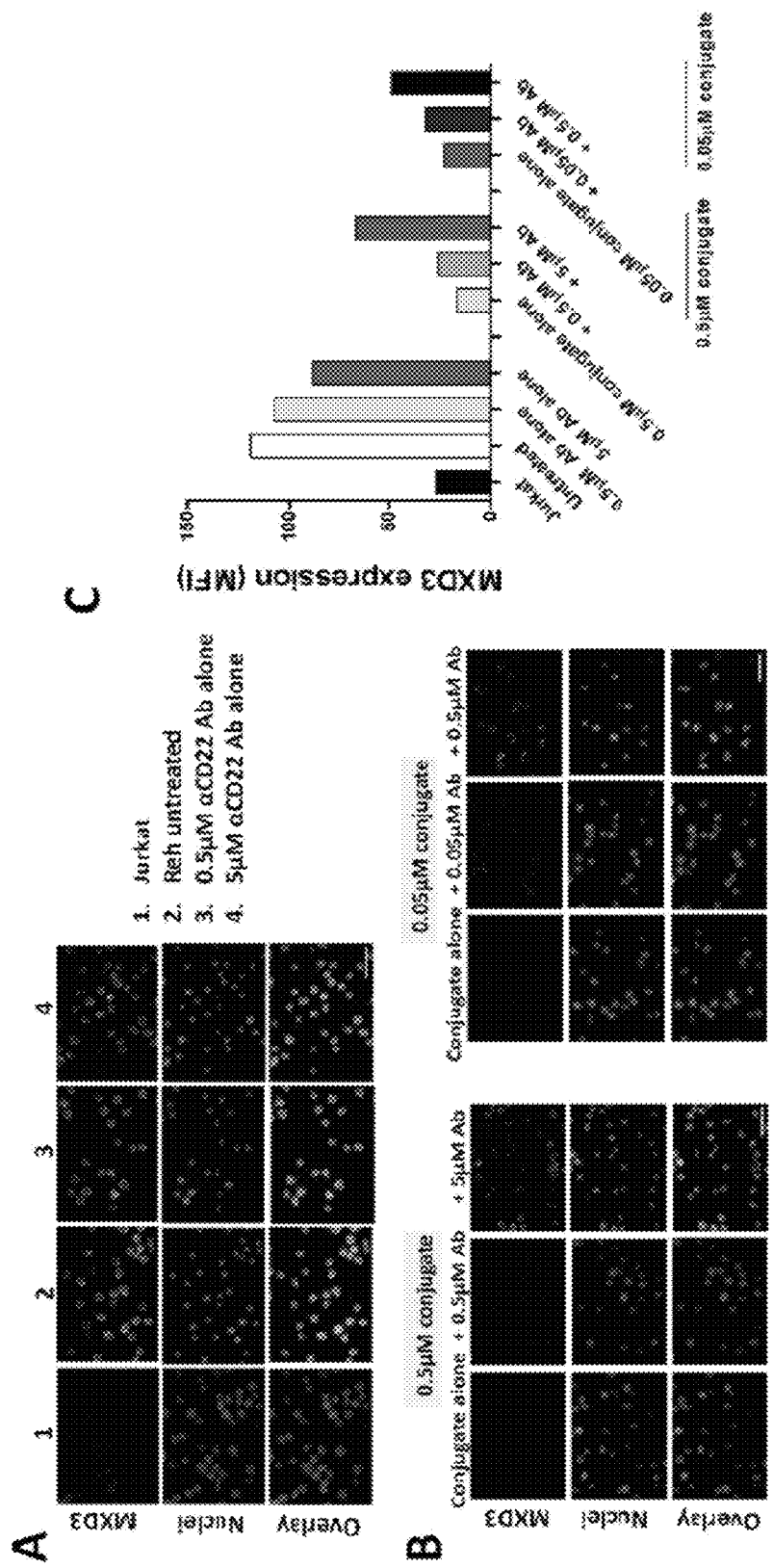
FIG. 4: The αCD22 Ab-MXD3 ASO conjugate, but not αCD22 Ab alone, shows MXD3 knockdown. (A) Treatment of Reh cells with the αCD22 Ab only at 0.5 μM or 5 μM did not show significant MXD3 knockdown. Jurkat cells were used as a negative control for MXD3 expression. (B) Reh cells were treated with the αCD22 Ab-MXD3 ASO conjugate (0.5 μM or 0.05 μM) with or without cold αCD22 Ab at indicated concentrations above. MXD3 knockdown by the conjugate treatment was partially inhibited when cold αCD22 Ab was added simultaneously at the concentrations of equal or 10 times higher than the Ab concentration in the conjugate. Images were acquired at 40× magnification/1.4 numerical aperture at room temperature using a Nikon Ti-U inverted microscope and NIS-Elements BR software. (C) MFI from (A) and (B). For 0.5 μM of the conjugate, the percentage knockdown was 86% of untreated. Addition of the Ab, at 0.5 μM or 5 μM, reduced the percentage MXD3 knockdown to 78% and 44%, respectively. For 0.05 μM of the conjugate, the percentage knockdown was 80% of untreated. Addition of the Ab, at 0.05 μM or 0.5 μM, reduced the percentage knockdown to 73% and 59%, respectively. MXD3 protein expression were measured at 4 hours after treatment. Scale bar indicates 50 μm.
Figure 5:
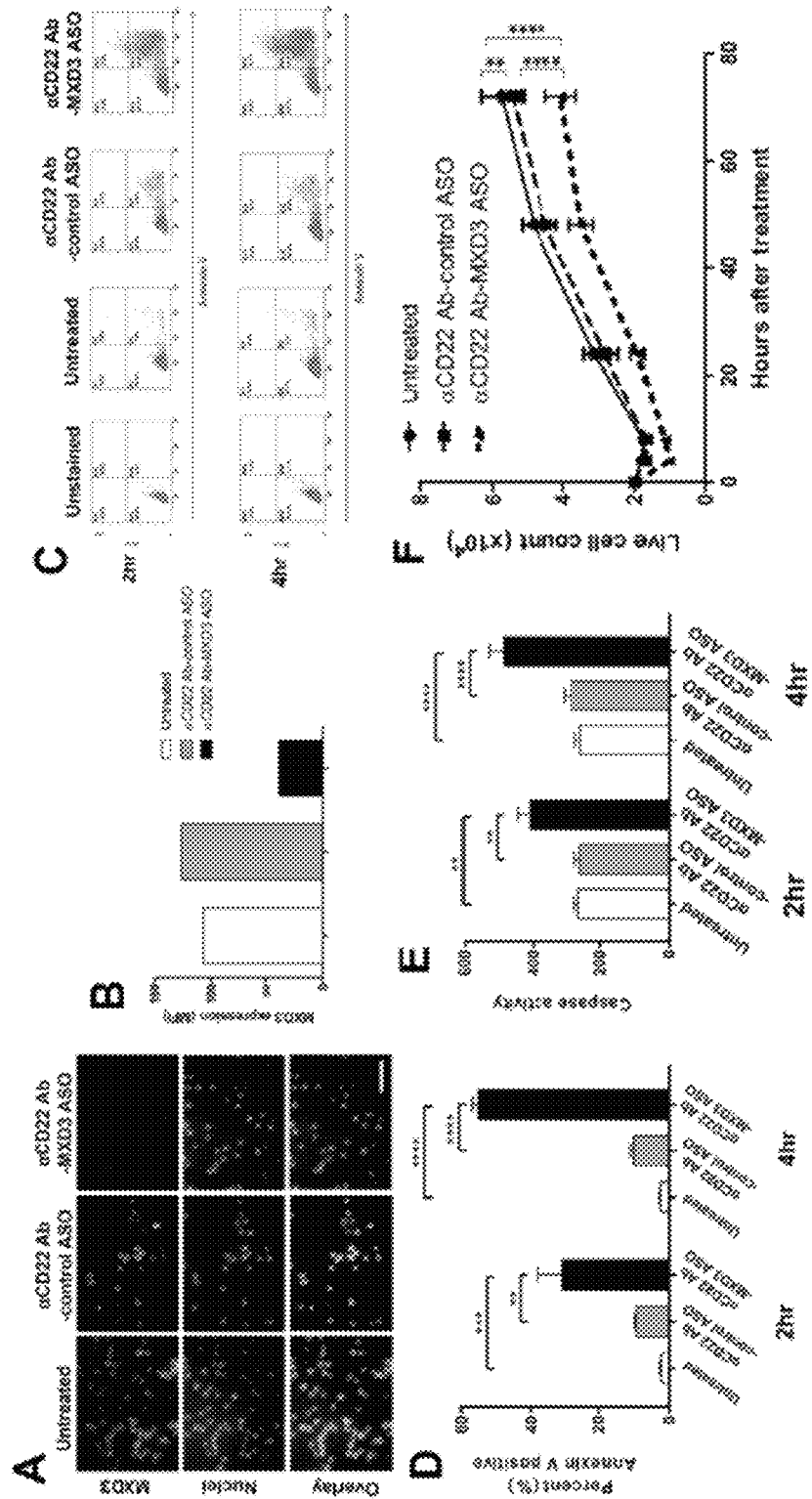
FIG. 5: αCD22 Ab-MXD3 ASO conjugate demonstrates MXD3 knockdown leading to cell apoptosis in preB ALL cells. (A) Reh cells treated with αCD22 Ab-MXD3 or αCD22 Ab-control ASO conjugate, or left untreated, were measured for MXD3 protein expression by fluorescent immunocytochemistry 4 hours after treatment. Images were acquired at 40× magnification/1.4 numerical aperture at room temperature using a Nikon Ti-U inverted microscope and NIS-Elements BR software. Scale bar indicates 50 μm. The overlay pictures show a composite image of both MXD3 protein (with Alexa488) and nuclei (with DAPI). (B) Mean fluorescence intensity (MFI) was used to quantify MXD3 protein expression. Each bar represents the average MFI of all measured cells per treatment type, from one experiment. (C) Cell apoptosis measured by annexin V using flow cytometry. Dot plots shown are from one representative experiment. (D) Quantification of annexin V positive cells. Data are means from 2 independent experiments. Error bars represent SD (n=2 for each time point). The cells treated with αCD22 Ab-MXD3 ASO conjugate showed significantly more annexin V positive cells than either the untreated cells (*p=0.0003 and p<0.0001) or those treated with the αCD22 Ab-control ASO conjugate (p=0.0014 and **p<0.0001), at 2 and 4 hours, respectively. (E) Cell apoptosis measured by caspase 3 and 7. Cells were treated the same way as in (D) with the same control. Histograms represent caspase measured by luminescence signal at 2 and 4 hours after treatment. (F) Reh cells exhibited significantly decreased live cell counts over 72 hours after one treatment with αCD22 Ab-MXD3 ASO compared to controls. Data are an average of 2 independent experiments. Error bars represent SD (n=6 for each time point). Cells treated with the αCD22 Ab-MXD3 ASO conjugate showed significantly higher average caspase than either the untreated cells (p=0.0013 and **p<0.0001) or those treated with the αCD22 Ab-control ASO conjugate (p=0.0011 and ****p<0.0001), at 2 and 4 hours, respectively.
Figure 9:
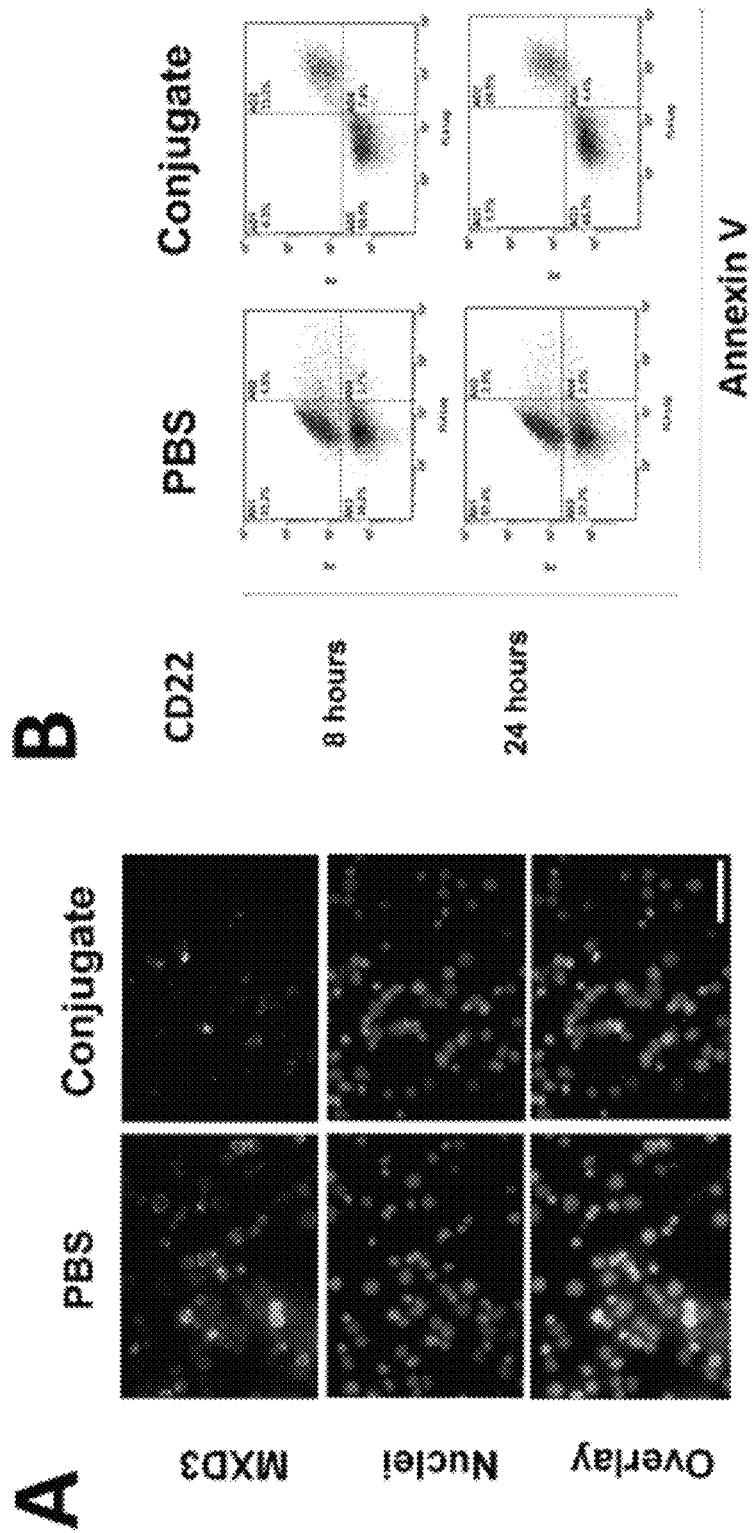
FIG. 9: αCD22 Ab-MXD3 ASO conjugate shows in vivo anti-leukemic effects against engrafted leukemia cells in mice. (A) The αCD22 Ab-MXD3 ASO conjugate treatment showed MXD3 knockdown in the engrafted Reh cells at 8 hours after treatment. MXD3 protein expression was measured in the cells harvested from BM. Images were acquired at 40× magnification/1.4 numerical aperture at room temperature using a Nikon Ti-U inverted microscope and NIS-Elements BR software. Scale bar indicates 50 μm. (B) The αCD22 Ab-MXD3 ASO conjugate treatment induced cell apoptosis in the engrafted Reh cells at 8 and 24 hours after treatment. Cells were stained for human CD22 and annexin V. Red dots (lower quadrants): murine cells (CD22 negative), purple dots (upper left quadrant): live Reh cells (CD22 positive annexin V negative), and blue dots (upper right quadrant): apoptotic Reh cells (CD22 and annexin V positive) in BM.
Figure 10:
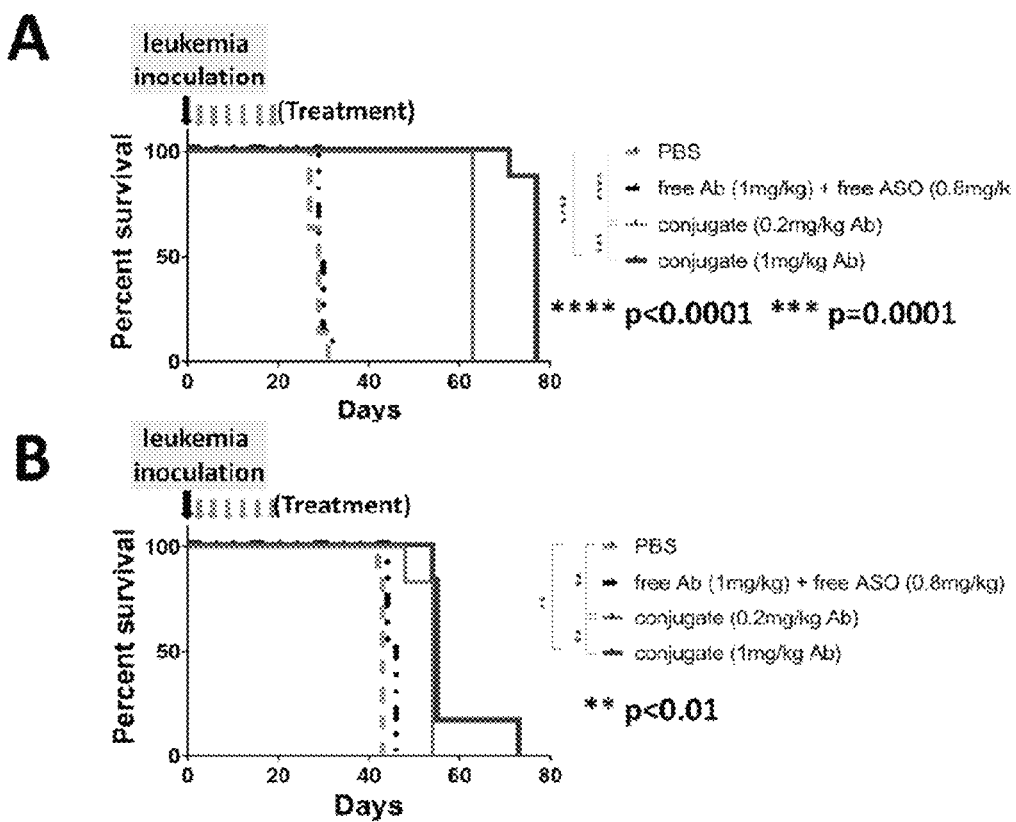
FIG. 10: αCD22 Ab-MXD3 ASO conjugate shows significant in vivo therapeutic efficacy in two human patient-derived leukemia mouse models. Kaplan-Meier survival curves for mice inoculated with two patient-derived leukemia cells (A and B). The mice were treated with PBS, free αCD22 Ab (1 mg/kg) plus free MXD3 ASO (0.8 mg/kg), and two different doses of the αCD22 Ab-MXD3 ASO conjugate (0.2 mg/kg or 1 mg/kg of the Ab). (A) PBS vs. conjugate at both doses (**p<0.0001). Conjugate 0.2 mg/kg vs. 1 mg/kg (of the Ab) (*p=0.0001) (n=8). (B) PBS vs. conjugate at both doses (p<0.01). Conjugate 0.2 mg/kg vs. 1 mg/kg (of the Ab) (p<0.01). (n=6).

We demonstrated leukemia-specific Ab-mediated ASO delivery that resulted in target knockdown, using αCD22 Ab as the vehicle for delivery of MXD3 ASOs, which was confirmed at the protein level. Although the mechanism of intracellular trafficking of the conjugated ASOs is unknown, our study provides proof of concept that αCD22 Ab effectively mediates leukemia cell-specific, intracellular delivery of intact ASO molecules both in vitro (FIGS. 3-5) and in vivo (FIGS. 7, 9, and 10). In this study, MXD3 protein knockdown was confirmed as early as 4 hours after ASO was added to the cells (FIGS. 3-5). We also observed the same early protein knockdown (measured at 8 hours after a single conjugate injection) in our in vivo study (FIG. 9A). The mechanism of action of the αCD22-ASO conjugate remains unclear since the rapid kinetics of MDX3 protein knockdown is not consistent with standard inhibition of MXD3 mRNA levels (data not shown). Interestingly, the same phenomenon (early MXD3 protein knockdown without confirmation of mRNA knockdown) was observed with several different MXD3 ASO sequences (data not shown), as well as MXD3 siRNA (47, 48), with or without αCD22 Ab as a vehicle. Furthermore, the same phenomenon was observed in neuroblastoma, a different cancer expressing high MXD3, with the same MXD3 ASOs or siRNA used for leukemia and nanoparticles as a vehicle (Satake et al., manuscripts in preparation). These data suggest a potential different mechanism of action in MXD3 knockdown, for example, ASO-specific translational inhibition without a reduction in MXD3 transcript levels (56-58). MXD3 is a transcription factor, with a short half-life of only up to 30 minutes in Reh cells (unpublished data). Further studies are necessary to assess the specific mechanism of MXD3 knockdown in leukemia cells.

αCD22 Ab has been used as a therapeutic (59-61) or therapeutic vehicle (17, 19, 61, 62); however, our study is the first to demonstrate its use as a vehicle for delivery of ASO for preB ALL. Backbone-modified free MXD3 ASOs used in this study demonstrated some in vitro therapeutic efficacy (data not shown). Our in vivo study also suggests that free ASOs may be more effective at higher doses (FIG. 5). However, this would allow non-specific delivery, increasing the potential for off-target effects. Our data support the hypothesis that αCD22 Ab provides effective leukemia cell-specific intracellular ASO delivery. While naked αCD22 Ab can be therapeutic as a single agent, it is very encouraging that the dose of the αCD22 Ab used in our in vivo studies was only about 1/20 of the previously described single agent (Ab alone) therapeutic dose (60, 63).

Our conjugate demonstrated consistent and striking in vivo therapeutic efficacy in a cell line-derived and in two high-risk patient-derived preB ALL xenograft models (FIGS. 7, 9, and 10). While there were slight differences in the CD22 surface expression and MXD3 expression levels in the two patient samples, the conjugate showed efficacy in both samples. Studies of αCD22 Ab-targeted therapy in CD22-positive lymphoma showed no correlation between efficacy and the level of target (CD22) expression (64, 65).

Figure 6:
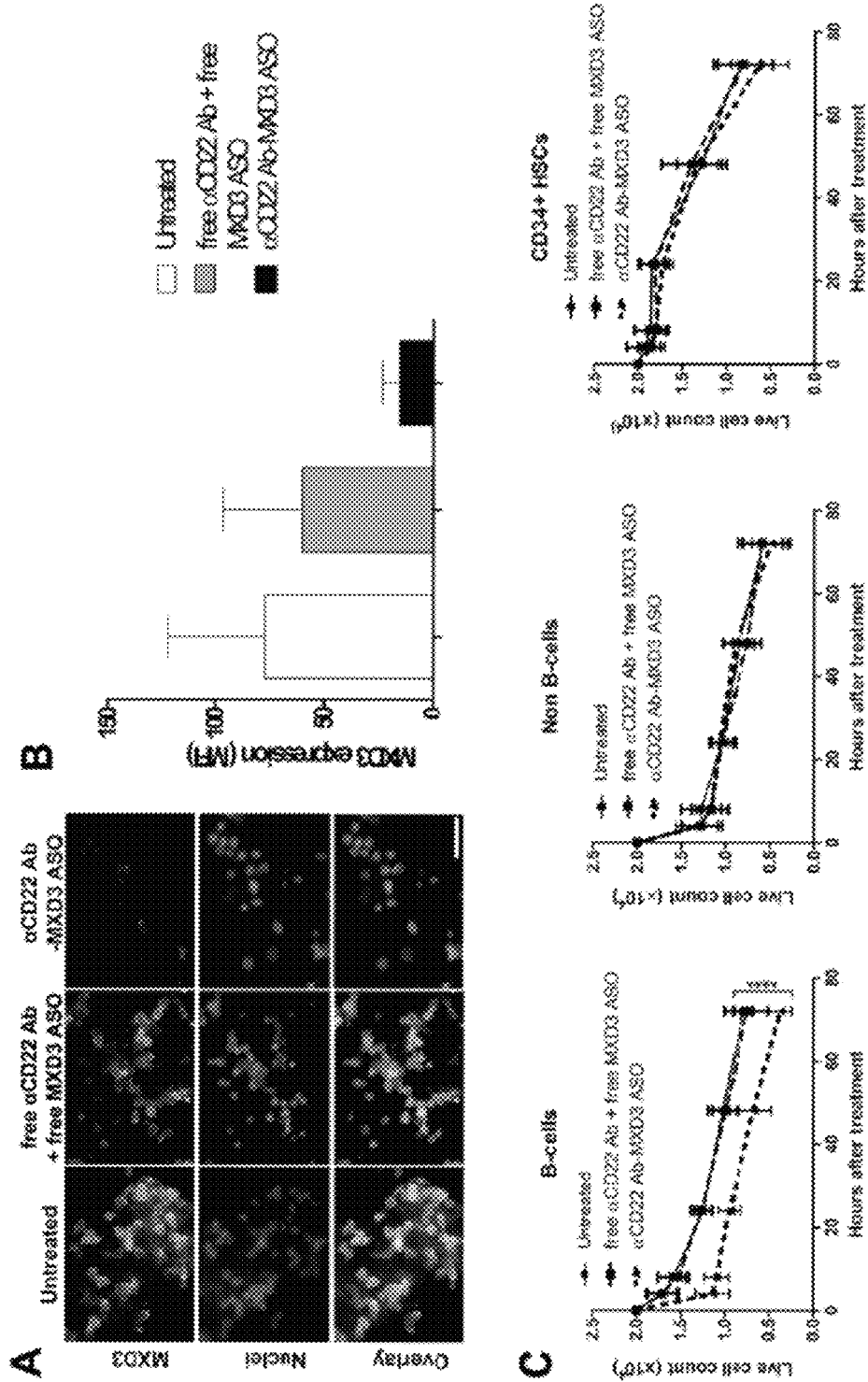
FIG. 6: αCD22 Ab-MXD3 ASO conjugate has cytotoxicity in normal B cells, but not in HSCs. (A) Normal B cells express low levels of MXD3 and treatment with the αCD22 Ab-MXD3 ASO conjugate showed knockdown. Images were acquired at 40× magnification/1.4 numerical aperture at room temperature using a Nikon Ti-U inverted microscope and NIS-Elements BR software. Scale bar indicates 50 μm. Free αCD22 Ab (azide-conjugated)+free MXD3 ASO also showed low levels of non-specific knockdown. (B) MXD3 protein knockdown quantified using MFI. Each bar represents the average MFI of all measured cells per treatment type from 2 independent experiments. Error bars represent SD (n=2). (C) Accelerated cell death in B cells treated with the αCD22 Ab-MXD3 ASO conjugate. Data points indicate mean values of independent cell counts in triplicate from 2 independent experiments. Data as mean±SD. The MXD3 αCD22 Ab-ASO conjugate vs. free αCD22 Ab (azide-conjugated)+free MXD3 ASO (****P<0.001).
Figure 8:
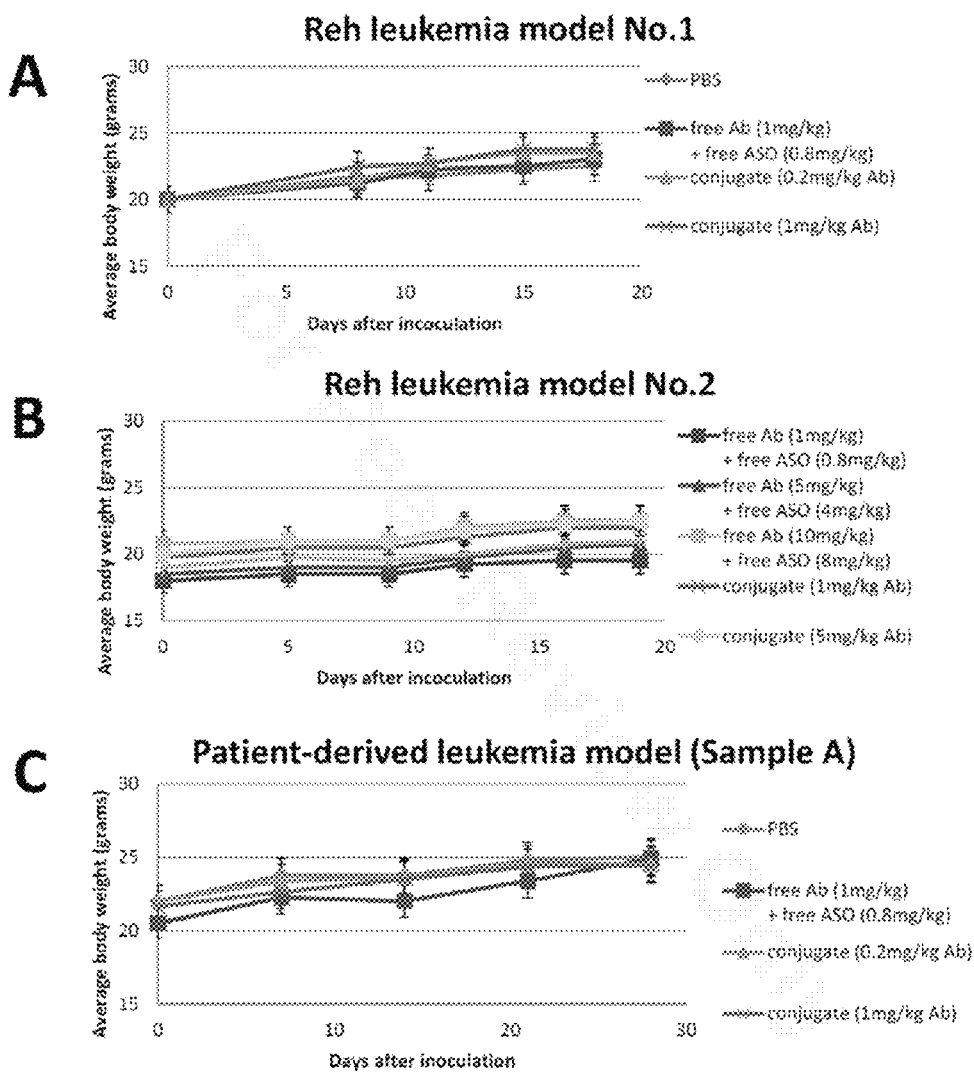
FIG. 8: Mice show stable weight gain during treatment. Average body weight of the mice during treatment in the two Reh (A and B) and the patient sample A (C) experiments. None of the mice lost weight during the treatments.

Assessment of off-target effects in murine models of human cancer is often limited by inter-species target heterogeneity; however, the MXD3 ASO used in this study targets the same sequence of human and murine MXD3 mRNA, allowing us to study off-target effects to some extent. It is promising that the treatment, including free MXD3 ASO, did not show any significant toxicities (FIG. 8 and FIG. 12). Our in vitro studies, as expected, showed that the conjugate affected normal human B cells, but not CD34+ HSCs (FIG. 6). Further studies, including in vivo studies using mice engrafted with human hematopoietic cells, are warranted to investigate potential off-target and side effects and optimize the dose and schedule of the conjugate. Although some B cell toxicity seems to be unavoidable, toxicity has been shown to be tolerable in other B cell-targeting agents, such as Rituximab (13, 66), CAR-based T cell therapies (23-25) and BiTE antibody (21, 22).

CONCLUSION

The results of the present study demonstrate the therapeutic efficacy and safety profile of a novel αCD22 Ab-MXD3 ASO conjugate in preclinical models of human preB ALL. The conjugate has multiple applications in conjunction with current drugs, other targeted therapeutics, and immunotherapies, such as CAR-based T cell or BiTE antibody therapies, to develop more effective and less toxic therapies for preB ALL. This work represents an important advance in technology that allows effective in vivo ASO delivery that can be modified for use in many cancers and other diseases.

REFERENCES

1. Pui C H, Mullighan C G, Evans W E, Relling M V. (2012) Pediatric acute lymphoblastic leukemia: where are we going and how do we get there? *Blood* 120: 1165-1174.
2. Schrappe M, et al. (2000) Long-term results of four consecutive trials in childhood ALL performed by the ALL-BFM study group from 1981 to 1995. Berlin-Frankfurt-Munster. *Leukemia* 14: 2205-2222.
3. Hunault M, et al. (2004) Better outcome of adult acute lymphoblastic leukemia after early genoidentical allogeneic bone marrow transplantation (BMT) than after late high-dose therapy and autologous BMT: a GOELAMS trial. *Blood* 104: 3028-3037.
4. Pui C H, Evans W E. (2006) Treatment of acute lymphoblastic leukemia. *The New England journal of medicine* 354: 166-178.
5. Faderl S, et al. (2010) Adult acute lymphoblastic leukemia: concepts and strategies. *Cancer* 116: 1165-1176.
6. Pui C H. (1995) Childhood leukemias. *The New England journal of medicine* 332: 1618-1630.
7. Pui C H, Robison L L, Look A T. (2008) Acute lymphoblastic leukaemia. *Lancet* 371: 1030-1043.
8. Pui C H, Evans W E. (2013) A 50-year journey to cure childhood acute lymphoblastic leukemia. *Seminars in hematology* 50: 185-196.
9. Schmiegelow K, et al. (2013) Second malignant neoplasms after treatment of childhood acute lymphoblastic leukemia. *Journal of clinical oncology: official journal of the American Society of Clinical Oncology* 31: 2469-2476.
10. Mody R, et al. (2008) Twenty-five-year follow-up among survivors of childhood acute lymphoblastic leukemia: a report from the Childhood Cancer Survivor Study. *Blood* 111: 5515-5523.
11. Bhojwani D, Pui C H. (2013) Relapsed childhood acute lymphoblastic leukaemia. *The Lancet. Oncology* 14: e205-217.
12. Daver N, O'Brien S. (2013) Novel therapeutic strategies in adult acute lymphoblastic leukemia—a focus on emerging monoclonal antibodies. *Current hematologic malignancy reports* 8: 123-131.
13. Thomas D A, et al. (2006) Chemoimmunotherapy with hyper-CVAD plus rituximab for the treatment of adult Burkitt and Burkitt-type lymphoma or acute lymphoblastic leukemia. *Cancer* 106: 1569-1580.
14. Sievers E L, Linenberger M. (2001) Mylotarg: antibody-targeted chemotherapy comes of age. *Current opinion in oncology* 13: 522-527.
15. Senter P D, Sievers E L. (2012) The discovery and development of brentuximab vedotin for use in relapsed Hodgkin lymphoma and systemic anaplastic large cell lymphoma. *Nature biotechnology* 30: 631-637.
16. Lewis Phillips G D, et al. (2008) Targeting HER2-positive breast cancer with trastuzumab-DM1, an antibody-cytotoxic drug conjugate. *Cancer research* 68: 9280-9290.
17. Wayne A S, et al. (2010) Anti-CD22 immunotoxin RFB4(dsFv)-PE38 (BL22) for CD22-positive hematologic malignancies of childhood: preclinical studies and phase I clinical trial. *Clinical cancer research: an official journal of the American Association for Cancer Research* 16: 1894-1903.
18. Wayne A S, FitzGerald D J, Kreitman R J, Pastan I. (2014) Immunotoxins for leukemia. 2470-2477 pp.
19. Kantarjian H, et al. (2012) Inotuzumab ozogamicin, an anti-CD22-calecheamicin conjugate, for refractory and relapsed acute lymphocytic leukaemia: a phase 2 study. *The Lancet. Oncology* 13: 403-411.
20. Younes A, et al. (2012) Phase I multidose-escalation study of the anti-CD19 maytansinoid immunoconjugate SAR3419 administered by intravenous infusion every 3 weeks to patients with relapsed/refractory B-cell lymphoma. *Journal of clinical oncology: official journal of the American Society of Clinical Oncology* 30: 2776-2782.
21. Topp M S, et al. (2011) Targeted therapy with the T-cell-engaging antibody blinatumomab of chemotherapy-refractory minimal residual disease in B-lineage acute lymphoblastic leukemia patients results in high response rate and prolonged leukemia-free survival. *Journal of clinical oncology: official journal of the American Society of Clinical Oncology* 29: 2493-2498.
22. Topp M S, et al. (2014) Phase II Trial of the Anti-CD19 Bispecific T Cell-Engager Blinatumomab Shows Hematologic and Molecular Remissions in Patients With Relapsed or Refractory B-Precursor Acute Lymphoblastic Leukemia. *Journal of clinical oncology: official journal of the American Society of Clinical Oncology* 32: 4134-4140.
23. Kochenderfer J N, Rosenberg S A. (2013) Treating B-cell cancer with T cells expressing anti-CD19 chimeric antigen receptors. *Nature reviews. Clinical oncology* 10: 267-276.
24. Kenderian S S, Ruella M, Gill S, Kalos M. (2014) Chimeric antigen receptor T-cell therapy to target hematologic malignancies. *Cancer research* 74: 6383-6389.
25. Maus M V, Grupp S A, Porter D L, June C H. (2014) Antibody-modified T cells: CARs take the front seat for hematologic malignancies. *Blood* 123: 2625-2635.
26. Manoharan M. (2002) Oligonucleotide conjugates as potential antisense drugs with improved uptake, biodistribution, targeted delivery, and mechanism of action. *Antisense & nucleic acid drug development* 12: 103-128.
27. Juliano R, Alam M R, Dixit V, Kang H. (2008) Mechanisms and strategies for effective delivery of antisense and siRNA oligonucleotides. *Nucleic acids research* 36: 4158-4171.
28. Kurreck J. (2003) Antisense technologies. Improvement through novel chemical modifications. *European journal of biochemistry/FEBS* 270: 1628-1644.
29. Crooke S T. (2004) Progress in antisense technology. *Annual review of medicine* 55: 61-95.
30. Bennett C F, Swayze E E. (2010) RNA targeting therapeutics: molecular mechanisms of antisense oligonucleotides as a therapeutic platform. *Annual review of pharmacology and toxicology* 50: 259-293.
31. O'Brien S, et al. (2009) 5-year survival in patients with relapsed or refractory chronic lymphocytic leukemia in a randomized, phase III trial of fludarabine plus cyclophosphamide with or without oblimersen. *Journal of clinical oncology: official journal of the American Society of Clinical Oncology* 27: 5208-5212.
32. Chi K N, et al. (2005) A phase I pharmacokinetic and pharmacodynamic study of OGX-011, a 2'-methoxyethyl antisense oligonucleotide to clusterin, in patients with localized prostate cancer. *Journal of the National Cancer Institute* 97: 1287-1296.
33. Kastelein J J, et al. (2006) Potent reduction of apolipoprotein B and low-density lipoprotein cholesterol by short-term administration of an antisense inhibitor of apolipoprotein B. *Circulation* 114: 1729-1735.
34. Agarwala A, Jones P, Nambi V. (2015) The role of antisense oligonucleotide therapy in patients with familial hypercholesterolemia: risks, benefits, and management recommendations. *Current atherosclerosis reports* 17: 467.

35. MacLeod A R. (2013) Antisense therapies for cancer: Bridging the pharmacogenomic divide. *Drug Discovery Today: Therapeutic Strategies* 10: e157-e163.
36. Juliano R L, Ming X, Nakagawa O. (2012) Cellular uptake and intracellular trafficking of antisense and siRNA oligonucleotides. *Bioconjugate chemistry* 23: 147-157.
37. Castanotto D, Stein C A. (2014) Antisense oligonucleotides in cancer. *Current opinion in oncology* 26: 584-589.
38. Moreno P M, Pego A P. (2014) Therapeutic antisense oligonucleotides against cancer: hurdling to the clinic. *Frontiers in chemistry* 2: 87.
39. Walker I, Irwin W J, Akhtar S. (1995) Improved cellular delivery of antisense oligonucleotides using transferrin receptor antibody-oligonucleotide conjugates. *Pharmaceutical research* 12: 1548-1553.
40. Uckun F M, Qazi S, Dibirdik I, Myers D E. (2013) Rational design of an immunoconjugate for selective knock-down of leukemia-specific E2A-PBX1 fusion gene expression in human Pre-B leukemia. *Integrative biology: quantitative biosciences from nano to macro* 5: 122-132.
41. Nitschke L. (2005) The role of CD22 and other inhibitory co-receptors in B-cell activation. *Current opinion in immunology* 17: 290-297.
42. Tedder T F, Poe J C, Haas K M. (2005) CD22: a multifunctional receptor that regulates B lymphocyte survival and signal transduction. *Advances in immunology* 88: 1-50.
43. Boue D R, LeBien T W. (1988) Expression and structure of CD22 in acute leukemia. *Blood* 71: 1480-1486.
44. Grandori C, Cowley S M, James L P, Eisenman R N. (2000) The Myc/Max/Mad network and the transcriptional control of cell behavior. *Annual review of cell and developmental biology* 16: 653-699.
45. Yun J S, Rust J M, Ishimaru T, Diaz E. (2007) A novel role of the Mad family member Mad3 in cerebellar granule neuron precursor proliferation. *Molecular and cellular biology* 27: 8178-8189.
46. Barisone G A, Yun J S, Diaz E. (2008) From cerebellar proliferation to tumorigenesis: new insights into the role of Mad3. *Cell cycle* (Georgetown, Tex.) 7: 423-427.
47. Satake N, et al. (2014) Targeted therapy with MXD3 siRNA, anti-CD22 antibody and nanoparticles for precursor B-cell acute lymphoblastic leukaemia. *British journal of haematology* 167: 487-499.
48. Barisone G A, et al. (2014) Loss of MXD3 induces apoptosis of Reh human precursor B acute lymphoblastic leukemia cells. *Blood cells, molecules & diseases*.
49. Seth P P, et al. (2009) Short antisense oligonucleotides with novel 2'-4' conformationaly restricted nucleoside analogues show improved potency without increased toxicity in animals. *Journal of medicinal chemistry* 52: 10-13.
50. Agard N J, Prescher J A, Bertozzi C R. (2004) A strain-promoted [3+2] azide-alkyne cycloaddition for covalent modification of biomolecules in living systems. *Journal of the American Chemical Society* 126: 15046-15047.
51. Engel P, et al. (1993) The same epitope on CD22 of B lymphocytes mediates the adhesion of erythrocytes, T and B lymphocytes, neutrophils, and monocytes. *Journal of immunology* (Baltimore, Md.: 1950) 150: 4719-4732.
52. Pizzo P A, Poplack D G. (2011) Chapter 19 Acute Lymphoblastic Leukemia. Principles and practice of pediatric oncology 6$^{th}$ edition. Lippincott Williams & Wilkins, Philadelphia, pp. 543.
53. Kato J, et al. (2013) Efficacy of a CD22-targeted antibody-saporin conjugate in a xenograft model of precursor-B cell acute lymphoblastic leukemia. *Leukemia research* 37: 83-88.
54. McManus M T, Sharp P A. (2002) Gene silencing in mammals by small interfering RNAs. *Nature reviews. Genetics* 3: 737-747.
55. Chan J H, Lim S, Wong WS. (2006) Antisense oligonucleotides: from design to therapeutic application. *Clinical and experimental pharmacology & physiology* 33: 533-540.
56. Brown-Driver V, Eto T, Lesnik E, Anderson K P, Hanecak R C. (1999) Inhibition of translation of hepatitis C virus RNA by 2-modified antisense oligonucleotides. *Antisense & nucleic acid drug development* 9: 145-154.
57. Youssef S S, et al. (2014) In Vitro Inhibition of Hepatitis C Virus by Antisense Oligonucleotides in PBMC Compared to Hepatoma Cells. *BioMed research international* 2014.
58. Tallet-Lopez B, et al. (2003) Antisense oligonucleotides targeted to the domain IIId of the hepatitis C virus IRES compete with 40S ribosomal subunit binding and prevent in vitro translation. *Nucleic acids research* 31: 734-742.
59. Carnahan J, et al. (2007) Epratuzumab, a CD22-targeting recombinant humanized antibody with a different mode of action from rituximab. *Molecular immunology* 44: 1331-1341.
60. Raetz E A, et al. (2008) Chemoimmunotherapy reinduction with epratuzumab in children with acute lymphoblastic leukemia in marrow relapse: a Children's Oncology Group Pilot Study. *Journal of clinical oncology: official journal of the American Society of Clinical Oncology* 26: 3756-3762.
61. Hochberg J, El-Mallawany N K, Cairo M S. (2014) Humoral and Cellular Immunotherapy in ALL in Children, Adolescents, and Young Adults. *Clinical lymphoma, myeloma & leukemia* 14s: S6-s13.
62. Mussai F, et al. (2010) Cytotoxicity of the anti-CD22 immunotoxin HA22 (CAT-8015) against paediatric acute lymphoblastic leukaemia. *British journal of haematology* 150: 352-358.
63. O'Donnell R T, Ma Y, McKnight H C, Pearson D, Tuscano J M. (2009) Dose, timing, schedule, and the choice of targeted epitope alter the efficacy of anti-CD22 immunotherapy in mice bearing human lymphoma xenografts. *Cancer immunology, immunotherapy: CII* 58: 2051-2058.
64. Li D, et al. (2013) DCDT2980S, an anti-CD22-monomethyl auristatin E antibody-drug conjugate, is a potential treatment for non-Hodgkin lymphoma. *Mol Cancer Ther* 12: 1255-1265.
65. Pfeifer M, et al. (2015) Anti-CD22 and anti-CD79B antibody drug conjugates are active in different molecular diffuse large B-cell lymphoma subtypes. *Leukemia*.
66. McLaughlin P, et al. (1998) Rituximab chimeric anti-CD20 monoclonal antibody therapy for relapsed indolent lymphoma: half of patients respond to a four-dose treatment program. *Journal of clinical oncology: official journal of the American Society of Clinical Oncology* 16: 2825-2833.

What is claimed is:

1. A compound comprising one or more modified oligonucleotides and an anti-CD22 antibody, wherein the one or more modified oligonucleotides comprise:
   16 linked nucleosides having a nucleobase sequence of the sequence recited in SEQ ID NOs: 5, 6, 7, 8, 9, 10, 11, 12, 13, 14, 15, 16, or 17;
   a gap segment consisting of ten linked deoxynucleosides;
   a 5' wing segment consisting of three linked nucleosides; and
   a 3' wing segment consisting of three linked nucleosides;
   wherein the gap segment is positioned between the 5' wing segment and the 3' wing segment; wherein each nucleoside of the 5' wing segment comprises a (S)-cEt sugar modification; wherein each nucleoside of the 340 wing segment comprises a (S)-cEt sugar modification; wherein each internucleoside linkage is a phosphorothioate linkage; and wherein each cytosine is a 5-methylcytosine.

2. The compound of claim 1, wherein the one or more modified oligonucleotides consist of:
   16 linked nucleosides having a nucleobase sequence of the sequence recited in SEQ ID NOs: 5, 6, 7, 8, 9, 10, 11, 12, 13, 14, 15, 16, or 17;
   a gap segment consisting of ten linked deoxynucleosides;
   a 5' wing segment consisting of three linked nucleosides; and
   a 3' wing segment consisting of three linked nucleosides;
   wherein the gap segment is positioned between the 5' wing segment and the 3' wing segment; wherein each nucleoside of the 5' wing segment comprises a (S)-cEt sugar modification; wherein each nucleoside of the 3' wing segment comprises a (S)-cEt sugar modification; wherein each internucleoside linkage is a phosphorothioate linkage; and wherein each cytosine is a 5-methylcytosine.

3. The compound of claim 1, wherein the one or more modified oligonucleotides consist of ISIS 632407, ISIS 632407, ISIS 632417, ISIS 632424, ISIS 632460, ISIS 632461, ISIS 632527, ISIS 632528, ISIS 632634, ISIS 632640, ISIS 632669, ISIS 632672, ISIS 632673 or ISIS 632682.

4. The compound of claim 1, wherein the one or more modified oligonucleotides consist of ISIS 632461.

5. The compound of claim 1, wherein the compound comprises the anti-CD22 antibody and 2-4 modified oligonucleotides.

6. The compound of claim 1, wherein the compound consists of the anti-CD22 antibody conjugated to 2-4 modified oligonucleotides.

7. The compound of claim 1, wherein the one or more modified oligonucleotides are conjugated to the anti-CD22 antibody at a 5' end.

8. The compound of claim 1, wherein the one or more modified oligonucleotides are conjugated to the anti-CD22 antibody through a linker comprising an oligoethyleneglycol moiety.

9. The compound of claim 1, wherein the one or more modified oligonucleotides are conjugated to the anti-CD22 antibody through a linker comprising a triethyleneglycol moiety.

10. A method of treating a B-cell disease, comprising contacting a cell with the compound of claim 1.

11. The method of claim 10, wherein the B-cell disease is leukemia, precursor B-cell acute lymphoblastic leukemia, or lymphoma.

12. The method of claim 10, wherein the B-cell disease is a B-cell mediated autoimmune disease.

13. The method of claim 10, wherein the method comprises contacting the cell with one or more chemotherapy agents.

14. The method of claim 13, wherein one of the one or more chemotherapy agents comprises vincristine.

15. The method of claim 13, wherein one of the one or more chemotherapy agents comprises doxorubicin.

16. The method of claim 13, wherein the one or more chemotherapy agents comprise vincristine and doxorubicin.

* * * * *

SEQUENCE LISTING

<160> NUMBER OF SEQ ID NOS: 18

<210> SEQ ID NO 1
<211> LENGTH: 37001
<212> TYPE: DNA
<213> ORGANISM: Homo sapiens

<400> SEQUENCE: 1

| | | | | | |
|---|---|---|---|---|---|
| gtgcccagtc | ttagctgggg | agagaagaga | ggtctgtggg | gcaggggccg | tgctggggtt | 60 |
| gcctccagct | tgctggaagg | ccctggggag | ctctgagcag | cccattctgc | tctccctcca | 120 |
| gccgtgcttc | ctcaaagact | gggaaatgca | cgtccacttc | aaagtccacg | gcacagggaa | 180 |
| gaagaacctc | catggagacg | gcatcgcctt | gtggtacacc | cgggaccgcc | tcgtgccagg | 240 |
| tgggctggtg | ttcgctcagc | tgggccctgt | ggggtgggc | acgggcatgg | ctgctggccc | 300 |
| cctagggagg | tggggtgggg | ctgcctgtgg | ctcgtgggga | ccagcgtctc | ctctcctgtt | 360 |
| aggaaagtgc | tgcctcccgt | ggataaagtc | ctgcgcctcc | ggaaggagcc | tggctctgga | 420 |
| aggaaggtca | ctgaggggag | aggagcagct | gggtcctgca | gctcaaccct | acaccctcat | 480 |
| tggcctggtt | ttaccatttt | aaacagttat | tgttgtaaaa | aagccaaaac | atgaagactg | 540 |
| tgtggctgtg | actgcatgtg | gcccacagac | cctgaggtgt | tccttggtg | gctcttcaca | 600 |
| gaatgtttgc | tgcccctagt | atagagggta | gagcctcctg | ggtagggctg | tcctgtggct | 660 |
| cactgttttt | tgtaggccag | gtaccccctt | gacacctgac | atctgcctca | gtcccctcac | 720 |
| agttcagcct | tcaaacttga | gtcctctgtg | tcatatgcct | agaccccca | cttctgagga | 780 |
| gaaagcctca | gctttctcct | ttcacgatcc | cttctctctc | ggtgaatggc | cagtgggttg | 840 |
| ggctctcttg | cccccaccca | tgttggcatt | gcttgccttt | taggtaccca | tgggacggct | 900 |
| cctgtttctc | ccattctgag | agcatctgct | tataattcta | gggcctgtgt | ttggaagcaa | 960 |
| agataacttc | cacggcttag | ccatcttcct | ggacacctac | cccaatgatg | agaccactga | 1020 |
| ggtaggcccc | tgctctatcc | tgctgagcag | gaaaggaagg | actgggcagt | cggctagagg | 1080 |
| aggggggccct | gggacttcca | tggtcccagc | acaagaggag | cctccaggga | ttggggtggt | 1140 |
| gggtgcccct | gctcgcccca | caggctgggc | tgcttgtgga | gtaaccgatg | tcttggtccc | 1200 |
| agcgcgtgtt | cccgtacatc | tcggtgatgg | tgaacaatgg | ctccctgtcc | tacgaccaca | 1260 |
| gcaaggatgg | gcgctggacc | gagctggcgg | gctgcacggc | tgacttccgc | aaccgcgatc | 1320 |
| acgacacctt | cctggctgtg | cgctactccc | ggggccgtct | gacggtgagc | aggctaggcg | 1380 |
| gtggggggtgg | cagctggtgg | ccctgtgctg | gtcccacaga | ggctcaggag | ggcaggctgc | 1440 |
| tgtcctgcga | ggtgcttagc | gtgctgggcc | ctgcaggtga | tgaccgacct | ggaggacaag | 1500 |
| aacgagtgga | agaactgcat | tgacatcacg | ggagtgcgcc | tgcccaccgg | ctactacttc | 1560 |
| ggggcctccg | ccggcaccgg | cgacctgtct | ggtgagtggg | ccgggccagg | cgttggttcc | 1620 |
| cagcccagct | caccctgagg | gactgggagc | tttccatgca | gttgattgcc | tgccttcatg | 1680 |
| tggtttctga | gctcacctgg | ctgtgttcct | cctcctcctt | tcttctgtaa | atggcctgtc | 1740 |
| cgggcctcag | ttcctgtggt | ttctgggctc | acctggctgt | gttcctcctc | ctcctttctt | 1800 |
| ctgtaaatgg | cctgtccggg | cctcagttcc | tgtggtttct | gagctcacct | ggctgtgttc | 1860 |
| ctcctcctcc | tttcttctgt | aaatggcctg | tccgggcctc | aggccttgaa | cggtcccttg | 1920 |
| gcaaccttcc | ccatcaacag | gaggcagcgg | gtcagttaga | tttgggcaat | gtagattccc | 1980 |
| agatttatct | ccagcccaga | ccgctctgga | cctgctcagc | ccttgtgccc | acagctgagg | 2040 |
| ccacatcttg | cccatcggga | tgtcagtggc | acctgtgccc | ctctatttgc | ttgctgtctt | 2100 |

```
tccggaccct tctttctctc acatggcacc tctggtccat caacagtccc tgtggcttta    2160
ttttcacagc acgtctcacc acttccctcc cctccctgac tacctggcgg cttcaggcca    2220
ccagtgtctc tcacaggagt ctcccaagtg gtccctcct tcaccagccc caacagtct      2280
ctcgtgagca cagcagccgt gtaatcgcct tcagtaatcg ccttcagccc gtgtgaggcc    2340
tcctgctgct ctgcgcagag ctctgcaggg ggcgccaggg cctctgtgcc agccctgcca    2400
cctctggctc cctgctcact gctcccctg cctactgtgg cttccagctg ctgcctggat     2460
gcgcctgtgc cctcctgccc cggctgtttc acccttgtct cctagggcct tgctcagatg    2520
ttacctcctc agtgcggcct tccctgatgc cctcgtggaa tgtcgtgccc cctcctgtgt    2580
ccccagccca ctccccagca tctttgctgg ctttattttt cttcataata tttaccatct    2640
ttgagtctac cgagtaatta attttattgt ctctggccct cctgctcaat tgtaagctct    2700
ataaatggct gtttggccca gggcaggtgc tcagcgagca ctggggtgcc tctaacctgc    2760
tcaggcctca ctggtcacca ggccgtggtg gcccttggct gtggttctcg gtttctcttt    2820
ggggccctga gcaggtgcca ggcccagggc cagctcctga ccagaactgg cacgtgacac    2880
gggggacctg acatgggcgg tttatcctca ggatgaccca ttccagggcc tgtagtctgc    2940
ccactgccca ggagcctcct ctctcagcat ggaagtgctt gggtccgctc agaccccaga    3000
acatccattg tttgggggtt tttcagtcac atacccagca gaggagagag gtctggtaag    3060
cacccttcct gccaaccagc tttcatcatt tccagctcgc gcctggctgg tttccctcct    3120
gccccgggtt gcctggaact tcatcacact gtttcagccc ttgtctttgg agggttcttg    3180
ataggagcag agcagcacca gtgctgtggc cggtggcagc tctcacagct gttgggagag    3240
cccagcacag agtggaggag gcaccatgag gggagccgtg tctgaccact ggtcaggggt    3300
catcagtgcc aggcacctta cgggtgatgt cacctgatgt attttaggc agatggccat     3360
ctcgttccct ttttactcaa ccattgggag tttgaaaact gaaaggattt ttcctaagat    3420
acgagcagga agcagcagag cccagatggg aactggggcc tgactccagg gccggtcctt   3480
gtcctgcagg gccgctcgcc gtctccaagg gctgtgcatg ctcggctctc acactgtgtg    3540
cctggccgag ctcttgctca ttaggtcccc ccttggctcc agagattcct gctcccttca    3600
acaaggcctt tcctcagatt ccagtcccag gctgaccagg acccacgtgt cggctttgag    3660
cctcagcctc ctcatctcta caattgggtg atccatcagc gtcaagccag gctcttccc    3720
tgtgcatgcc attggacaga gccttttccc agtctcctca ggcacagctg ctgacctgcg    3780
ttaggctcag gcccttagct ggttgccgag ttgttcccct gcagcctgta tgtgggtctc    3840
tgtggcaaga atgtctggtg gctcctgccc ttgggacctc agccttctca gccagtcaca    3900
cagcgactgt tggtctttcc cgggtctgtt tttgagcact tattctgcag gcaggccatc    3960
ttctgtgtgg tgtagaccct tctcatgtac ttgccatggc aaccacacag atggagatca    4020
tcactcctct acatgtgcgg aacatgagcc tcaaagaggg cggcagaccc caggatttag    4080
acccagatga ttctgcttgt aaagccctta ctgttttctc tccactctgc ctcctctctt    4140
ttttattgct ggtgactgga gggagctggg aagaaaacag gccctagccg gctgggcagt    4200
gctctccca ggggcctggc aggtttactg gctgcagcag cagcttttcct tgtgggaggg    4260
tcttgggcca cgtgccctgc ggctggcctg taggctgtca caggtttatt cttggtcctg    4320
cagacaatca tgacatcatc tccatgaagc tgttccagct gatggtggag cacacgcccg    4380
acgaggagag catcgactgg accaagatcg agcccagcgt caacttcctc aagtcgccca    4440
```

| | |
|---|---|
| aaggtgcgtg tgcacagccc cgccctgcct gggcctgggc ggcctgaccc agaatggggt | 4500 |
| gaagccagcc tggcgggtct tgtggtccag tcgtggttgt ggtggttgtg gtctgggctc | 4560 |
| ttggatcagc ccggtcctgg caagcggcac tggctggccc tgtccgagct cctagagtat | 4620 |
| tgggcttgga tcgtgtcagc tctggcaagt ttttgagtaa atgaatgagg cggaagagaa | 4680 |
| gtctgcagag agtcagtccc tgaggacatc ctagtcacgt gagtgctgtg gcagcaagca | 4740 |
| gtggctgatc aacaaacgtg tgagtggtgg gccagcatcc tccctcacta ggtgctgggg | 4800 |
| cagtggccag cagagccagg gggctgggta tgttggccca cctgtccctt ctgtgagcca | 4860 |
| cctggaagaa gtcgtgctgc tggtcaaggg ggtggattcc ttagctagaa ggagagagag | 4920 |
| agcaagattg gaaattgggt ttctacaaaa cccgaagcct gggttcttcc catggcacta | 4980 |
| attagctacc cctttcctca cagagtgaac gttgtggttg gaggaatgag gcatctgtgt | 5040 |
| gtggagaagt ccaccctaag agccacagat gtgtgcctgg gggtccagcc agtgacagaa | 5100 |
| gtgcacggcg cgggctctgt cgtagcccag ccctgggtcc ccatgccgtg tgggccagtt | 5160 |
| tggccgcgtg tttctgcttt tcaggagaag ccaagatcca gtgttttatg tgacagttca | 5220 |
| ctttttaaag attcagatta ttttgaaatg ttttggggac cacacaaacc ttgctgcaac | 5280 |
| ctttggtcag aaggctgcca gctgctgggt gtttgcagag gtggcacctg ccttgcccac | 5340 |
| ccagcatccc gtgcagctgg caaggcagga tgaactcgtt tttagattca atccatttgt | 5400 |
| tccttcagat gtgaccaaag ctgccctctg tgcctagcca tgggctgggt gctggagaca | 5460 |
| cgagatcagg caggccctgc cctgggggct cattctaggg tctgcggcag acaggagac | 5520 |
| agagggagct gtgagagccc tgaggctgag tggctttctg gggaagcacc atccctaggg | 5580 |
| acctccgcgt tcggtcagtg gccgctgctg tcggtgtgca gagcagaggc tggggcgaga | 5640 |
| gtggtcagca ggcctgctgg tggcagcttg tgcaggaagg gaggatggag gttggcttgt | 5700 |
| ggctggcaag agggtggcat gcacgtcgct gaaaggcagg gcctgggccc gaggcctggg | 5760 |
| tgtggggacg cctgaggaga ctgtacagtg tggagtcggg ggggccgcag tcagggaggg | 5820 |
| aggcagagtg gcagaaacag ggcccagcca daccccagct cctccaccca cagcctggag | 5880 |
| agcttgggaa agtcagtgtc ttctctccgc ctgtacaagg gagcgtacca gtgggccca | 5940 |
| tcccaggatg ggcaggacct gtgggaacct tgtgtggagg agagaggctg tgggctgggg | 6000 |
| tggagtgtgg gactcaggtc ctgggagacc ctcctggggg gctgccgaga gcatccagct | 6060 |
| gtgggctggg agagcctgtg accagggccg cgctgctcca gaaagggccc tcagaccaca | 6120 |
| gcgtgggggt ggggcttgga tatgtagact cctgggcctc cccttatcca gagttggact | 6180 |
| cagaggagcc caggagtctg gttttaactg gcttcctgca gcagaaggca gcccaggctt | 6240 |
| gtcgctgggg tcccgggtcc ctgtgggctt ggtcctctct ctgccccacc ctgccctggg | 6300 |
| gactgcagag ctggctggga tgggcttcac ctgacctctg cccctccccg gtgagggggg | 6360 |
| tgagtacgac cggcctgccc accgtggccg gctgtcctgt tccatcccca ctgccctcct | 6420 |
| gcagcccct gatcccggc ccgtgctgcc gtttcagctc ccccgtttct tctcccccag | 6480 |
| acaacgtgga cgaccccacg gggaacttcc gcagcgggcc cctgacgggg tggcgggtgt | 6540 |
| tcctgctgct gctgtgcgct ctcctgggca tcgttgtctg cgccgtggtg ggggccgtgg | 6600 |
| tgttccagaa gcggcaggag cggaacaagc gcttctactg agtggcgcct ccggcggggc | 6660 |
| ctgtccctgg gccaggagc caatgtgaac tttttttttt accgggatta taaagaaca | 6720 |
| acaagatgac cttatttctt aactgtttca aataaatgat taaagtattt tcatacattt | 6780 |
| tgcttcttgc ccagcaggga caggtggcag agccgaggct tagggtctgg caccccccac | 6840 |

```
agctggagac ggaggctctc ctggggctgg tgtctcagga gcaggggtct gtgtctacag    6900
atgggctgtg gccsctgcag gcagctgttg aacactggag ggtcccccgg accacactgg    6960
```



```
agctggagac ggaggctctc ctggggctgg tgtctcagga gcaggggtct gtgtctacag    6900
atgggctgtg gccsctgcag gcagctgttg aacactggag ggtcccccgg accacactgg    6960
ggtgggctcc tgaggacgtg gggaagtgat tttgttttgt ggtgtgtggc acgtgtggcg    7020
acggataagg cctgaactgg gaaacccagg ccttcctgtt caccctgagc tgcttcctga    7080
gacagatgct caagtgaggc tgcaggcgcg gtgtggtggg gccgagtgtg accgtttgct    7140
aaataaagtg aaatacccaa cctcagccgt gtgactgtcc tgaggggctt gctttgcttt    7200
ctcttctaat gacttccagc ccgccagtgc tttagagctt tcagctcgtc tgctctgacc    7260
tgcagagtcc cggaggatgg gatgggttgc cctgtttccc agctggggac acacggctct    7320
cagaggtcaa gtacagcttg cccagtgtca cctggcaagt gatgttttgg ggatggggcc    7380
ctgtgctgtc tcccacatgc tctgggcctc tgggtaaaag gatgggtggt aaggggcacc    7440
acgtggaggc ttggctgggc aggcgggtac actgacgggg aactccgggg ggctctggga    7500
tgatgtgcaa ggggctggag gatggtgggg gtggttgtgg cagtcccttt ggggcacctc    7560
aggggacaaa gatgataacg gggagtggag gaaaggcagc agctgaaggc atggcaccac    7620
ccccggcagc ttccataatc gtcgccccca gctgtggctg cctccacctc gcgccgtgga    7680
gcagcatgtc ccgtcccgtc ccaagccacc cctctggctc tgatcccaac tctagccctc    7740
cttggacacc ttgctgagcc gatgatcttg tcttcctcgt cccttccca ctccccgttc     7800 agttgcattt gaatctccca cctagaagc cagccgtccc tcctttcagc agccaggctt      7860
ttggtaatta acactatcaa acagattatc attgcaaaaa atatagagag acatgagtga    7920
gagtaaggac tttaccctct gtctctcatt ctccagagct cttcactggt ccactgtcac    7980
ccgcctctcg tgtcctctgt gtttcctcct tcaacaggtt agacgtctag agattccaca    8040
cagtgactga gaggttcgag tttgtgctgc tttcacgggt ttgggagcct gttcgtgaag    8100
cctgaagagt aatcatgatc ctccttattg aagtatttta ttaacacttt tcccaaagca    8160
gttcctttcc ttgaaaaggt agcagatcgt gtgtttatga caggccctgc ttcggagcga    8220
ttgaggcaca taactcattt catccacgac gctcacctgt caggtgctgg agggctttag    8280
gccaggtgtg tagagccgag gcccagagac gagctctcca cggctgctac aatcacgtca    8340
tcggcaccac gctcaccagg cttcaccttt aattttggc tctaaattgg tcttcaccga     8400
attcctgaat tactaggcca attagtgtcc catactagat ggttctcagc cttggctgtg    8460
tattggagtt ccctggagaa ctgagaagag cctgccttct tctccagttc tggctgagtg    8520
tgtcaggtgg agctggggca agggtggctt caaaagcccc tgcagtggtt ttaacaggta    8580
cccaagcttg agcacaagac ggagttaggg cccatgctgt ggcagcaggt gttaaaggtc    8640
ccacgctgtg gcagcaggtg ttaaaggtcc cacgctgtgg cagcaggtgt taaaggtccc    8700
atgctgtggc agcaggggtt aaagtgatcg tgccggtctc tacttggctg tcacggtggg    8760
cacccctttc cattggaaca tagccttgtt gtacctaaga aaagttgatt gtttcaaaat    8820
tcatacctag aggtgcttcc ctagaacgat cgatgtgtat tctgacatcc gcatttcaca    8880
cacgcaggac cgtgatgcca tagtctatgt ttttgccatg tgtgtctaaa aatttgaggt    8940
atttcatcat acaaaagtta aacgtgaatg tgtggctatg gacctgccgt gcgacgtgag    9000
aaatatcacg gacgcacttg gatccctctg tctcctcctg ccaaaggtga ttgctgcagg    9060
atctgacttt ttgtgtctgt ctgaaaattt ttaccacagg gatatgtatc tctacataca    9120
ttgtattgtt ttgaatttct gaagactaag tggtacatgg acgtattcct caacttttgc    9180
```

```
aattcagcat ggttggtgag tctttggatt acatgtggct caagatgggt gtttctcact    9240
gtgaggtatg aacagactcc agtttctcca ttctgctgct gattggaggt ggtttagggc    9300
ttttgctctg ctacatgata ctgctctaag cactcctgga tgtgtcttat ttatttattt    9360
atttatttat ttatttttga dacagagtct taaactctgt tgcccaggct ggagtgcagt    9420
ggcacagtct ggctcactg caacctctgc ttcctgggtt caagcgattc tcctgcctca    9480
gcctcccgag tagctgggac tacaggtgtg caccaccatg cctggctaat ttttgtattt    9540
ttagtagaga aagggtttca tcacgttggc caggctggtc tcgaactcct gacctcaagt    9600
gatccacccg tctcagcttc ccaaactgct gggattacag gcgtgagcca ccgcacccag    9660
cccattttca gttttactag agggtgcctc gctgctctcc aaatcgggcc gtgaccacag    9720
tggggtggca cctgccgaga tcccctctgt ccctcagcac ctgatatagt cagagctttc    9780
cattttgac aggtggatgc aaaagctttc gtttgtttct ctgctagcca tgttgggatg    9840
tgtgtgcgtt tattggcatc tgtgtttctg tgtggtggtt tagtccgggc cctttcttcc    9900
ggccgtgtag gagtgcctgt gcggggctcc tctggtgata tgcccttggc gcataccttc    9960
cagtgtgcct gggggctttt gcttttcaat gacgtcattt gatatacagc ctataattta   10020
gtgtgatttc ataatctatt ctaaagattt tgttttttgct taaaagcttt aaaatttgc   10080
ttttcaaatt tggcatttaa tcgaagtgga gttaagctgg cgtagggtgt gatgtaggga   10140
atccattttt ccaattgtct ccagccagtt ccagcaccat ttaccgaccc ctgggtcctt   10200
ctgcaccctc tgaggcgcac actcaggtgg ccacgccaca tctgctccta accctgcccc   10260
tcagcttcct cccctctcgg gctggaaggc tatatacttg gctgagctcc cggctccttc   10320
cagctagggc ggccgtgtgc ccactgcggc tggtcagatg cccgagcctg ccgacgaggg   10380
cctccagttc ctctgggttt ccccaggtga ggagatctaa cagcagctgg tgtggccggg   10440
cccgctcccg tcttcctgtc tggaatgtgg aagggacccc tggcatgcag aaccccccgt   10500
gtgaccacaa gggctgagtg gagcaccggg agcctggtgg agggagagtc cttggcgtgg   10560
ctgaggtgct gcccagcccg gactgccagc tgcaggggtt ttatgttaaa aaaaaaaatg   10620
cctatttgtt caaactactg tgagtcatgt tttctgttct tttgtggcta aaagcagccc   10680
tgcctttatc ccctccgtgt ggtgagtttt ctgacatgta taggtctgct ccagactgcc   10740
gctgatggtc acagtccatt ctgtgccaca cacggcatta ggcactgggg atacaacaga   10800
ggacaaaagg gacaaagatc tctgtcccca tggagctcat agtctagtgg agagatcggg   10860
tgaaataagt atgttacata gtgcttacat tggtttccta gggctgccat aaaggaccac   10920
aaactgaggg gcttgaacaa cagaaagtga ttggctctca gttctagagg ccggaagtct   10980
caagtcaggt tgttggcaga gctgcgctgt ctctgatggc tgtagaggag agcccttccc   11040
ttcctgttcc cggcttctgg ccattctcag cagacgtggg agttccttgg ctcgtagaca   11100
caccactcca gtctccgatt ccatcataac gtggccatct tcagatcatc tttcctctgt   11160
atgtctccat agctccagtt ttttcttttc ttacttttt tttttttaat agaaatgggg   11220
tcttgccatg ctgcccaggt tgatcttgga actcctgggc tcaagcgatc cacccgcctt   11280
ggcctcctaa agtgctggga ttacaggcat gagttactgc gcccggccca aattttctgt   11340
tttttgtttt gtttttttg tttttcaaga cggagtcttg ctctgtcacc tgggctggag   11400
tgcagtgacc tgatcttagc tcactgcaac ctccacctcc tgggttcaag caattcttct   11460
gcctcagcct cccgagtagc tgggattaca ggcatgcacc accaggatcg ctaattttt   11520
tgtatttta gttgagacgg ggtttctccg tgttggtcag gctggtctcg aactcccaac   11580
```

```
ctcaggtgat ctgcctgcct cggcctccca aagtgctggg attacaggca cgagctacca   11640
tgcctggcct aagtttttaa acttctgtag aaacagggtc tcactgtgtt gcccaggttc   11700
aagcaatcct cctgaagtgc agggattaca ggcatgagtg gctgtgtcca gccttttct    11760 ttctttcttt ctttctttct ttctttcttt tctttcttc tttctttctt tctttctttc   11820 tttcttcett tetttctttc tttctttctt tctttctctt tctttcttc tttctttctt   11880 tctttctttc tttctttctt tctttctttc ttcctttctt tcctttcttt cctttcttc   11940 ctttctttct ttcctttctt tctttctttt tttttttttt tcgagacaga gtcttgctct   12000
gtcgcccagg ctggagtgca gtggctcagt ctaagttcac tgcaacctct gcctcctgtg   12060
ttcaagtgat tctcctgcct cagcctccca agtagctggg actacaggtg cgtgccacca   12120
cacccggcta attttgtat tttagtaga cgggggtttt caccatgttg gccaggatgg     12180
tctcaaaccc ctgatctcgt gatgcactca cctcggcctc ccaaagtggt gcaattacca   12240
gcgtgagcaa ctgcacctgg cctcttttct tattttaaat taacttttc cacgtgttct    12300 gatccaggct ccttttccaa attaaaagtg tatatttaaa cattccatct tagacagtgt   12360
gatagtcatg aggtcataga agtagttaag aggaaagtta atctataatg aagatcaagt   12420
tgaagaggaa aagcatcttt tctggagccc tagtcttttg caacatttta caaaacaatg   12480
taggtaaaga aaaggctaat ctataatcag aggaacaaag gttacagctg cctaggttac   12540
agctgcctac cacatgactc agcctccata atcacattcc tttaaggctc aaagtaattt   12600
aaagttccaa caacattgat tctgaattac ttatttttgt agacccttgc aaatgcaccc   12660
acaggcagca gattgctggg cacacagcca tctggggagt ggacctccac tgtcgctggg   12720
cccactggca ttggggacag catttacatg ggagagaaat cagccactgt gtatgcattg   12780
ttgcaggttt tcttttgctc acagccaaac ctaatcctaa ctcatacaag tgggaagttg   12840
tgatcagagg gagaatctag tctgtagaag cattaaatgg ttaagttagc aaattgagga   12900
gaaacatcac aggttattta tttatttaga gacagggtct ggctctgtca cccaggctgg   12960
tgtgtagtgg tgccgtcttg actcactgca acctctggct gctgggttca agtgatcctt   13020
ccacctcagc ctcctgaata gctgggaata gctgggacta caggtgcaca ccaccatgcc   13080
cagctagttt ttggcggtat ttttggtatt ttgttttgtt ttgttttttg agatgagtct   13140
tactctgttg cctagtctcg agtgcagtgg tgcaatctca cctcactgca atctcagcct   13200
cctgagaagc tgggattaca gtcatatgcc accatgcctg gctaattttt gtatttttag   13260
tagagacagg gtttcaccat gttgcccagg ctggtcgtga actcctgagc tcaagcaatc   13320
ctcccgcctc ggcctcccaa attgcaagga ttataggtgt gagccattgc atctggccaa   13380
caaatcagtc agcataggag gagcggatct tgtggagaga gaaggcgtta ggagggaact   13440
aggcaaaccc tggattgact tgtgtgaagt caggtagtga agatgaccaa tatgtaataa   13500
actggtgact ctgggccacg tgccatgcaa tggcacatcc tcatcatcac agctgatctt   13560
gggcaccact acttggtaga aatctccaga aatctggaat cctggacctg gattctctta   13620
gtatgctgta ggggctatta tatgtagcct gtcctcacca tcatcctgaa ggggtagaac   13680
aagaaatcaa cagaatttac ttggaatttt ggttccaaat ggctgttaat taaaaaaaaa   13740
aaaagtgcaa tctcctgctt tcctggtctc ttaactctcc gattcttata tcccatgtct   13800 tttgcactttt ctgattttga ggtatatctc ctttagaaac tctcctatag atggtttcga   13860
ggtggccgtg gtttgtctgc ccctccaaa actcatgttg aaacttcatc tccagtgtgg    13920
```

```
cagtactgag aggggaggct ttaagaggtg actggatcat gagggctttg ccctcaagag    13980
attaatccac tcatggatta atgacttcag gggttagtcg cttaatgggt tatcatggga    14040
ggagaaccag tggcttcatg agaagaggaa gagagacctg aactagcatg tgagcacgct    14100
cagcccccac cctgtgatgc cctgtaccag ctccagactc tgcagagtcc ccaccagcaa    14160
gacctcacca catgcagccc ctcgaccttg gacttcccag cctccagaat tgcgagatat    14220
tccttttctt tataaataac tcagtttcag gtattcagaa aacagactaa gaggctgggt    14280
gcggtggctc atgtctgtaa tcctagcact ttgggaggct gaagtggtag gattgcttga    14340
tctcaggagt tcaagaccag cctgggcaac attgtgagac cctgtctcta caaaaaaaaa    14400
gaaattagct gggcgtggtg gtgcaactcg ggaggccgag gcacaaggat tgcttgagcc    14460
tgagaggttg aggctgcagt gagctacgat catgctactg cactctcgcc tggaaatttt    14520
ttttctttta ttttttgaga cagagtctcg ctctgtcgcc caggctggag tgcagtggtg    14580
caatcttggc tcactgcaag ctccgcctcc cgggttcaag cagttctcct gcctcagctt    14640
cctgtgtagc tgggattaca ggcgcacgcc accacgcccg gctaattttt ttttttgtatt    14700 tttagtagag atggggtttc accatgttgg tcaggctggc cttgaactcc cgaccttgtg    14760
atctgcccgc cttggcctcc cagagtgttg ggattacagg agtgaaccac cgtgcctggc    14820 ctttttttc tttttgagat ggagcctccc tctgtcaccc aggttggagt gcagtggcac    14880
gatcttggct cactgcaac ctccacctcc agggttcaag cgattctcct gcctcagcct    14940
cctgagtagc tgagactata ggcatgtgcc accacaccca gctaattttt tgtatttata    15000
gtagagatgg ggtttcgcca tgttggccag gatggtttcg aactcctgac ctcaaatgat    15060
ccgcccacct cagcctccca tagtgctgag attacagatg tgagccacca ccctgctg    15120 aggatctttg catcagtgtt cattaaggaa tattggcccg taggtttctt ttcttgtagt    15180
gccttcgtct agctttggta ctggggtaat gctggcctca cagaatgagg aagtttttccc    15240 ttcaagcttt tggaaaagtt tgaggattcg tattcttcaa atgtttggta taattttacc    15300
agtgaaggtg tcaggtccag ggattttctt tgtcaagaga tatttgatta ctgattcagt    15360
ctccataata atcataggat ctattcagaa tttctgtttc tttgtgatat catcttggta    15420
ggttttatgt tcctagcaat ttgtccatgt catctaggtt atccaatttg ttgggataca    15480
gttgttcgta gtaccctctt ataatccttt ttatttgcgt agaatgggta gtaatgttcc    15540
tactttcatt tctgatttta gtaatttgag tcttcttgtc ttttcctagt ccatctagcc    15600
aaaggtttgt caattttgtt gatcttttca aataaccaac ttttggtttc attaattttc    15660
tctgttgttt ctctgttctc tatttcattg atctctgctt taatctgtat tatttccttt    15720
ttttctgcta tctttgtgtt tagttagttc ttttctagt tccttaagtt tttaagttag    15780
gttgttaatt tgagatcttg ctttttttc ccctcttacc attattctca agaaatataa    15840
aaataaacac aatcgtacag agaatgaagc actgtaaaag taaagcattg aagagtaaat    15900
atgaaatata ttgcacaaga gggttgagat caaaatacca gaaatataaa ttatatcaat    15960
aaatgtaaat gaactcatgt aacaaaacat tttatcaggc caggcgccag ttgctcacac    16020
ctgtaacgcc agcactttgg gaggctgagg tgggtggatc acctgaggtc aggagttcga    16080
gaccagcctg gccaacatgg tgaaaccccc tctctactaa aaatacaaaa attagccggg    16140
cctggtggtg cgcgcctgta atcccagcta cccgggaggc tgaggcagga gaatcacttg    16200
aacctgggag gcagaggttg cagtgagccg agattgtacc actgcactcc agcctggtga    16260
cagagcgaga ctctgtctca aaaaaaaaaa aaaaaaaaa aaaaaaaaaa aaatatatat    16320
```

```
atatatatat atacacacac acacacacac acacacacac acatatataa aaaactgtat   16380
ataattatat gtaattaata taacaacaaa aattacatag acaattttat ataatttctg   16440
tgtatatgag atatatatta tgtgtgtata tgactgagga agccaagctc ataggcctgt   16500
ggagtgaagt gtttcctcag agaccaggca tgctgttgga aacatgaggg aagaataagc   16560
agttagaacc acctggagac acggatatgc aactttttag ttgacataaa ggactcaata   16620 tagggggttga taacaaaatg gattcaccaa attagttgaa gatcaactaa tttgaagatc   16680
agatcaaaga tcagaggacc ttgggaggaa acacagagat ggagatttat aaagagattt   16740
ataaagagga gatttttaaa gagaatgggc ccggcatgat ggctcatgcc tgtaatccca   16800
gtactttggg aggccgaggc aggcggatca cgaagttgag atcgagacca tcttggccaa   16860
catgttgaaa ccccgtctct actaaaaata caaaaaatt agctgggtgt ggtggcgtgt   16920
gcctgtagtc ccagctactt gggaggctga agccggagaa tggcttgaac ctgggaggca   16980
gaggttgcag tgagccgaga tcgtgccact gcactctagc ctggtgacag agcgagactc   17040
tgtctgaaaa aaaaaaaaa attaaaaaaa tacaaaatta gacgggcatg gtggtgcgtg   17100
cctgtagtcc cagctactcg ggaggctgag gcaggagaat cacttgaacc tgggaggcgg   17160
aggttgcagt gagctgagat cgtgccactg cactccagcc tgggcaacag agtaaggctc   17220
tgtctcaaaa aaaaaaaaa aaaaaaaaa aagaaaaga aaaaaggaa tatgagaat   17280 ataaatggaa atcagcaacc aaaagataac tgaaaaaatc ctttgtatct ggaaactaaa   17340
aacatactac caaataacat tcggacttaa gaataaatca taatgaaagc cccacactaa   17400
aagaggaaag cttcaggacc tggctaaagg aagagaggtt tgtggctgga acaagaacat   17460
ttgcagggtg cccggatccc ttgaagagga caccctgaca ctgaccgtgg aacagccta   17520 cgctacacat gcaggcgttc aggtggagta ctcttcccat actccagaga acaggctgaa   17580
acttttgact cagcaaaggc cagaaggaaa aggggaagtg gtttatcaag tgcctgctgg   17640
agcatataac atcccagaca ctgagcactt gcatacaagt gaccgacatg gctggcccca   17700
ccgcttgcca gtgctgcctg gtcagtgggt tagactcatc ccatgacgct agcagggtag   17760
ttgctcttgt tgtctttgga aggacctttt ctctcctttt ctttttgag atggagtctt   17820 gctcttgttg cctaggcttt agtgcaatgg cacagtcttg gctcattgca acctccgcct   17880
cctgggttca agcgattctc ctgcctcagc ctcccgagta gctgggatta caggcatgtg   17940
ccaccacacc cggctaattt tgtatttta gtagagacga ggtttctcca tgttactcag   18000
gctggtatca aactcccgac cttaggtgat ccacctgctt ggcctccca gagtgctggg   18060 attacaggcg tgagccacca tgcccggcca tggaaggact ttttcaagaa accgatgtgg   18120
tcagttttcc gtatacctcc agtgttctgt ttctggcgtc tgggtgctcc accagcacgg   18180
agaaagacga gtgccctgtg gcctgagtcc caggcactga acactctagc ctgggcagca   18240
gctccgggag gactcagctt cccgagcacc gccctcaggt tgggaatcca cagcagcacc   18300
cacaacacac cacacagtgc accagccatc aaggggcgc acaaatgacc agggctgcct   18360
tccaggcaat ggccactgcc tggtggatcc agttagtaag ccaagagcag tttgaggaca   18420
taccatctcc atctggcatc aaaccaccct gctcactgcg ccagttgttg taaggacacc   18480
ttggatttgt tgtccttaga tatgatgtaa cagacacaga aatgactgcc atggtgggaa   18540
gaagcttata ctcacagttc cctagaaaca ggcggcaccg cacactaaca cgggccacac   18600
ggggaagcac cagtgttggt cggggggcaga gggagggagg ggaactgtgg ggcaagagcc   18660
```

```
tttattgtgg tttgcttagg aaggaacctg agaggcagag tgagcaggtc taggattgcc   18720
tagcttgaat aatttcaatg ggtttggggt aggatgtccc tagttgtcca gtctctgggg   18780
gatagtggtg cagcgtgtaa gagcccagta aaggaggtgg ttggaaggta tgggctctgg   18840
attggttagt atgaatatga aaggcacggc acgcttgcag gtgagtgagt gagttactat   18900
ctctaggaat tggatgagag gatggagtat gatgaacctt tgattcctgg agggccatga   18960
gttcactgtg gtatggaaat gcagctgtgc tgtgatcagt tagtggaggc aaaaattaat   19020
aatgaatttt agaaatgatg gatgcaactc ccaaggagtt agttcactgg acgtataagg   19080
aaatgcaaag taactagaaa caagctaaat ataccatcct attgttctct gtagcaacaa   19140
tgaaggcaaa agatggtgat agggcagatc ctgagattgg gccaagcttg gattgtggct   19200
ggtctgagct acagctattc ccagggccac ttttgagggg gaaaattatg ctgaaacaac   19260
agtgaagatg gttagaatga ttcacaagag agtgggaaa acaaagggaa gagtcaagat    19320
actcatccca gcaggatgga atctttaaag ggttcttaat gaaatggact gaataaagta   19380
ggcattgatg gggtcaaaac aaaggtcatc tccaacaccc ttggaagtcc ttgggtggac   19440
agatgggagc ttctgctggt cccccactat tgaagggccc taaacaaatc tgatttactc   19500
accttagttt ggaagatttt aaaatgttag agggaggccg gcctgtaatc ccagcacttt   19560
gggaggatca cctgaggtca ggagttcgag accaggctga ccaacatggt gaaaccccat   19620
ctctaccaaa aatacaaaaa aatggtcagg cgtggggca cacgcctgta atcccagcac   19680
tttgggaggc tgaggcgggc ggatcatgag gtcaggagat cgagatcatc ctggctaaca   19740
cggtgaaacc ctgtctctac taaaaataca aaaagttagc cgggtgtggt ggcacgtgcc   19800
tgtagtccca gttacttggg aggctgaggc aggagaaccg cttgaaccca ggaggcagag   19860
gttgcagtga gctgagatca caccattgca ctccagcctg gcaacaaga gcaaaactct    19920 gtctaaaaag caaacaaaca aacaaacaga caaactagcc aggcatggtg gcgggtgcct   19980
gtaatcccag ctactcagga ggctgaggca ggagaatcgc ttgaacccag gaggcagagg   20040
ttgcagtaag ctgagatcgc gccattgcgc tccagcctgg gcgacagagt gagactccgt   20100
ctccaggaaa aaaaaaaaag gccagaggga aagatgacaa ggagaaagct gataggtagt   20160
cacctggggc aattgtgcca caatctaatc aagataatga ctgacaccca ctgcggaccc   20220
aaggccatgt ggacatgagc cggtgaaatg gtcaggggct gcaggagaga ctttactggg   20280 acacctttt gtggaaccca agctctgtga ttccaaaatc tatttgtgaa gtcccaatgg    20340
gagcgagagt tcgactggga gaatatggga atgtgatacc tgatggaatg gaaacggtga   20400
gggttgagca ggctttatgc aaagcgactg cagctccttt acctgaatgt actatggggg   20460
tggatattgg gtctggctga ggtgtttctc ttacctagca tgctaaagcg gaaggcatgt   20520
gaatctcccc acctgccaat attgattgga tgtacttgat ggaaaccagt aagattgccc   20580
aagcctgtgc aagttgttca tttgttgtac cgtagcccg ctgaggagca gactggacct    20640
gagggcaaaa gccggagtgc cacctagtgg caaccactgg gattttggac caggaaattt   20700
ccatttgact aacttgctat tggatttaat taaagtccaa ttgcccctat gacttaagga   20760
cataaaataa ccttgaaacc tgaaatactt ataatttctt gggtgatgtt ggggaaatac   20820
tctgatagga gggcagtgcc cagaagggtc catcatcatt tggaaatgat ttttctggaa   20880
acatgctatc tggggaatgc aagaaggccg tcccaagtgg gtgcctcttc ccccacaggc   20940
aacttcagag ccacctaagg agtttcacgg gccacatggg cagtgagtgc cctatgaaca   21000
gctctctatt gaccaacaag agccgcctgg tttatggatg acaggcggct ttcaaggtga   21060
```

```
caggacagct tcctatctgg aagaccatca agaaggtaa aaacaaatca cctcagcagg   21120
ttgaattgac tggtgtttgt gctacatctc acgggcagtg gccaacctgc ccgcacagtc   21180
agcagaaggg caatggaaaa ctggcctatt agtgatccca ctaataggtc cacatgggcc   21240
tgtggacatc attatgggag tcggagggt acattaaagt aggacgtttg atgttcatca   21300
gaagaacccc attccaggat cagggggtga ttggattcag tcagtggata ttctggtgtg   21360
ctcacttaag gaggcctcat gatatgaggg acatacgggg ttgccacagt gcagggatgg   21420
actgagtcta gacatgttcc ccttgcaccc tctgaggcac aaaacaccag taactgttct   21480
gtctgtcaac gagaggcttg ataggcaagt cacactgaag cctgtagccc caggaagtgt   21540
aagtcgtggc aggaacagtc actctgcaca ctgggctcag cttccctgtg gtagatgcaa   21600
atgctcacag cacagtaaaa ggactggaac tcagctgagc gcagtggctc acgcctgtaa   21660
tcccagcatt ttaggaggcc gaggtgggca gatcacctga ggtcaggagt gcgagaccag   21720
cctggccaac atggtgaaac cctgtctcta ctaaaaatat aaaaattagc cgggcatggt   21780
ggcaggtgcc tgtaatctca gctacttggg aggctgaggc aagggaatcg cttgaaccca   21840
ggaggtggag gttgcagtga gccgagaccg cgccatccat tgccctccag cctgggggac   21900
aagagcgaga cttcatctca aaaaaaaaaa aaaaaggta ccaatttgga ctctgccagg   21960
tcacatttct tcagaccaag gaacacattt tacagcacat agtgtccaac agtggcggag   22020
acatcctccc cagagtgatg gtttgatgaa gaattggaat aggcaagtga acatttgtt   22080 gactgaaata ggaaaagcca ggcaaggtgg ctcatgcctg taatcctagc actttgggag   22140
gccgaggcag acggattgct tgagctcaag agtttgagac cagcctgggc aacaatggca   22200
aaatcctgtc tctacaaaaa atacaaaaaa ttagctgggc gtggtgttgc acacctgtaa   22260
tcctagctac tcaggaggct gaggcaggag gatcacctga gcctgcgagg tcaaggctgt   22320
agtgagctgt gttcatacca ctgcactcca gcctgggcaa caaagtaaga cccttcatat   22380
attaccaagt tgggcaacat acatgaaatt ggggttagag tagggaagta tgggtagaat   22440
aagacaggaa aaatatttga agagataaga actgaaaact tttgcagaag ctcaagacac   22500
cccaggcaag gcaagcacca agaaaaccac acccaggcgt gtcacagcca acagttgaaa   22560
accaaaggtg aagagaaaat attaaaagca gatagaggat aacaatacat tatatccagt   22620
ggaaaaataa gactttcagc tgacttagaa aaaatgcaaa tcaggccggg tgcggtggct   22680
caagccagta atcccaacac tttgggagac tgaggggggc aaatcacctg aggtcaggag   22740
ttcaagacca gcttggccaa catggtgaaa ccccatctct acaaaaaata aaaaattag   22800 gcatggtggc atgcagctgt ggtcccagct acttgggagg ctgaggcggg agaattgctt   22860
gagcccagca ggtcaaggct gcaatgagcc tcattgtgt cactgcactc cagctgggtg   22920
acagcagaag accccaccctc aaaaaaaaaa aaaaaaaaaa tggccatact actgagccta   22980
cagaggcctg tttgcagtgt tcctccccgg atagcagggg ctgccaggca cttctgagac   23040
ctgtctagcc agggctggcc tcttggctta gcccctgtga caccaagcga gggaccggct   23100
ggcacccaac tcctgatcat tatgctgcac tgccacaaca gctggggttg gcgggggggg   23160
ggggtgcgtt ccagaggtgg cctctgtgtg ggggtctgct gactgcttct tctgacatcc   23220
tatgggcatg gagacacagg cccaccagcc cttccctacc ccttgcctat ggcttggcca   23280 agccctgtt cggcattggt ttgctctgtc gctgaggtcg tagtctgcag gaagaggctg   23340
accctgagag atgcagggcc cactgctact tgggagaatg cgctgaagga gggaggcctg   23400
```

```
ggaacctcct ggagcaagtg acattgagca gagatggcag aggcagggag gtgggcaagg    23460
ccatggcatg tccccctgccc agctcaaact ttgtcctgaa ggccatggga gcgtgggcct    23520
tcagcggggg catgaggcct tcagtggggg cgtgacctgg ttagctctgt gactggggag    23580
tgctgctctc tgggagaggg gaggctgcgg gcagcccagg gaggaggctg ggcagggttc    23640
cagggtcgga gccaggctcc cgactccccc gatgactctt ccttgcaggg gagaagggga    23700
aagggatctg gggaacgcag ggccatctcc tcctgcacca tggagtgtcc atggagtgga    23760
ggaggacggt gagcccagga ttggctcccc tcttcaaggg gtcctaactg ggacaaaggc    23820
ctggggcggg ggggtctccc ttctcccctt ccactcaggg cacagatgca gactctgtcc    23880
ttggagccca gaggaccata gacccgggta gagtctgcac tgcaagtaca ggcagcagaa    23940
ccccagttac agtgggctgg tggaggcagg aggtcacagg gcgaagcgca ggaccctgcg    24000
gactccaggg cagaggatct gggctggtca ctgctggggg ggcactgcag ctcctctgtc    24060
cagtcctgtg cctagaggcc actagctcta gcattttctc acaggggccc aggggacatc    24120
caagggcttg gggcaggatc cctgctggtc caggctggat ccccccatgc cccgtcccat    24180
cctgttcctg gggaggtatt gttcctgtct ggcctggccg gtggccttga ccccagccca    24240
catgctgtcc ctggctcaaa accgctctgc agctcctagg atgaagtcca aactccttga    24300
catgagccct ccagcccctc tgcagcccca ccccgactcc caccacctcc tggccatgtc    24360
ttcagctcac atatgcttcc ttctttccct ttgctgaaaa ttctcctcct tcagaacctc    24420 cccacccta tcccacccag actggaggcc aggccaccta gggcccagac atctgagtag    24480
gttcgtgtct gcactgcatg gtgctgactt tagtgaaata aaattggaaa ttcattcaca    24540
acccttgcgg ctccttcctt cagagatggc tgattgcagg ggggagtttg ggggaaccca    24600
tcagcatgtt ctgggccctg cagcctctcc agtgtcagcc tgcaccaggc tatttgctct    24660
ctgtaagcca caccgcccct gccatgctcc tttcagcccc agggccttttg catgtgctgt    24720 tcctttgtct agaattcttt catctctcct atacttagat aacacctctt catccatttc    24780
cccagtaaag ccttctctgg cctcaccaat taggtcaaat gttccttaga atgtgttgtg    24840
gggcatggtc tctccctgtg aggacctgtc cagctggacc tccgccttcc tgcgactgta    24900
ttggtgtctt tccctctcaa gcctatgagc tctgcaaggg cagggaccct gtatgatttt    24960
gcctatcgta tgtcctccag ccccccagcac agcgcctggt gtccagtgag agctcagcaa    25020
atactttgtg agttaaggac aggcggctgg gtagatggat cgtctgccta gacagggcag    25080
ttattccgct gtgagcaact cttagagaaa cttcattttt tttcggcgcc tggccgaaac    25140
ttcaagatgt ttcccggcca ggaacggtgg ctcacacctg taatcccagc actttgggag    25200
gctgaggtgg gtggatcacc tgaggtcagg agttcgagac cagcctggcc aacacggtga    25260
aaccccgtct ctactaaaaa tacaaaaatt agctgggtgt ggtggtgggc gcttgtagtc    25320
tcagctactt gggaggctga ggcaggagaa ttgcttgaac ccgggaggcg gaggttgcag    25380
tgagtcgaga ctgagccatt gcgcttcagc ctgggcaaca gagcaagact caaaaaaaaa    25440
aaaaagattt ttcccaagga actgaggcct gactgacatg tgcttgtgtt taccaggact    25500
gtctctttac agagcatcta tccctcccac cttccctccc ctctctattt tgggattact    25560
ggagtcacag actcagcccg tggctggcag caatgctcca cctgctaca gctgcgttca    25620 tcttcctgtc cccagatgtg gccccacctg ctggtgctga ggctagaagt catcacagcc    25680
actccttcgg ccggctagga gagtcaggtg caagaagggt ttatggactc tgagtaaggc    25740
aagcaggggc tgcctgggag gcaaacgccg cggtctggtt gcactggcct ttgagatggg    25800
```

```
cggctccttc atgccatggg caccgcagag gcattggctc tgatccttca acgctgtcgc   25860
agggctcctg aggcttagag acggaggtca cctcctgagt catacacagc tgagacatca   25920
gtgacaggag aggaccccaa ctgcgtggat accagagccc aaggccccgg aaaaggccat   25980
ttcgcgtgcc tccagggtat ggcctgcctg aggaagctgt taccccactg acgttttcgt   26040
agcaacaaca gcttcctcac agaagaggag gggggccgag atattattcc cattcgacac   26100
agtaggaagc tggggcccac gggggccttc ggggcagat ggcaggcagg cttggggaca    26160
gaccccggag ggcaggagcc gggtccgccg cccctccgcc ggcgcctgcg cattgaggcc   26220
cagctcccct ctcaaccccg ccccatcgct tgggttttca aatttgaaac ctgcttcttt   26280
tcccgcccga acgtgtggat cagcggcggg agagggcggg gcagagcgcc agccaatagg   26340
gcatcagagg ctccccgacc ccgccccgag gatgacaaca gcgatccttg agaagccatg   26400
tgcgaatggg cgagcggcgg ccggaggccc cgccccgcg gcacccacgt gcagcggctg    26460
ggcccggcgc tttcagggga ccaccaggcc cccagagcgc cgtgctatgt tgggggctag   26520
tcactagcac ggggctggaa gctgagatca aagacgccaa tgagccggcg tgggtggatg   26580
agtgaggcgc gcaagaagca gcaccggtta gcctgagggt tcgctccagg gccaggcctg   26640
gagccagcgc ccttacctgc ccctggaaag tctgagacca ctcggggcgg ggcggctgcc   26700
ggagggtggg ctgcggctcc gtggcgggtt ccagaggggc ggagcaagg gctgggcgtt    26760 cccgcgggcg gggcgtcccg ggggcggggc gggcccctgt gtttgttgca ccgtgtcagt   26820
tactttgtaa caaaagtgct gcagccgctt gctccggccg gcaccctagg ccggcccgcc   26880
gccagctgtc gccgacatgg aaccccttggc cagcaacatc caggtcctgc tgcaggcggc   26940
cgagttcctg gagcgccgtg agagaggtga ggaaggaccc ttggctgaat tccgggcggc   27000
gacctcgctg acacgggcct ggactggacc tggctcccag cttgaaggat gcaccgccct   27060
aggacagtaa tcccggggcg cctcgcccctc aactcgagag gagtcccggg gcggtagagc   27120
agggacgggt gggggaaatg gtcctggcgc caaaagcctt tccttgaccg tgctgtgcct   27180
ggggctgccg ctgggaccag gtccagcccc agcctgacgc gggcggggac tctctctggc   27240
agaggccgag catggttatg cgtccctgtg cccgcatcgc agtccaggcc ccatccacag   27300
gaggaagaag cgacccccccc aggctcctgg cgcgcaggac agcgggcggt gaggaggccg   27360
ggggcggcgg gagtgggggt ggggtgggc gccgcccctg gtcgggccct cctctgccca    27420
cttgttgctt gcatcttttg ggccaggtgt cccgctccag gaagcgttca gaccccctcct  27480 gccatctccc cactctccaa acacactcac acctttctat tcattcaagg actatttctt   27540
gagcacctct agatgtgccg ggaactgcca acagcagttg gggtcccgct tccactcgca   27600
ctcccgcacc ccacacatca ggccactcac ctcccccgct ggcttcctcc tcttctctcc   27660
tctccccagc cctttgcata tgctgttccc tcctatttga atgcccctcc ctccagtacc   27720
ggcttgggaa acatctgttt ccgcagttag ctgtcacctc tgggaggtcc tttctggcca   27780
gctggcaggc gcccttgtta gggccctcat acccacctgg gcaggcttct gttaagcatt   27840
tggctccgtg tgtctttgac tccctcgcc ctgccagggg actctggtgt ctgaggccag    27900
catgagctct ccacagggga cttgtttggg gcagacatct gtagtggctc ttgagccact   27960
gggggccctg ggattggggc atgggcagta gctgattccc cttcacctca tcctctctgg   28020
cattggcagg tcagtgcaca atgaactgga gaagcgcagg tgagtcccag tcctgccctg   28080
acagcgccag cccccagggg ccactgccct ctggccttcc ctcccctgcc attcctgtgg   28140
```

| | |
|---|---|
| ccggcaaggt ggggctggca ctgccctcca gacctcttcc ccacaggagg gcccagttga | 28200 |
| agcggtgcct ggagcggctg aagcagcaga tgccctggg ggccgactgt gcccggtaca | 28260 |
| ccacgctgag cctgctgcgc cgtgccagga tgcacatcca ggtgaggccc cccactgcgc | 28320 |
| ccggactggc ttgccctggt gtatggaggg ctgtgctatg gaggggctgg tgggactggg | 28380 |
| gaacgagacc tgaggtcaga gctcaagaac tgtgtgactt aggacagctc tctgagcttt | 28440 |
| tactttccag atccattaaa tgggaagaaa agcagacaat aactcagagg gttgttgagg | 28500 |
| cttaaatgag ttcactctat aaatgttcac tgttgctgtt acagctgtta tcacttagat | 28560 |
| cacagctgtg agaccttggg caggttactt agcctgtctg gactaacctt ccctcctgtt | 28620 |
| tgaggggagg ggatggctgt tgaattctgt gatgggatgt atgtgggggt ccttgggact | 28680 |
| gtagagggtt ggtccttgct ctccccctct caccttcaag gcctcctgtt atgggcagtc | 28740 |
| tatcctggtg ccacctggga ggcagctcca gggacaggag gggaaaggac tgagaagacg | 28800 |
| ccagtcactg gtcctcccag ggctcctgct gctgctgggg ctgagctcag tgcccccctgg | 28860 |
| tggacaggag tggatgtgct gaataaaggc ccaggtggcc ctggccatgt cagaagtggc | 28920 |
| cttggaaacc acaggacttt tcctgccctc tagaggaata catgaaggca cagctaggct | 28980 |
| gagggccaac aagttgcaca gctgatgggc ggcagattca ggacccatgc ccagttccct | 29040 |
| ggcttgcgtt atctcctctg acaagtgttt actgagcact ggttctgcta ggccctattc | 29100 |
| taggcactgg gggctgtggc acacaaagac ctatgcgctg ttagtaaata aaccacagct | 29160 |
| gcgggaacag ctgcactgcc gcccggcgtc tgttattacc atcattgtgg ctgagtaaca | 29220 |
| ctctggttgg gtagtggccc agtttctcac acggagcttg cctggcctgg ttctcggatg | 29280 |
| gatgatgtgt gccctcagg ggctggctgg cctgtgggca ggacctgggc agtgctcctt | 29340 |
| ctctggggct ccatcacccc tctcctggat taattcaccg gcctcctccc agccttcctg | 29400 |
| ttacctgttt tgcctccacc aggctgtctt ctactttgct ctagaatgat ctctgcagca | 29460 |
| cacctatcta cccaggccca tctcctgctg aaaacccacc agtggcccct gacaggacaa | 29520 |
| agcctctgct ccccttcctt cctgtgaaac tcaaggccct tcataaccca ggacttgcca | 29580 |
| gtaggctgct cttttggcct catctctccc tgtgccccac agaagctgaa tgctctgtgc | 29640 |
| tcttcccagg ctccctctgc tgtgtcttga cgtttcttcc tccctgtgtt tgcctcggca | 29700 |
| gctcttatct ttctacgccc agtccaaacg cctccatggc ccagttctcc ccttcttgtt | 29760 |
| gaatgaccga atgtaagctt ctgcccactg agggctccgc ctgggagagc ccttggcctt | 29820 |
| ccagtccttg gaacttcagg gctggcagag cttggcggga ggtagggta tgggagggag | 29880 |
| ggtgctaacg ccttcacgct ctcgctcttg tagggatcgt gaccaggagc tacagactgg | 29940 |
| tagcctttgt ttgttctcta gttttctaaa aatttaaatt agctgtcaat ccctcaaaag | 30000 |
| acatttgaca tgaaaaatct gactttccag ctagcttctc gtaaagaaat ggggggccgg | 30060 |
| gcgcggtggc tcacacctat aatctcagca ctttaggagg ctgaggcagg cggattacct | 30120 |
| gaggtcagga gtttgagacc agcctgacca atatggtgaa accccgtctc cactaaaaat | 30180 |
| acaaaaatta gctgggcatg gtggcgggcc cctgtagtcc cagctacttg tgaggccgag | 30240 |
| actagggaat tgcttgaact taagaggtgg aggttgtggt gagccgagat tgtgccactg | 30300 |
| cactccagcc tgggcgacag agcgagactc tgtttcaaaa aaaaaaaca aaaacaaaa | 30360 |
| gaaacgggga gacctggtaa caccgggcct gtttcccatg acagcacatg cctggctcct | 30420 |
| gagccagagt gtacacgcag cagtgcaccc tgctcccagt tcccaccct ggacgccaca | 30480 |
| gcactccagt cctttatcct tgactaggcc ccaaatgcct ttgagattgt ggtgcccccc | 30540 |

```
cacccccaat ctaggcagca ccctgacagg acgtgtgcat ggccggaaag gggctggctt    30600
tctggaggat gtgggtgcaa ccctctgggg cctggattta gtcgccacct gcccggagtg    30660
ggcattggcc ctgtggccgt ggcccggtac tgagtggtgc tggggtgcag cccaagcccc    30720
cacgccgctg accccagccc cttgctcctt tgggatccgc agaagctgga ggatcaggag    30780
cagcgggccc gacagctcaa ggagaggctg cgcagcaagc agcagagcct gcagcggcag    30840
ctggagcagc tccgggggct ggcaggggcg gccgagcggg agcggctgcg ggcggacagt    30900
ctggactcct caggcctctc ctctgagcgc tcagactcag accaaggtga gtgccccgag    30960
gctgaggggt tgtgtggccc tcggggcgag ccaggtcttc tgaccggacc cctccccgcg    31020
cagaggagct ggaggtggat gtggagagcc tggtgtttgg gggtgaggcc gagctgctgc    31080
ggggcttcgt cgccggccag gagcacagct actcgcacgg cggcggcgcc tggctatgat    31140
gttcctcacc cagggcgggc ctctgccctc tactcgtgcc aggcccactt gccaggcagg    31200
agccctcccc aagccttcag ggctgctcgg agtcacctgt tggaatggac taaaaggacc    31260
cttgtgtggg aacaggtgct ccccaaacac cctgctgctg gctgccaggc aggccctctg    31320
gaagggaagg ggcaggactc atcaggacct ccctggaccc ctgcagggca ggcagcttgg    31380
gcccgagccc aagcatttgg ctctgctgcc cccaagggga caggaagcct cttgggcctc    31440
ttcccttcct ggacaaggcc ccctgccttt gcctcacata aactgtacag tattttcatt    31500
aaaagcctct ttcataactt cccgtccata gtcttgccta atgaaaacgg gggaactccc    31560
aaccacagac ccactggaag aggaaataat atcagttccc atcactgaca ctgttggccg    31620
tgccaggcag tgcacttaat tctcacaact tgaggctgtt ctgtctccac ttcacggatg    31680
gtagaaatga ggctgagtga cgtgactcgc ctgaggtcca aaaacagtga agccaagatt    31740
caaaccagag ccttccgact ccagagctgg ggccaactga attcaacaag tatttattga    31800
gtgtctatta tgtgctagat actgagacac atcagagaac aaaaccaaaa gcccctgccct    31860 tgtcgggctt acagtctagc acttaccgcc agttaacctg caggctacct ggagccccgg    31920
gcaagtcacc gcacctctgt gcctcggtcc tcagctgccc aatgggagaa taagcagacc    31980
tggctcagac atgaatcatg tgcttggtgt actgcagatg ccaaactgca tccccacaac    32040
ccaccacgta gacagcagac agggctggaa gttgattttt aatgataaag tacaatgaag    32100
ggagggcaga gaggctaagc ctagctgtct ggggtgctgt ggtggtggta gactggctac    32160
acaaactgtt gctgctgctg ctgcttcttg gtggccgcct tgctggcgag gtccttggcc    32220
ttctctgtag ctgccagtgc cgtctccttt gccttctcct tggcttcctt ggctgtctca    32280
acaagtgttt tggaaggggc ctcgcctgtc gcgaacggca ggtggctgcc tttagaagat    32340
gcctgaaaga ccaacctaat ttccctcccc catgacacca atctcctctg gccaggctc    32400 cactaaaaag gtggtattca ccctcctccc accccagta cagacaagga gtcccagctc    32460
agagcaggga aatgactaac ccagactcca cgcccgctag gctgaatgag cctctcccta    32520
tgaggaatat ccacataccc agaaactcac cttgcagctt agccaagata tattcaaaac    32580
ccttcatagt cttggtcacg ttgcttttga atcgggcaag accaaattcc tggcatgaga    32640
tgagaatggg aaggatactg agttgcccac tgacccagc ccagccccaa caccgaaagc    32700
actgggtccc agagccccag cagccccaac aacactgctc acctggacag ctctggagac    32760
accaaataag ctagaggaga cccaggcttc ccggcggatt tcagtccagc cactgttgtc    32820
agagttcaca cagtaaacac atcgttcctc caccacctat gcagaggcca accacaatcg    32880
```

```
tggaacagtc tttcattttg ccaacttgca cataaatctg actccctgtc acttttcatg    32940
aggcgaagca atacaatgaa aatccattcc ttcccctgac tgcacctcca agtggcactg    33000
acagaacaag aagccataaa taaggtcgtt ttgctctcga aaacctctct tctgactctt    33060
aaactagaag gcaaaaggtc tctctcttga gatcaacaaa gggccttcca gcccatcctg    33120
ctcctggatt ttgttttgtg catctagacg catgcagtgt tttagccgcc ttccaccagc    33180
tgcagctctg gagcttcctg acagtccaaa taaaaacatt tgcccggcgc ggtggctcac    33240
gcctgtaatc ttagcacttt gggaggccga ggcgggcgga tcacttgagg ttaggagttc    33300
gagaccagcc tggccaacat ggtaaaacct tgtctgtact aaaaatacaa aaattagcca    33360
ggcgtggtgg tgtgtgctta gaaatccacc tcttcagaag gctgaggcac gagaattgct    33420
taaacccagg aggtggcagt ggcagtgagg tgagatcatg tcactacact ccaacctggg    33480
tgagactctt gtcaccagaa aaaacaaaa aacagaaaaa aaaaaaagaa aagcactgcc    33540
tccgccactc agcatcactc ctgtgagtcc aacatatatc tgtgccatag atgccagatg    33600
ggagcgcttt gcatttagaa cttaggacaa ctccgtaaga taggtacccc tcccccactg    33660
tatgaatgag tcaaaggaca ggtccagaga ggatggccag ctgaaaagaa gaaaacctga    33720
ggtcatactc tacagctgtc aaccctcagt aacccagacc tgcctccggc cacaaaagct    33780
gccttatggc tctctagcca catgtatctg aggagctctc tatctcgggg ggagggaga    33840 gggggaggtg cagaatcaca acaggaggtg tctcaccatc agccgggcgt ggttgatgtt    33900
ccaggtgaag gtagtcatgg tctgattctg tgggtccaca atagagtcct ccaggacgta    33960
caccgagtga gcaacattgg caggaaatag tcgctcggcc cagcgtggca tcctgttggt    34020
cttggtcagg agtcgccggg acagcagttt ctggtcaggg gtcacctccc ggtgtactat    34080
gtcttccgtc aagacatgtt tgctgcaggt gtcagggtga aggtgaccct cagaagcttg    34140
cccctaagag actgcccgag gggattccca tttggaggct ccgggcctag agaggccacg    34200
ccttcccgta accttgcagg gtggtatgtg ctatggttca aaccagagtt aagggcccat    34260
cccagggcaa attcccactc ccgccatctg actgacctgg attcctgcct tctagcagga    34320
atggacctca tgatttattg cacccccagga aagcgccacg ggcagagaaa taggattttcc    34380 aactccaaga tccctcccaa ctcccatact gccgcctctt cttgtctcac cacactgaga    34440
aaagaatctt acactaaggt ctcaagtaaa ccaccaccca ggcccaacct cccttcagga    34500
ccttgcaggc ctggcctggc cgcttcccg ataaggtcta cctaggattc gatatcgagt    34560
ccttcctggt cccagtactt gggggttacc cataattcga tctccagata gcagatggc    34620 gcggttttgc tcttccaaat accacgtacc tatagggatt cgggtaccgc tgccagaagg    34680
cggcgaacac ttggtcccag gaactccgga gcacgctctg gcccaggaaa tacttcacca    34740
tcgtcccggc cgaagcgggc tcagcacccg cgcagcatca ggggtgcgga gcctgggagg    34800
cacgcgaggg ccgggccggg ccggggctcg gcgcacaccc gccgccaggc tcgtagctca    34860
gtcaccaccg caccgcgccc aagcagctgc cgccgccgcc gccgccgcca tgagttgtcc    34920
ggccgcgcgc cacttccggc gcagccacac agtagccacc gcttccggcg cccgcgccac    34980
gtgaccttgc ggccccgccc cctcgccctc tagcccccct ccgcgggagt cgcggcgctg    35040
cgggtaggag ccgggttgcg ggagacccca ggttcggttg ggattcccag ccagaacgga    35100
gcttaagccg ggcaggcgag cgaatgacgg agtagcgagc tgcacggcgg cgtgctgcgc    35160
tgttgaggac gctgtcccgc gcgctcccag gccgccccga ggcttggggt cttcgaagga    35220
taatcggcgc ccggggccga acagcggggg cacacggggc gctgccgaag tgcaaggcca    35280
```

```
cggccagagc tcgagcccga cgcgctgtct ggagtcgtag gttggcgccg tttggggtcg    35340
gggtctgagg cttgggcgct gcctgggccg agcggagatc ggggtttgcc tcccgtcccc    35400
gctcaggacc ctgacgtggc tgaagcggcc ccgggagcat gagcgggcag cgcgtggacg    35460
tcaaggtggt gatgctgggc aaggagtacg tgggcaagac tagcctggtg gagcgctacg    35520
tgcacgaccg ctttctggtg gggccttatc agaacgtgag tgcatccgga ggggccaggc    35580
acggtgggcg ggggagtggg gggccggtaa tctgcaccta tggccccgat ctcttccctc    35640
tcgttgcaga ccatcggggc cgccttcgtg gccaaggtga tgtcggtcgg agaccggact    35700
gtgacattag gtatttgggt aagtcccccg gccatctatt cttgggagac tcattcctga    35760
ggaggtgtag gtcctgccta ttactggttg atttgtggcc tcacagaccc atttctcata    35820
gacccgtttc cttatctgga aaatagcggg gtctggagaa cgtggcctta agtttgactc    35880
aggccttact ctttaggaca cagcaggctc tgagcgctat gaggccatga gtagaatcta    35940
ctatcggggt gccaaggctg ccatcgtctg ctatggtaag ggggggggggg gtttgggctg    36000 tctcacaaga aaagatgggt gccaggctag ccagagaaca gcccttgacc acttggttgt    36060
ctcctgcatg ccgcacacca agacctcaca gacagcagca gctttgagcg agcaaagttc    36120
tgggtgaagg aactgcgcag cctagaggag gtaggtgaac agacctcact agaacactag    36180
gggctggggt tttgttggcc tgtggaggtg acccttgtct tctgcctcag ggctgccaaa    36240
tctacttatg tggcaccaag agtgacctgc tggaagaaga ccggaggcgt cgacgtgtgg    36300
acttccacga cgtccaggac tatgcagaca gtagctgctc ctcagcccct tggggggtgg    36360
gggtgtgtgg ctgtctgggt ggatcaaaga aaatagggac tgccttggct gccagggcaa    36420
ggtgctctag gaggtcttcc tggcctcctt gaactgtggg gtccaggaga ctccctgaac    36480
tgctagccct cccttttgtc tgtttatcta attctcaggt atgaggcttt agtcacttct    36540
ctttacagat atcaaagctc agctctttga aacatccagc aagacaggcc agagtgtggg    36600
tgagtgctgt gctggagcct cacagcagga acatgcaggg gcaccagagg aagctgaata    36660
gggcacagag ggctgggtca ctgggagatc ccagggctac tggcattggg ccctcgctga    36720
tcatcatttt tcctgccaga cgagctcttc cagaaagtgg cagaggatta cgtcagtgtg    36780
gctgccttcc aggtgatgac aggtgtgtgc ttccccagcc tttatggaga cttactctag    36840
gcccacagca tctagcccct ttcctgagtt acctgatccc aacagaatgg tgctgagctg    36900
ccacctctct ttttgacaga ggacaagggc gtggatctgg gccagaagcc aaaccccctac   36960 ttctacagct gttgtcatca ctgagtcagc actcacctgg c                       37001
```

<210> SEQ ID NO 2
<211> LENGTH: 23
<212> TYPE: DNA
<213> ORGANISM: Artificial sequence
<220> FEATURE:
<223> OTHER INFORMATION: synthetic primer

<400> SEQUENCE: 2
tttgttgcac cgtgtcagtt act                                             23

<210> SEQ ID NO 3
<211> LENGTH: 18
<212> TYPE: DNA
<213> ORGANISM: Artificial sequence
<220> FEATURE:
<223> OTHER INFORMATION: synthetic rimer

```
<400> SEQUENCE: 3
tggccaaggg ttccatgt                                                   18

<210> SEQ ID NO 4
<211> LENGTH: 19
<212> TYPE: DNA
<213> ORGANISM: Artificial sequence
<220> FEATURE:
<223> OTHER INFORMATION: synthetic probe

<400> SEQUENCE: 4
ctgcagccgc ttgctccgg                                                  19

<210> SEQ ID NO 5
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 5
catccaccca cgccgg                                                     16

<210> SEQ ID NO 6
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 6
ggccctggag cgaacc                                                     16

<210> SEQ ID NO 7
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 7
agccgcagcc caccct                                                     16

<210> SEQ ID NO 8
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 8
ataaccatgc tcggcc                                                     16

<210> SEQ ID NO 9
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 9
cacagggacg cataac                                                     16

<210> SEQ ID NO 10
<211> LENGTH: 16
```

```
<212> TYPE: DNA
<213> ORGANISM: Artificial sequence
<220> FEATURE:
<223> OTHER INFORMATION: synthetic oligonucleotide

<400> SEQUENCE: 10
catcatagcc aggcgc                                                       16

<210> SEQ ID NO 11
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 11
aggaacatca tagcca                                                       16

<210> SEQ ID NO 12
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 12
ggattactgt cctagg                                                       16

<210> SEQ ID NO 13
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 13
caagcaacaa gtgggc                                                       16

<210> SEQ ID NO 14
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 14
taaacacttg tcagag                                                       16

<210> SEQ ID NO 15
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 15
atccatccga gaacca                                                       16

<210> SEQ ID NO 16
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 16
```

```
cacatcatcc atccga                                                      16

<210> SEQ ID NO 17
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 17
gtcattcaac aagaag                                                      16

<210> SEQ ID NO 18
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 18
ccttccctga aggttcctcc                                                  20
```